US009222071B2

(12) United States Patent
Moriarty et al.

(10) Patent No.: US 9,222,071 B2
(45) Date of Patent: *Dec. 29, 2015

(54) CELL THERAPY METHOD FOR THE TREATMENT OF TUMORS

(75) Inventors: Ann Moriarty, Poway, CA (US); Didier J. Leturcq, San Diego, CA (US); Juli Degraw, San Diego, CA (US); Michael R. Jackson, Del Mar, CA (US); Per A. Peterson, Rancho Sante Fe, CA (US); Marja Heiskala, Oitti (FI)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 1331 days.

This patent is subject to a terminal disclaimer.

(21) Appl. No.: 12/014,863

(22) Filed: Jan. 16, 2008

(65) Prior Publication Data

US 2009/0305418 A1    Dec. 10, 2009

Related U.S. Application Data

(63) Continuation of application No. 10/080,013, filed on Feb. 19, 2002, now abandoned.

(60) Provisional application No. 60/270,252, filed on Feb. 20, 2001.

(51) Int. Cl.
| | |
|---|---|
| *C12N 5/10* | (2006.01) |
| *C12N 5/00* | (2006.01) |
| *C12N 5/0783* | (2010.01) |
| *A61K 48/00* | (2006.01) |
| *A61K 39/00* | (2006.01) |
| *A61K 41/00* | (2006.01) |
| *C12N 5/07* | (2010.01) |
| *A61K 35/12* | (2015.01) |

(52) U.S. Cl.
CPC .......... *C12N 5/0636* (2013.01); *A61K 39/0011* (2013.01); *A61K 41/00* (2013.01); *A61K 48/00* (2013.01); *C12N 5/0601* (2013.01); *A61K 2035/124* (2013.01); *A61K 2039/5154* (2013.01); *A61K 2039/5156* (2013.01); *A61K 2039/5158* (2013.01); *A61K 2039/55527* (2013.01); *A61K 2039/55533* (2013.01); *A61K 2039/55538* (2013.01); *C12N 2501/23* (2013.01); *C12N 2501/515* (2013.01); *C12N 2502/99* (2013.01); *C12N 2510/00* (2013.01)

(58) Field of Classification Search
CPC ... A61K 39/0011; A61K 48/00; C12N 5/0601
USPC .............. 435/69.1, 320.1, 348; 530/350, 300, 530/328; 536/23.5
See application file for complete search history.

(56) References Cited

U.S. PATENT DOCUMENTS

| | | | |
|---|---|---|---|
| 4,401,756 A | 8/1983 | Gillis | |
| 4,407,945 A | 10/1983 | Gillis | |
| 4,473,642 A | 9/1984 | Gillis | |
| 4,530,901 A | 7/1985 | Weissmann | |
| 4,695,623 A | 9/1987 | Stabinsky | |
| 4,897,471 A | 1/1990 | Stabinsky | |
| 4,992,367 A | 2/1991 | Cullen | |
| 5,314,813 A | 5/1994 | Peterson et al. | |
| 5,397,703 A | 3/1995 | De Boer et al. | |
| 5,487,974 A | 1/1996 | Boon et al. | |
| 5,529,921 A | 6/1996 | Peterson et al. | |
| 5,583,031 A | 12/1996 | Stern | |
| 5,585,461 A * | 12/1996 | Townsend et al. | 530/328 |
| 5,587,289 A | 12/1996 | Lurquin et al. | |
| 5,637,483 A | 6/1997 | Dranoff et al. | |
| 5,645,837 A | 7/1997 | Jameson et al. | |
| 5,662,907 A | 9/1997 | Kubo et al. | |
| 5,759,783 A | 6/1998 | Lurquin et al. | |
| 5,820,866 A | 10/1998 | Kappler et al. | |
| 5,827,642 A | 10/1998 | Riddell et al. | |

(Continued)

FOREIGN PATENT DOCUMENTS

| | | |
|---|---|---|
| CA | 2069541 | 11/1993 |
| EP | 0814838 | 5/2003 |

(Continued)

OTHER PUBLICATIONS

Japanese Pat App No. 2012-20842 Filed Feb. 2, 2012, Japanese Office Action Dated Oct. 25, 2013.
Japanese Patent App No. 2012-20842 Filed Feb. 2, 2012, Japanese Office Action Dated Mar. 19, 2014.
Kim et al., Folate Binding Protein Peptide 191-199 Presented on Dendritic Cells Can Stimulate CTL from Ovarian And Breast Cancer Patients:, Anticancer Res. (1999) 19(4B); 2907-2916.
Chen et al., "Marked Differences in Human Melanoma Antigen-Specific T Cell Responsiveness after Vaccination Using a Functional Microarray" PLOS Medicine 2(10) 1018-1030 (2005).
Robbins et al., "A Mutated β-Catenin Gene Encodes a Melanoma-specific Antigen Recognized by Tumor Infiltrating Lymphocytes" Journal of Experimental Medicine 183; 1185-1192 (1996).

(Continued)

*Primary Examiner* — Stephen Rawlings
(74) *Attorney, Agent, or Firm* — Myra H. McCormack

(57) ABSTRACT

T cell responses are often diminished in humans with a compromised immune system. We have developed a method to isolate, stimulate and expand naïve cytotoxic T lymphocyte precursors (CTLp) to antigen-specific effectors, capable of lysing tumor cells in vivo. This ex vivo protocol produces fully functional effectors. Artificial antigen presenting cells (AAPCs; *Drosophila melanogaster*) transfected with human HLA class I and defined accessory molecules, are used to stimulate CD8$^+$ T cells from both normal donors and cancer patients. The class I molecules expressed to a high density on the surface of the *Drosophila* cells are empty, allowing for efficient loading of multiple peptides that results in the generation of polyclonal responses recognizing tumor cells endogenously expressing the specific peptides. The responses generated are robust, antigen-specific and reproducible if the peptide epitope is a defined immunogen. This artificial antigen expression system can be adapted to treat most cancers in a significant majority of the population.

11 Claims, 29 Drawing Sheets

(56) References Cited

U.S. PATENT DOCUMENTS

| | | | |
|---|---|---|---|
| 5,827,737 | A | 10/1998 | Peterson et al. |
| 5,843,648 | A | 12/1998 | Robbins et al. |
| 5,844,075 | A | 12/1998 | Kawakami et al. |
| 5,874,560 | A | 2/1999 | Kawakami et al. |
| 5,994,523 | A | 11/1999 | Kawakami et al. |
| 6,075,122 | A | 6/2000 | Cheever et al. |
| 6,140,050 | A | 10/2000 | Sahin et al. |
| 6,355,479 | B1 * | 3/2002 | Webb et al. ............ 435/325 |
| 6,461,867 | B1 * | 10/2002 | Cai et al. ............... 435/348 |
| 2006/0234310 | A1 | 10/2006 | Cai et al. |

FOREIGN PATENT DOCUMENTS

| | | |
|---|---|---|
| JP | 2001-89389 | 4/2001 |
| WO | 97/32970 | 2/1992 |
| WO | 93/17095 | 9/1993 |
| WO | 95/34817 | 6/1994 |
| WO | 96/05287 | 8/1994 |
| WO | WO 96/06929 A2 | 3/1996 |
| WO | WO 96/27392 A1 | 9/1996 |
| WO | WO 96/34015 A1 | 10/1996 |
| WO | 97/10002 | 3/1997 |
| WO | 92/01459 | 9/1997 |
| WO | 99/54345 | 4/1998 |
| WO | 99/37313 A1 | 7/1999 |
| WO | 00/25722 | 9/1999 |
| WO | 01/57068 A1 | 8/2001 |
| WO | 01/59073 A2 | 8/2001 |
| WO | 02/04603 A2 | 1/2002 |
| WO | 02/65992 | 8/2002 |

OTHER PUBLICATIONS

Yee et al., "Prospects for adoptive T cell therapy" Current Opinion Immunology 9; 702-708 (1997).

Lens, Marko, "The role of vaccine therapy in the treatment of melanoma", Expert Opin Biol Ther. Mar. 2008; 8: 315-323.

Xia et al., "Combinational adenovirus-mediated gene therapy and dendritic cell vaccine in combating well-established tumors", Cell Research Mar. 2006; 16(3): 241-259.

Schietinger et al, "Specificity in cancer immunotherapy", Seminars in Immunology, Oct. 2008; 20(5): 276-85.

Prehn, Richmond, "On the nature of cancer and why anticancer vaccines don't work", Cancer Cell Int. Aug. 1, 2005; 5(1): 25; p. 1-5.

Morris et al., "Therapeutic Cancer Vaccines", Surgical Oncology Clinics of N. Am. Oct. 2007; 16(4): 819-831.

Finke et al., "Where have all the T cells gone? Mechanisms of immune evasion of tumors", Immunology Today Apr. 1999; 20(4): 158-160.

Mitchell, M. et al., "Phase 1 Trial of Adpotive Immunotherapy with Cytolytic T Lymphocytes Immunized Against a Tryosinase Epitope", Journal of Clinical Oncology, vol. 20, No. 4, Feb. 2002, pp. 1075-1086.

Guelly C. et al., "Activation Requirements of Circulating Antigen-Specific Human CD8+Memory T Cells Probled with Insect Cell-Based Artificial Antigen-Presenting Cells", Eur. J. Immunology, vol. 32, Jan. 2002, pp. 182-192.

Agarwala, S.S. et al. "Melanoma", Immunotherapeutic Approaches, BioDrugs, Sep. 12, 1999, (3) pp. 193-208.

Babcock, B. et al. "Ovarian and Breast Cytotoxic T Lymphocytes Can RecognizePeptides from the Amino Enhancer of Split Protein of the Notch Complex", Molecular Immunology, 35, (1998) pp. 1121-1133.

Brichard, V. et al. "The Tyrosinase Gene Codes for an Antigen Recognized by Autologous Cytolytic T Lymphocytes on HLA-A2 Melanomas", J. Exp. Med. vol. 178, Aug. 1993, pp. 489-495.

Brossart, P. et al. "Identification of HLA-A2-Restricted T-Cell Epitopes Derived from the MUC1 Tumor Antigen for Broadly Applicable Vaccine Therapies", Blood Journal, vol. 93, No. 12 (Jun. 15, 1999), pp. 4308-4317.

Chen, Ji-Li et al. "Identification of NY-ESO-1 Peptide Analogues Capable of Improved Stimulation of Tumor-Reactive CTL", The Journal of Immunology, 2000,165: pp. 948-955.

Creagan, E.T. et al. "Phase II Study of Recombinant Leukocyte A Interferon (rIFN-αA) in Disseminated Malignant Melanoma", Cancer 54 (1984) pp. 2844-2849.

Dorval, T. et al. "Clinical Phase II Trial of Recombinant DNA Interferon (Interferon Alfa 2b) in Patients with Metastatic Malignant Melanoma", Cancer 58 (1986) pp. 215-218.

Fisk, B. et al. "Identification of an Immunodominant Peptide of HER-2/neu Protooncogene Recognized by Ovarian Tumor-Specific Cytotoxic T Lymphocyte Lines", J. Exp. Med. vol. 181, Jun. 1995, pp. 2109-2117.

Kawashima, I. et al. "The Multi-Epitope Approach for Immunotherapy for Cancer:Identification of Several CTL Epitopes from Various Tumor-Associated Antigens Expressed on Solid Epithelial Tumors", Human Immunology 59, (1998) pp. 1-14.

Kirkwood, J.M. et al. "High- and Low-Dose Interferon Alfa-2b in High-Risk Melanoma: First Analysis of Intergroup Trial E1690/59111/C9190", Journal of Clinical Oncology, 18 (12) Jun. 2000, pp. 2444-2458.

LaTouche, J-B et al. "Induction of Human Cytotoxic T Lymphocytes by Artificial Antigen-Presenting Cells", Nature Biotechnology, vol. 18, Apr. 2000, pp. 405-409.

Legha, S.S., "Interferons in the Treatment of Malignant Melanoma, A Review of Recent Trials", Cancer 57: (1986) pp. 1675-1677.

Mackensen, A. et al. "Phase I Study in Melanoma Patients of a Vaccine with Peptide-Pulsed Dendritic Cells Generated In Vitro From CD34 Hematopoietic Progenitor Cells", Int. J. Cancer: 86, (2000) pp. 385-392.

Stimpfli, M. et al. "Expression of Mucins and Cytokeratins in Ovarian Cancer Cell Lines", Cancer Letters 145 (1999) pp. 133-141. Elsevier Science, Ireland.

Sun, S. et al. "Dual Function of *Drosophila* Cells as APCs for naïve CD8+ T Cells: Implications for Tumor Immunotherapy", Immunity, vol. 4, Jun. 1996, pp. 555-564.The Scripps Research Institute, La Jolla, California.

Vonderheide, R.H. et al. "Equivalent Induction of Telomerase-Specific Cytotoxic T Lymphocytes from Tumor-Bearing Patients and Healthy Individuals", Cancer Research 61, Dec. 1, 2001, pp. 8366-8370. Departments of Adult Oncology Boston, MA.

Vissers, J.L. et al. "The Renal Cell Carcinoma-Associated Antigen G250 Encodes a Human Leukocyte Antigen (HLA)-A2.1-Restricted Epitope Recognized by Cytotoxic T Lymphocytes", Cancer Research 59, Nov. 1, 1999, pp. 5554-5559. University Hospital Nijmegen St. Radboud, the Netherlands.

Yee, C. et al. "Melanocyte Destruction After Antigen-Specific Immunotherapy of Melanoma: Direct Evidence of T Cell-Mediated Vitiligo", J. Exp. Med. vol. 192, No. 11, Dec. 4, 2000, pp. 1637-1643. Clinical Research Division Seattle,Washington.

Devries, I. Jolanda M. et al. "Maturation of Dendritic Cells Is a Prerequisite for Inducing Immune Responses in Advanced Melanoma Patients", Clinical Cancer Research, vol. 9, Nov. 1, 2003, pp. 5091-5100.

Rosenberg, S.A. et al. "Adoptive Cell Therapy for the Treatment of Patients with Metastatic Melanoma", Current Opinions in Immunology, 2009, 21, pp. 233-240.Elsevier.

Lollini et al., "New Target Antigens for Cancer Immunoprevention", Curr. Cancer Drug Targets, May 2005; 5(3): 221-228.

Lollini et al., "Cancer immunoprevention:tracking down persistent tumor antigens", Trends Immunol., Feb. 24, 2003 (2): 62-66.

Bins et al., "Phase I Clinical Study with Multiple Peptide Vaccines in Combination with Tetanus Toxoid and GM-CSF in Advanced-stage HLA-A*0201-positive Melanoma Patients", J. Immunother., Feb.-Mar. 2007; 30(2) 234-239.

Harlin et al., "Tumor progression despite massive influx of activated CD8+ T cells in a patient with malignant melanoma ascites", Cancer Immunol. Immunother., 2006; 55: 1185-1197.

Mortarini et al., "Lack of Terminally Differentiated Tumor-specific CD8+ T Cells at Tumor Site in Spite of Antitumore Immunity to Self-Antigens in Human Metastic Melanoma", Cancer Res May 15, 2003; 63: 2535-2545.

Wang et al., "T-cell-directed cancer vaccines: the melanoma model", Exp. Opin Biol. Ther. 2001; 1(2): 277-290.

(56) References Cited

OTHER PUBLICATIONS

Bodey et al., "Failure of Cancer Vaccines: The significant Limitations of this Approach to Immunotherapy", Anticancer Research, 2000; 20: 2665-2676.
Cox et al., "Identification of a Peptide Recognized by Five Melanoma-Specific Human Cytotoxic T Cell Lines", Science, 1994; 264:716-719.
Ezzelli, "Cancer Vaccines An Idea Whose Time has Come", Journal of NIH Research, 1995; 7:46-49.
Spitler, Lynn, "Cancer Vaccines: The Interferon Analogy", Cancer Biotherapy, 1995; 10:1-3.
Mellman, "Where Next of Cancer Therapy", The Scientist, 2006; 20 (1): 47 published on the internet; pp. 1-8.
Lee et al., "Increased Vaccine-Specific T Cell Frequency After peptide-Based Vaccination Correlates with Increased Susceptibility to In Vitro Stimulation But Does Not Lead to Tumor Regression", Journal of Immunology, 1999; 163: 6292-6300.
Zaks et al., "Immunization with a Peptide Epitope (p. 369-377) from HER-2/neu Leads to Peptide-specific Cytotocix T Lymphocytes That Fail to Recognize HER-2/neu+ Tumors", Cancer Research, 1998; 58: 4902-4908.
Gao et al., "Tumor Vaccination That enhances Antitumor T-Cell Responses Does Not Inhibit the Growth of Established Tumores Even in Combination with Interleukin-12 Treatment: The Importance of Inducing Intratumoral T-Cell Migration", Journal of Immunotherapy, 2000; 23: 643-653.
Bocchia et al, "Antitumor vaccination: where we stand", Haematologica, 2000; 85: 1172-1206.
Gura, Trisha, "Systems for Identifying New Drugs are Often Faulty", Science, 1997; 278: 1041-1042.
Allison, et al. "Manipulation of Co-Stimulatory Signals to Enhance Anti-Tumor TCells Responses", Curr. Op. Immunology (1995) 7(5): pp. 682-686.
Bakker, et al. "Melancocyte-Lineage-specific Antigen gp100 is Recognized by Melanoma-Derived Tumor-Infiltrating Lymphocytes", J. Exp. Med. (1994) 179 (3): pp. 1005-1009.
Gaugler, et al. "Human Gene MAGE-3 Codes for an Antigen Recognized on a Melanoma by Autologous Cytolytic T Lymphocytes", J. Exp. Med. (1994) 179(3): pp. 921-930.
Kawakami et al., "Recognition of Multiple Epitopes in the Human Melanoma Antigen gp100 by Tumor-Infiltrating T Lymphocytes Associated with In Vivo Tumor Regression", J. Immunol. (1995) 154(8) pp. 3961-3968.
Kawakami et al. Identification of the Immunodominant Peptides of the MART-1 Human Melanoma Antigen Recognized by the Majority of HIA-A2-Restricted Tumor Infiltrating Lymphocytes:, J. Exp. Med. (1994) 180(1): pp. 347-352.
Robbins, et al. "Recognition of Tyrosinase by Tumor-Infiltrating Lymphocytes from a Patient Responding to Immunotherapy", Cancer Res. (1994) 54: pp. 3124-3126.
Schneider, I. et al. "Differentiation of Larval *Drosophila* Eye-Antennal discs in Vitro", Exp. Zool. (1964) 156(1) pp. 91-104.
Skipper, et al. "An HLA-A2-Restricted Tyrosinase Antigen on Melanoma Cells Results from Post Translations Modification and Suggests a Novel Pathway for Processing of Membrane Proteins", J. Exp. Med. (1996) 183(2): pp. 527-534.
Albert et al., "Dendritic Cells Acquire Antigen from Apoptotic Cells and Induce Class I-Restricted CTLs", Nature, 1998, 392: pp. 86-89.
Alderson, M.R., et al. "Interleukin 7 Enhances Cytolytic T Lymphocyte Generation and Induces Lymphokine-activated Killer Cells from Human Peripheral Blood", 1990. J. Exp. Med. vol. 172:577-587.
Alters, et. al, Immunotherapy of cancer: Generation of CEA specific CTL using CEA peptide pulsed dendritic cells, Dendritic cells in Fundamental and Clinical Immunology (excerpt from book), 1997, 417, 519-524.
Altman et al, "Phenotypic Analysis of Antigen-Specific T Lymphocytes", Science, vol. 274, Oct. 4, 1996, pp. 94-97.

Angelichio et al, "Comparison of Several Promoters and Polyadenylation Signals for Use in Heterologous Gene Expression in Cultured *Drosophilia* Cells", Nuc. Acids Res., vol. 19, No. 18, pp. 5037-5043, 1991.
Baxevanis et al, "Tumor-Specific CD4+ T Lymphocytes from Cancer Patients are Required for Optimal Induction of Cytotoxic T Cells against the Autologous Tumor," J. Immun. (2000) 164:3902-3912.
Bellone et al, "In Vitro Priming of Cytotoxic T Lymphocytes against Poorly Immunogenic Epitopes by Engineered antigen-presenting Cells", Eur. J. Immunology 24: 2691-2698, 1994.
Bhardwaj et al., IL-12 in Conjunction with Dendritic Cells Enhances Antiviral CD8+CTL Responses in Vitro, J. of Clinical Investigation, vol. 98, No. 3, Aug. 1996, pp. 715-722.
Boog et al, "Specific Immune Responses Restored by Alteration in Carbohydrate Chains of Surface Molecules on Antigen-Presenting Cells", Eur. J. Immunol. 1989. 19:537-542.
Brown, J.P. et al, Protein Antigens of Normal and Malignant Human Cells Identified by Immunoprecipitation with Monoclonal Antibodies, 1980 Issue of Jun. 10, J. of Biological Chemistry, vol. 255, No. 11: 4980-4983.
Burshtyn et al., "High Occupancy Binding of Antigenic Peptides to Purified, Immuno-adsorbed H-2Db$\beta$2 m Molecules", J. of Immunol. vol. 151, 3070-3081, No. 6, Sep. 15, 1993.
Cai et al "Probing the activation requirements for naïve CD8 + T cells with *Drosophilia* cell transfectants an antigen presenting cells," Immunological Reviews, 1998, 165: 249-265.
Cai et al., Requirements for Peptide-Induced T Cell Receptor Downregulation on Naïve CD8 + T Cells., J. Exp. Med, vol. 185, No. 4, Feb. 17, 1997 pp. 641-651.
Cai, et al, "Influence of Antigen Dose and Costimulation on the Primary Response of CD8 + T Cells in Vitro," J. Exp. Med. 1996, 183, 2247-2257.
Chen et al., "Costimulation of T Cells for Tumor Immunity", Imm. Today vol. 14, No. 10:1993 pp. 483-485.
Chikamatsu et al, "Generation of Anti-p53 Cytotoxic T Lymphocytes from Human Peripheral Blood Using Autologous Dendritic Cells", Clinical Cancer Res, vol. 5 1281-1288, Jun. 1999.
Corr, M. et al, "T Cell Receptor-MHC Class I Peptide Interactions: Affinity, Kinetics, and Specificity", Science, vol. 265, Aug. 12, 1994, pp. 946-949.
Darrow, T.L. et al, "The role of HLA class I antigens in recoginition of melanoma cells by tumor-specific cytotoxic T lymphocytes", Journal of Immunology, 1989, vol. 142, 3329-3335.
De Bruijn et al., "Peptide Loading of Empty Major Histocompatibility Complex Molecules on RMA-S Cells Allows the Induction of Primary Cytotoxic T Lymphocyte Responses", Eur. J. Immunol. 1991, 21: 2963-2970.
De Wall Malefyt et al., "CD2/LFA-3 or LFA-1/1CAM-1 but not CD28/B7 Interactions can Augment Cytotoxicity by Virus-Specific CD8+ Cytotoxic T Lymphocytes", Eur. J. Immunol. 1993, 23: 418-424.
Gagliardi, et al, "Presentation of Peptides by Cultured Monocytes or Activated T Cells Allows Specific Priming of Human Cytotoxic T Lymphocytes in Vitro", Int. Immunol. vol. 7, No. 11, pp. 1741-1752. (1995).
Germain, "MHC-Dependent Antigen Processing and Peptide Presentation: Providing Ligands for T Lymphocyte Activation", Cell, vol. 76, 287-299, Jan. 28, 1994.
Goldstein et al, Cytotoxic T cell activation by class I protein on cell-size artificial membranes: antigen density and LYT-2/3 function, Journal of Immunology 138(7):2034-2043 1987.
Godeau, F.,et al, "Expression of a mouse class I MHC molecule in insect cells using a baculovirus vector", Journal of Cell Biology, 107( ): Abstract # 2092, 1988.
Godeau, F., et al., "Expression and Characterization of Recombinant Mouse $\beta$2-Microglobulin Type A in Insect Cells Infected with Recombinant Baculoviruses", Res. Immunol. 142, 409-416, 1991.
Godeau, F., et al., "Purification and Ligand Binding of a Soluble Class I Major Histocompatibility Complex Molecule Consisting of the First Three Domains of H-2Kd Fused to $\beta$2-Microglobulin Expressed in the Baculovirus-Insect Cell System", J. of Biological Chem., vol. 267, No. 34, Dec. 5, 1992, pp. 24223-24229.

(56) References Cited

OTHER PUBLICATIONS

Ho et al, "Adoptive therapy with CD8+ T cells: it may get by with a little help from its friends", Journal of Clinical Investigation (2002) 110(10): 1415-1417.
Hom, Sophia et al, "Common expression of melanoma tumor-associated antigens recognized by human tumor infiltrating lymphocytes: Analysis by Human Lymphocyte antigen Restriction", Journal of Immunol. 10:153-164, 1991.
Hortsch M., et al, "Sticky molecules in not-so sticky cells", TIBS 16—Aug. 1991, pp. 283-287.
Huang,et al, "TCR-mediated internalization of peptide-MHC complexes acquired by T cells," Science, Oct. 1999, 286(5441), 952-954.
Ioannides Constantin et al, "T-Cell recognition of oncogene products: A new strategy for Immunotherapy", Molecular Carcinogenesis; 6:77-82 (1992).
Jackson et al, Empty and peptide-containing conformers of class I major histocompatibility complex molecules expressed in *Drosophila melanogaster* cells, Proceedings of the National Academy of Sciences USA 89:12117-12121 1992.
Kawakami, Y. et al, "T-cell recognition of human melanoma antigens", Journal of Immunology. 14:88-93, 1993.
Kluger, Harriet, et al., "Her2/neu is not a commonly expressed therapeutic target in melanoma—a large cohort tissue microarray study", Melanoma Research 2004, 14:207-210.
Lanzavecchia, A., "License to Kill", Nature 1998, 393:413.
Levy et al., "Co-expression of the Human HLA-B27 Class I Antigen and the E3/19K Protein of Adenovirus-2 in Insect Cells using a Baculovirus Vector", Int. Immunol., vol. 2, No. 10, pp. 995-1002, 1990.
Luxembourg, Alain, et al., "Biomagnetic Isolation of Antigen-Specific CD8+T Cells Usable in Immunotherapy", Nature Biotechnology, vol. 16, Mar. 1998, pp. 281-285.
Matsumura, M. et al., In vitro peptide binding to soluble empty class I major histocompatibility complex molecules isolated from transfected *Drosophila melanogaster* Cells., Journal of Biol. Chem., vol. 267, No. 33, 23589-23595, 1992.
Maziarz et al, "Co-expression after Gene Transfer of Human HLA Heavy Chain and Human β2-Microglobulin in Mouse L Cells", Regulation of the Immune System: Abstract # 0336, Proceedings of the Dana-Farber Cancer Institute, Boston, MA 1983.
Mescher, Matthew, "Molecular Interactions in the Activation of Effector and Precursor Cytotoxic T Lymphocytes", Immunol. Review, 1995, No. 146, pp. 177-210.
Nepom, J. T., Acquisition of Syngeneic I-A Determinants by T Cells Proliferating in Response to Poly (Glu60 Ala30 Tyr10), J. of Immunol. vol. 127, pp. 888-892 Sep. 1981.
Noelle, R. et al. "Cognate Interactions between Helper T Cells and B Cells", Immunology Today, vol. 11, No. 10, 1990, pp. 361-368.
Nordon et al, "Ex Vivo Cell Therapy", Academic Press: San Diego, Chapter 11:215-243 1999.
Osband et al, "Problems in the Investigational Study and Clinical Use of Cancer Immunotherapy", Immunol. Today, vol. 11, No. 6, 1990: pp. 193-195.
Penninger et al., "The Actin Cytoskeleton and Lymphocyte Activation", Cell, vol. 96, 9-12, Jan. 8, 1999.
Preckel et al., "Altered Hapten Ligands Antagonize Trinitrophenyl-Specific Cytotoxic T Cells and Block Internalization of Hapten-Specific receptors", J. Exp. Med, vol. 185, No. 10, May 19, 1997 pp. 1803-1813.
Riddel et al., "Principles for Adoptive T Cell Therapy of Human Viral Diseases", Annu. Rev. Immunol. 1995, 13:545-86.
Riddel et al. "Therapeutic reconstitution of Human Viral Immunity by Adoptive Transfer of Cytotoxic T Lymphocyte Clones", Current Topics in Microbiol. and Immuol., vol. 189, 1994 pp. 9-34.
Rivoltini, L. et al, "Induction of tumor-reactive CTL from peripheral blood and tumor-infiltrating lymphocytes of melanoma patients by in vitro stimulation with an immunodominant peptide of the human melanoma antigen MART-1", J. of Immunol. 1995, vol. 154: pp. 2257-2265.
Rosenberg, S. et al, "Use of tumor-infiltrating lymphocytes and interleukin-2 in the immunotherapy of patients with metastatic Melanoma", New England Journal of Medicine, Dec. 22, 1988, pp. 1676-1680.
Schumacher et al. "Peptide Selection by MHC Class I Molecules", Nature, vol. 350, Apr. 25, 1991, pp. 703-706.
Schwartz, Ronald, "Costimulation of T Lymphocytes: the Role of CD28, CTLA-4, and B7/BB1 in Interleukin-2 Production and Immunotherapy", Cell, vol. 71, 1065-1068, Dec. 1992.
Storkus, W. et al, "Identification of human melanoma peptides recognized by class I restricted tumor infiltrating T lymphocytes", Journal of Immunology, vol. 151, 3719-3727, No. 7, Oct. 1, 1993.
Schultze J.L. et al, "Autologous tumor infiltrating T cells cytotoxic for follicular lymphoma cells can be expanded in vitro", Blood May 1997, vol. 89, No. 10 pp. 3806-3816.
Sykulev Y. et al., "High-Affinity Reactions between Antigen-specific T-Cell Receptors and Peptides Associated with Allogeneic and Syngeneic Major Histocompatibiliy Complex Class I Proteins", Proc. Natl Acad. Sci., vol. 91, pp. 11487-11491, Nov. 1994.
Sparano, J.A. et al, "Randomized phase III trial of treatment with High-dose interleukin-2 either alone or in combination with interferon alfa-2a in patients with advanced melanoma", J. Clin. Oncol, vol. 11, No. 10, Oct. 1993, pp. 1969-1977.
Sprent et al., "Constructing Artificial Antigen-Presenting Cells from *Drosophila* Cells", Journal of Advances in Experimental Medicine and Biology, vol. 41, pp. 249-254, 1997.
Stryhn, A., et al., "Preformed Purified Peptide-Major Histocompatibility Class I Complexes are Potent Stimulators of Class I-Restricted T Cell Hybridomas", Eur. J. Immunol. 1994. 24:1404-1409.
Swain, S. et al., "Transforming Growth Factor-β and IL-4 Cause Helper T Cell Precursors to Develop into Distinct Effector Helper Cells that Differ in Lymphokine Secretion Pattern and Cell Surface Phenotype", J. of Immunology, vol. 147, 2991-3000, No. 9 Nov. 1, 1991.
Tureci, O., et al, "Identification of a Meiosis-Specific Protein as a Member of the Class of Cancer/Testis Antigens", Proc. Natl. Acad. Sci. vol. 95, pp. 5211-5216, Apr. 1998.
Udaka, K. et al, "Self-MHC Restricted Peptides Recognized by an Alloreactive T Lymphocyte Clone", J. of Immunology, 1996, 157:670-678.
Weber, S., et al, "Specific Low-Affinity Recognition of Major Histocompatibility Complex Plus Peptide by Soluble T-Cell Receptor", Nature, vol. 356, Apr. 30, 1992, pp. 793-796.
Wentworth et al., "In Vitro Induction of Primary, Antigen-Specific CTL from Human Peripheral Blood Mononuclear Cells Stimulated with Synthetic Peptides", Mol. Immunol., vol. 32, No. 9 pp. 603-612, 1995.
Whiteside, T. L, et al "Generation and characterization of ex vivo propagated autologous CD8+Cells Used for Adoptive Immunotherapy of patients infected with human immunodeficiency virus", Blood, vol. 81, No. 8 Apr. 15, 1993: pp. 2085-2092.
Wolfel, T. et al, Analysis of antigens recognized on human melanoma cells by A2-restricted cytolytic T lymphocytes (CTL): Int. J. Cancer: 55, 237-244 (1993).
Wolfel, T. et al, Isolation of Naturally Processed Peptides Recognized by Cytolytic T Lymphocytes (CTL) on Human Melanoma Cells in Association with HLA-A2.1, Int. J. Cancer: 57, 413-418 (1994).
Yang et al, "Major Histocompatibility Complex (MHC)-encoded HAM2 is Necessary for Antigenic Peptide Loading onto Class I MHC Molecules", J. Of Biol. Chem., vol. 267, No. 17, Jun. 15, 1992, pp. 11669-11672.
Zeiling, Cai, "Transfected *Drosophila* Cells as a Probe for Defining the Minimal Requirements for Stimulating Unprimed CD8+ T Cells", Proc. Natl. Acad. Sci. U.S.A., vol. 93, pp. 14736-14741, Dec. 1996, Immunology.
Zhang, Xiaohong et al, "Control of CD4 Effector Fate: Transforming Growth Factor β1 and Interleukin 2 Synergize to Prevent Apoptosis and Promote Effector Expansion", J. Exp. Med, vol. 182, Sep. 1995, 699-709.
Richards et al, "Therapeutic and Immunologic Evaluation of Autologous CTL Generated Using Transgenic *Drosphila* Cells as APC's for the Treatment of Melanoma", Amer. Soc. Clin Oncol. 20 Abstract 1015, pp. 254A (May 2001).

(56) References Cited

OTHER PUBLICATIONS

Celis E., et al, Induction of Anti-tumor Cytotoxic T Lymphocytes in Normal Humans Using Primary Cultures and Synthetic Peptide Epitopes, PNA, vol. 91, pp. 2105-2109 (Mar. 15, 1994).

European Search Report for EP14187466 dated Feb. 3, 2015.

Gong et al., "Induction of Antitumor Activity by Immunization with Fusions of Dendritic and Carcinoma Cells", Nature Medicine, Nature Publishing Group, New York, NY, US, vol. 3, No. 5, pp. 558-561, May 1, 1997.

Uwe Trefzer et al., Hybrid cell vaccination for cancer immune therapy: First clinical trial with metastatic melanoma:, International Journal of Cancer, vol. 85, No. 1, p. 618, Mar. 1, 2000.

Hans W Nijman et al., "Identification of peptide sequences that potentially trigger HLA-A2.1-restricted cytotoxic T lymphocytes", Eur. J. Immunol., vol. 23, pp. 1215-1219, Jan. 1, 1993.

Brossart Peter, et al., "Induction of cytotoxic T-lymphocyte responses in vivo after vaccinations with peptide-pulsed dendritic cells", Blood, American Society of Hematology, US, vol. 96, No. 9, pp. 3102-3108, Nov. 1, 2000.

\* cited by examiner

Figure 2
Panel A
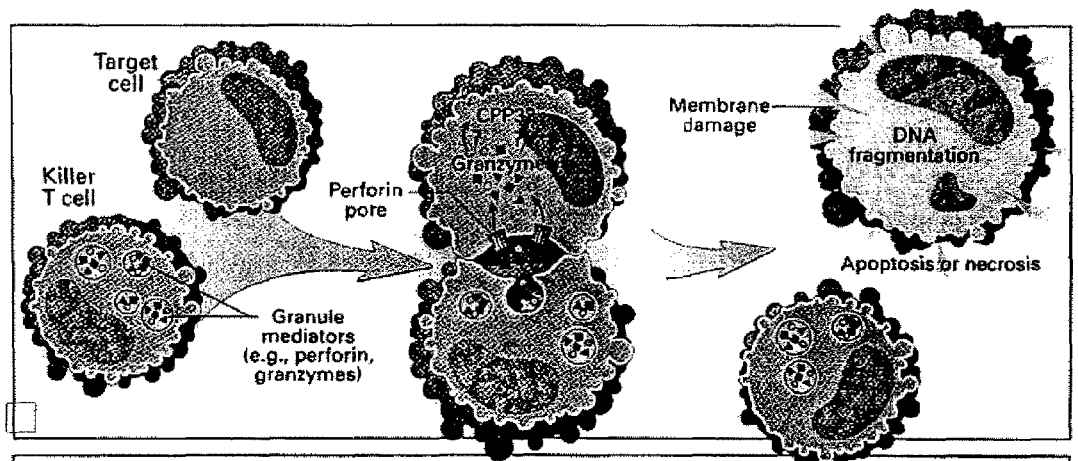
Panel B
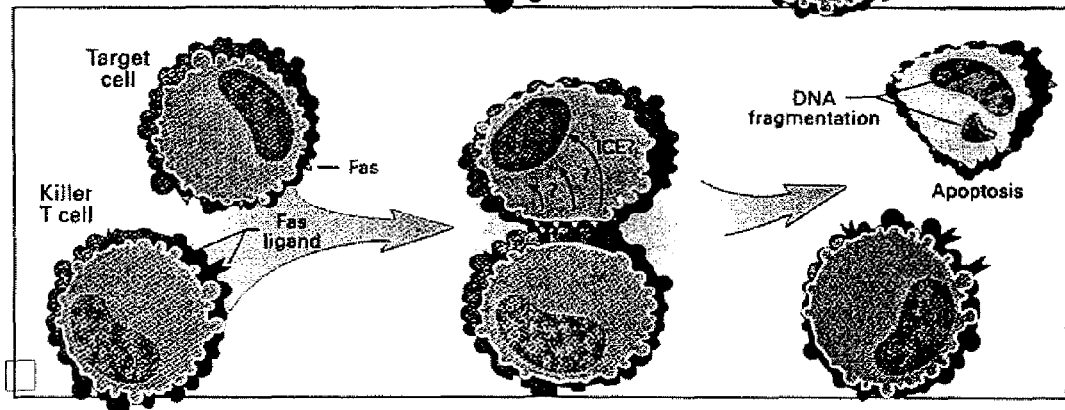

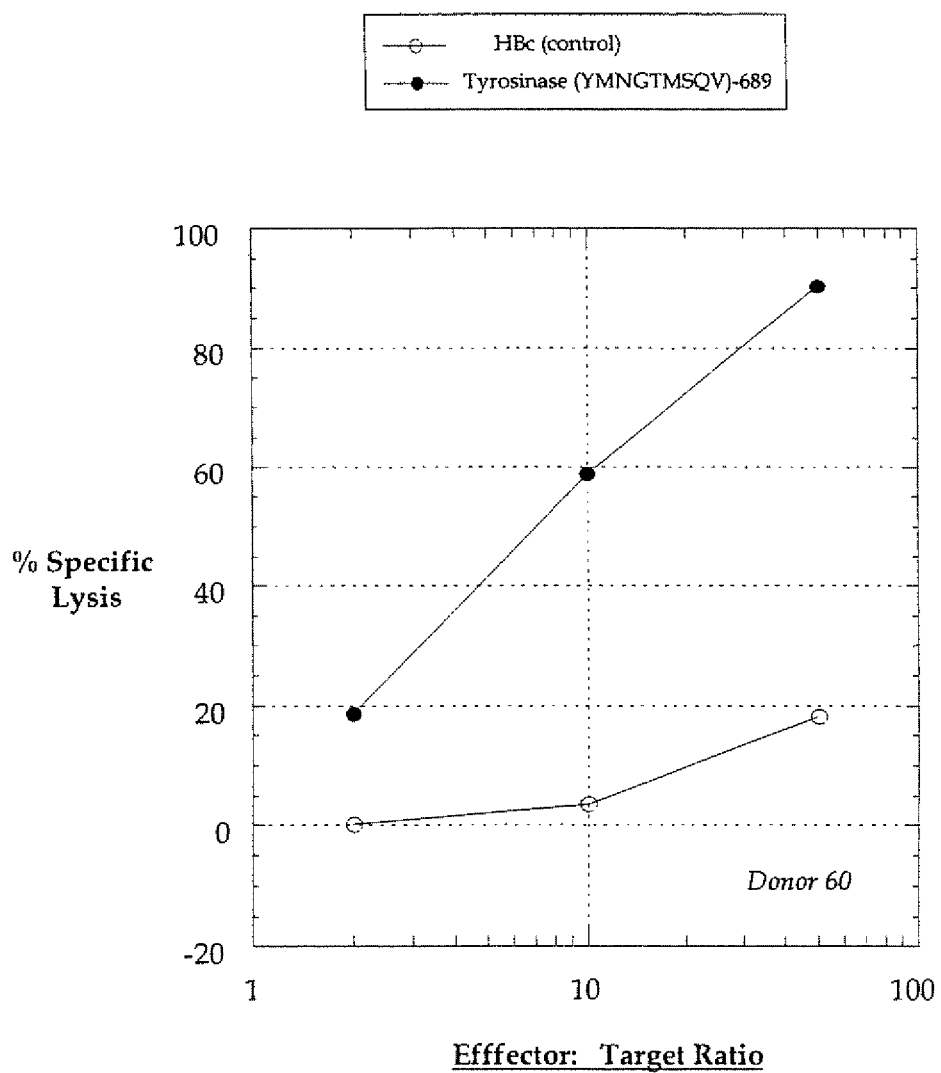

Panel B

Panel C

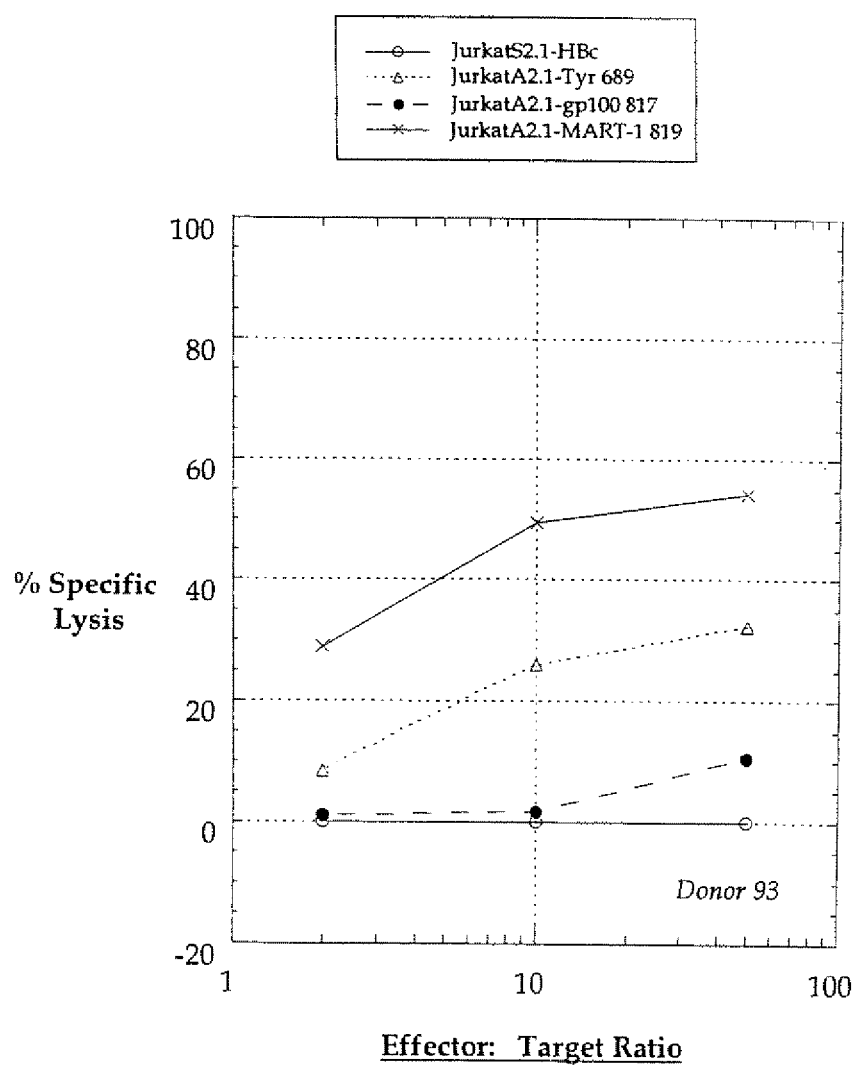

Panel B

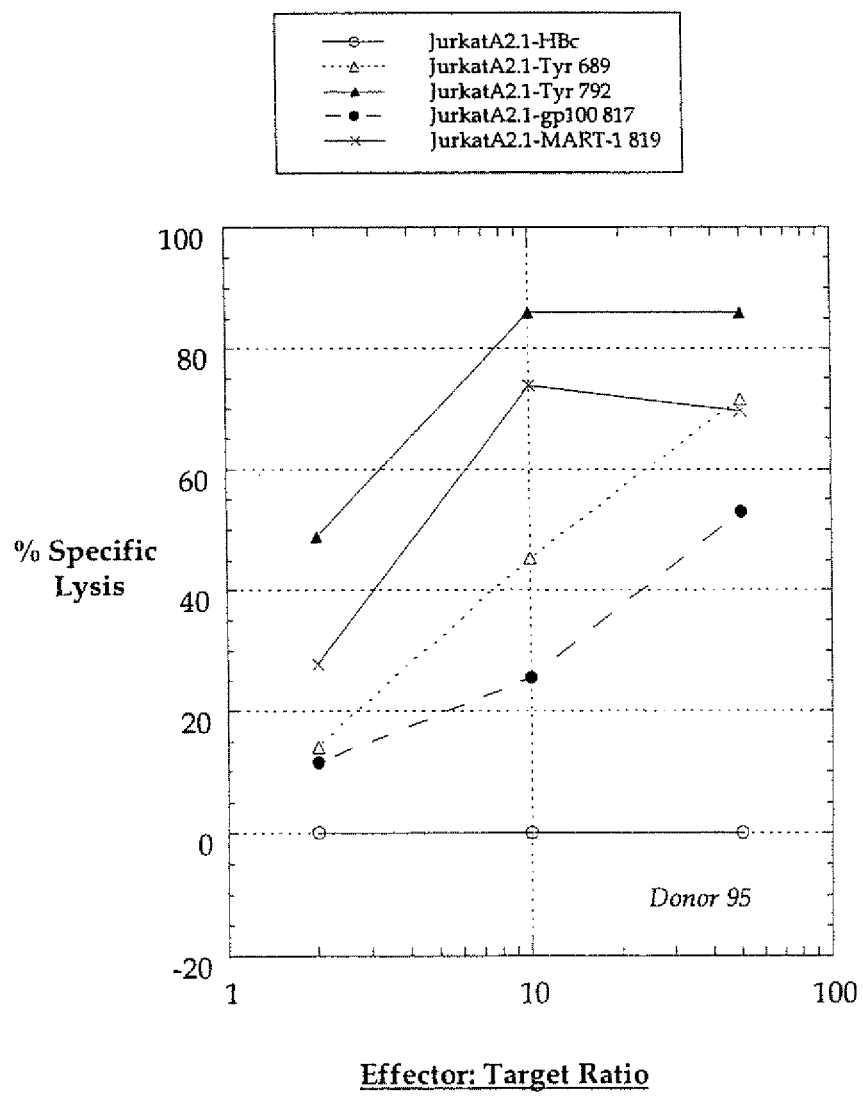

Panel A

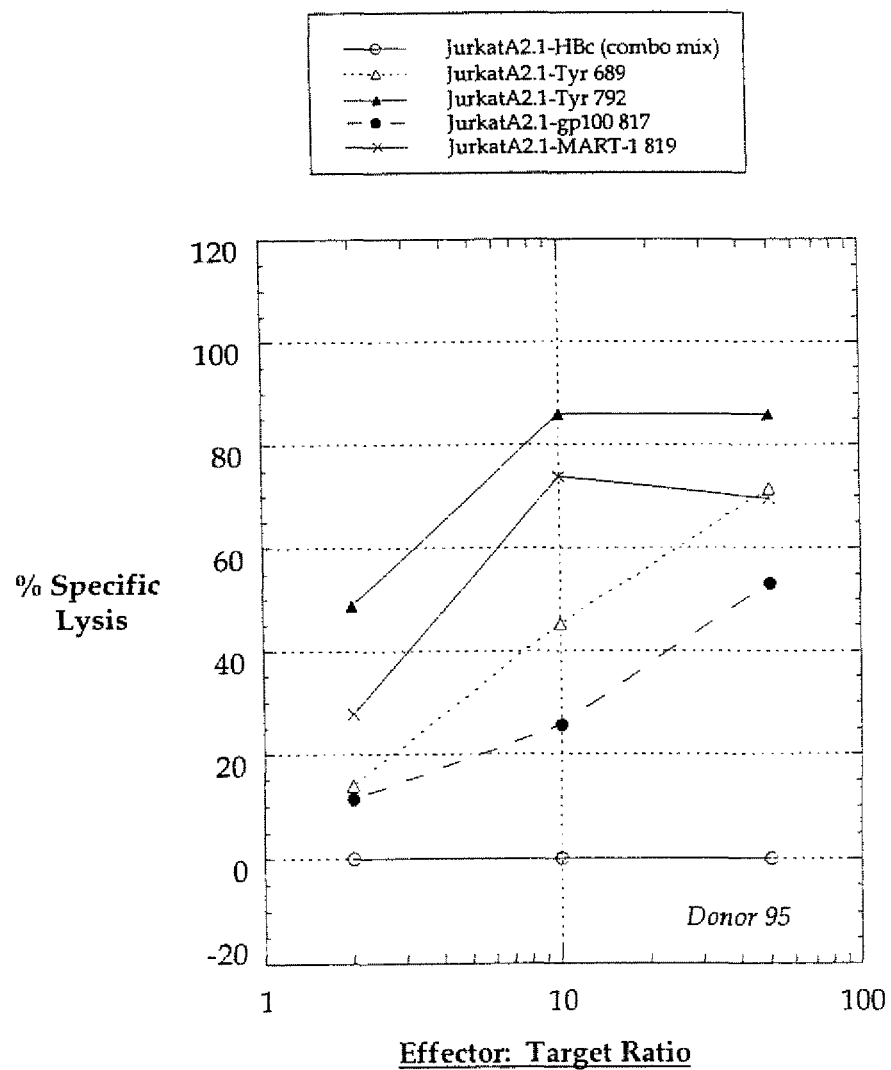

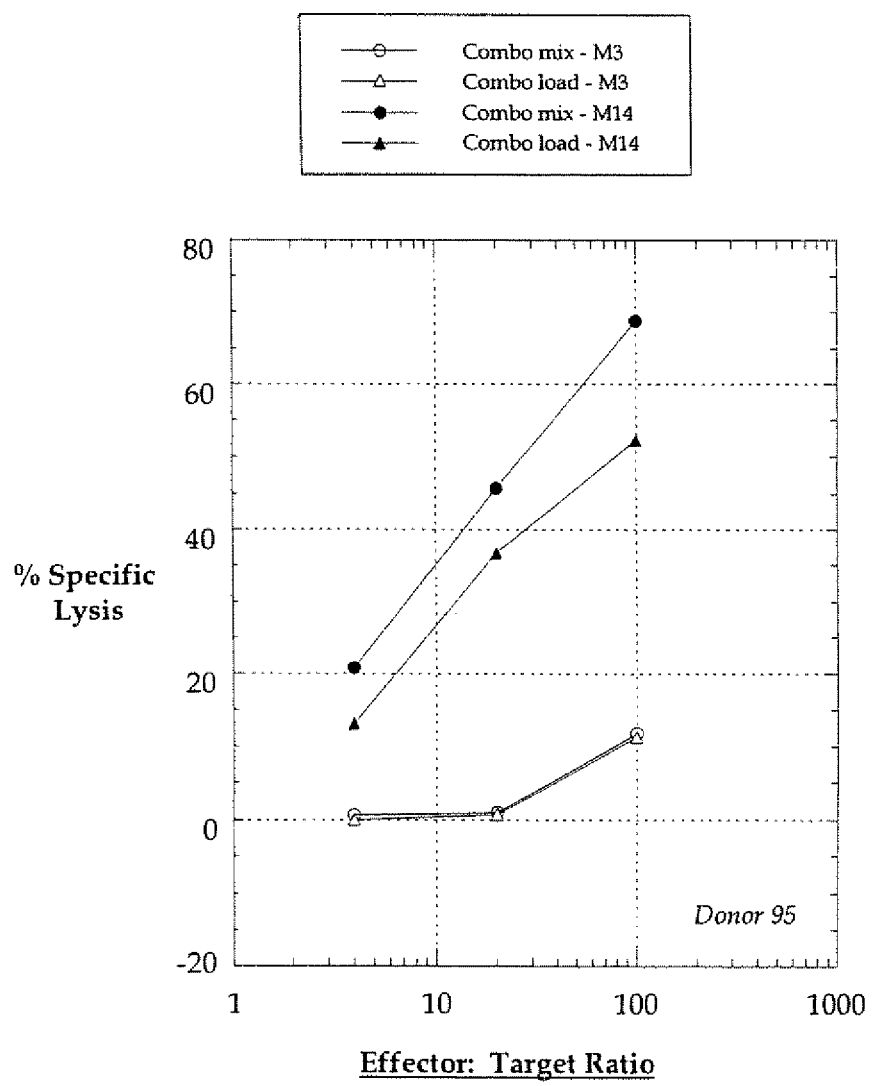

Figure 7
Panel A
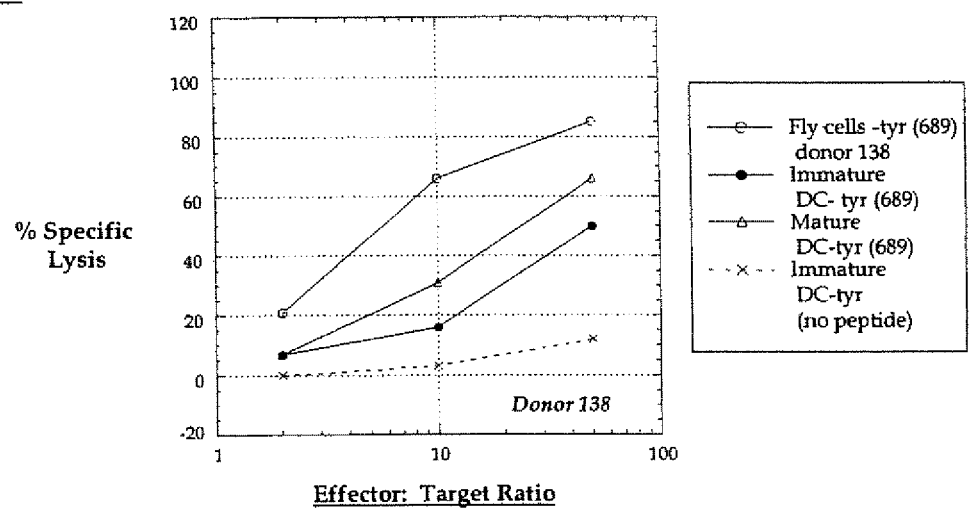
Donor 138
Panel B
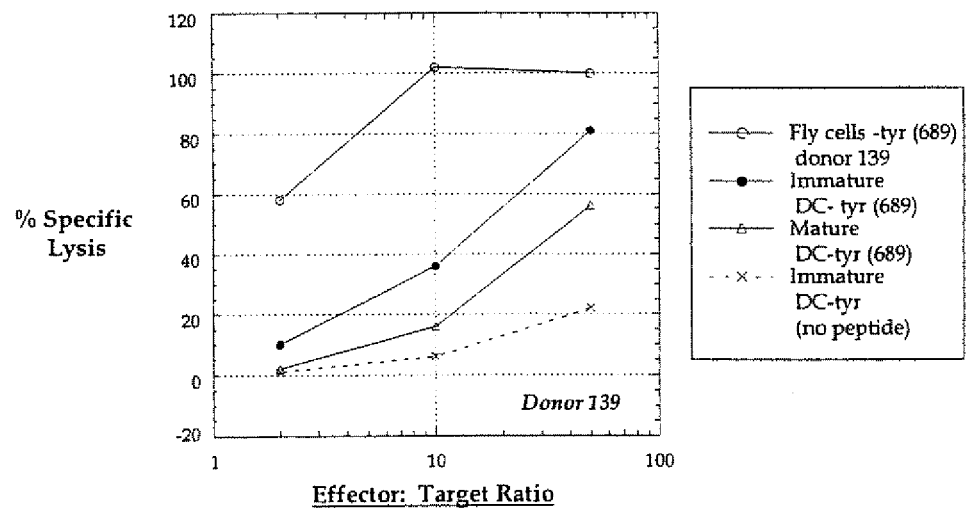
Donor 139

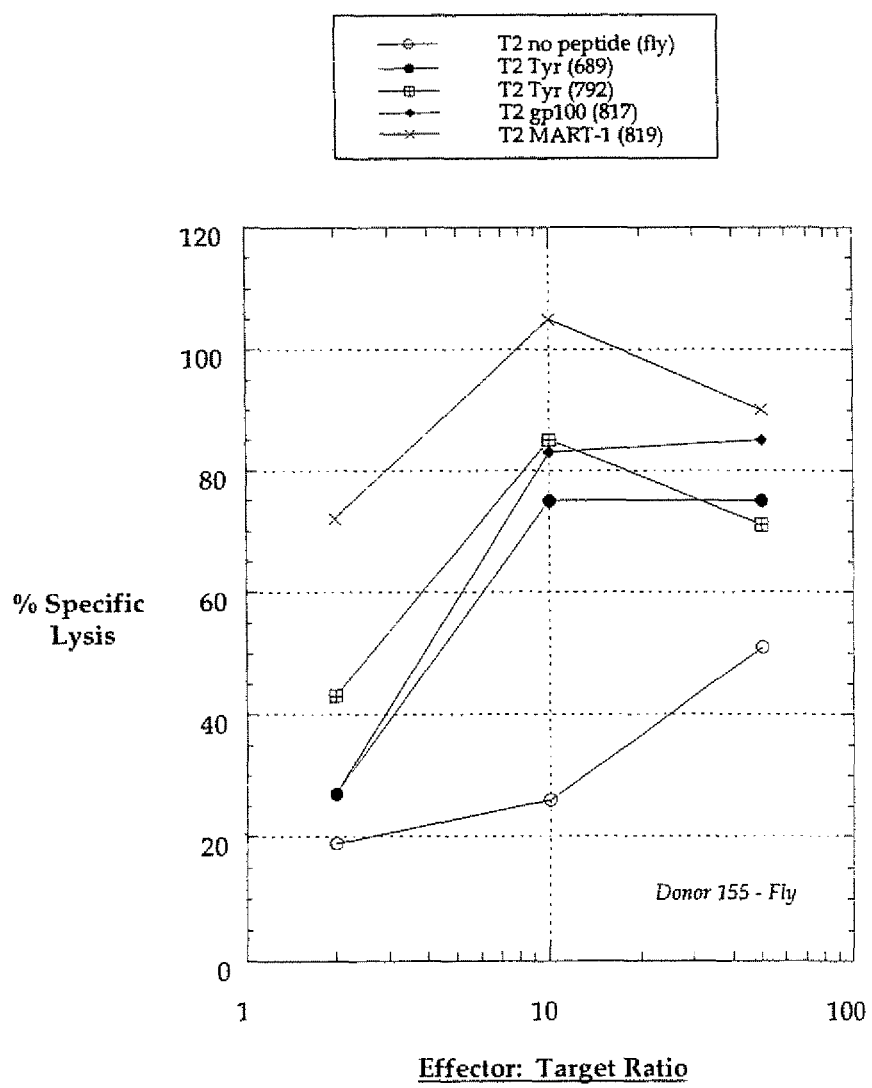

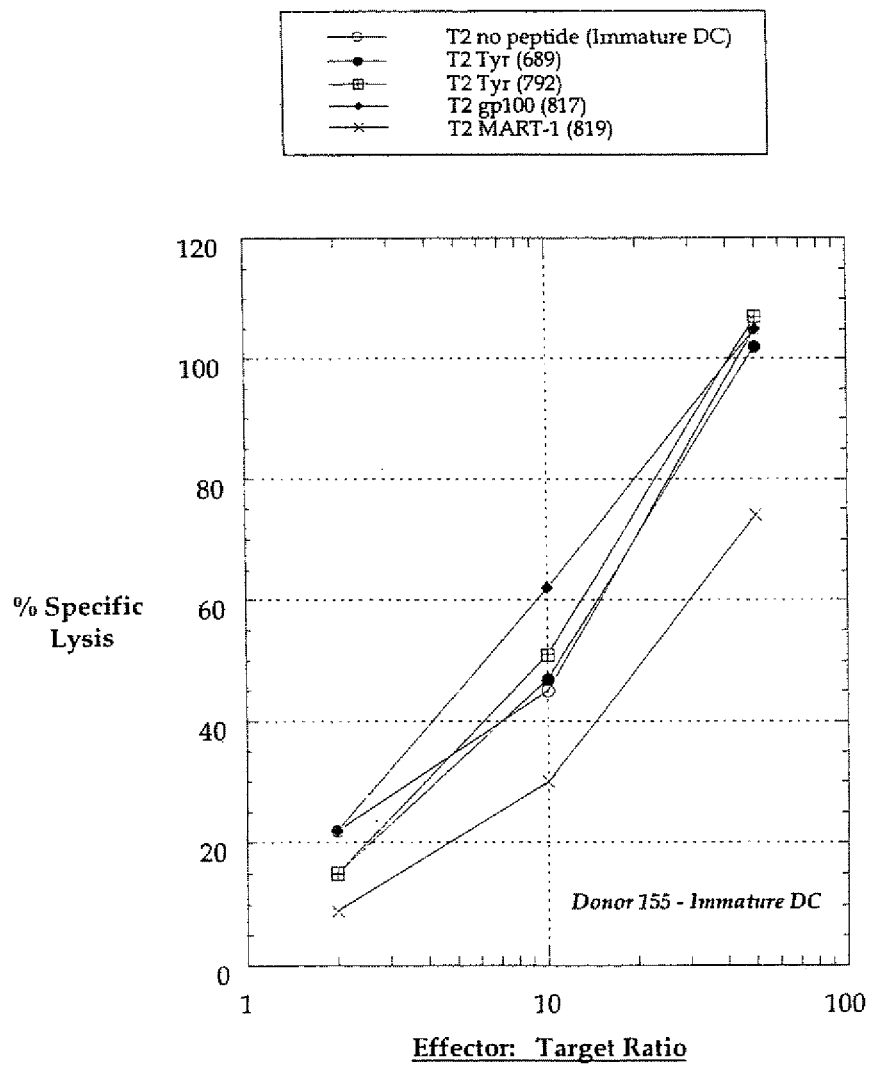

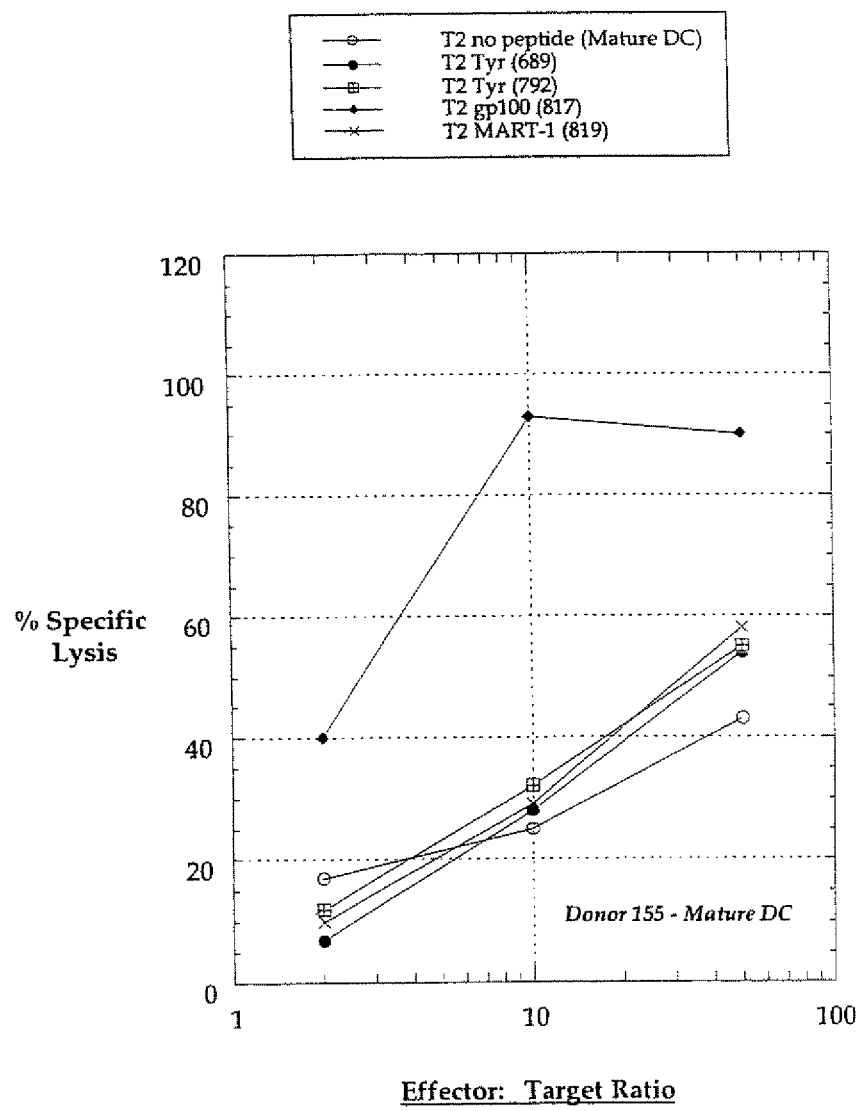

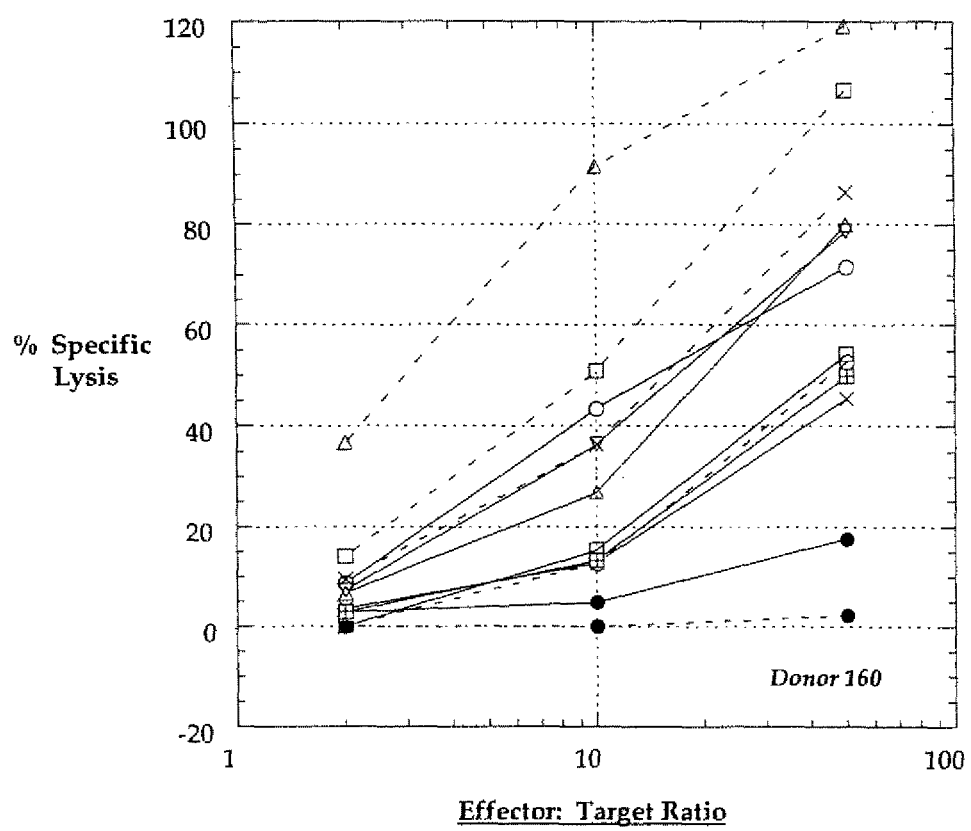

Panel A

Panel B

Figure 15
Panel A
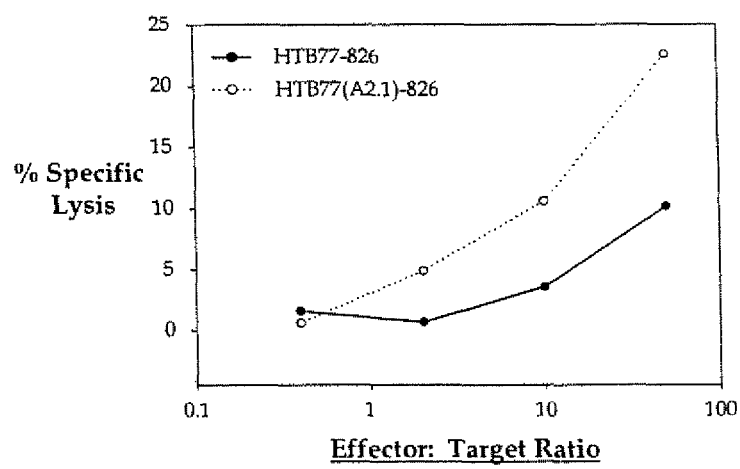
Panel B
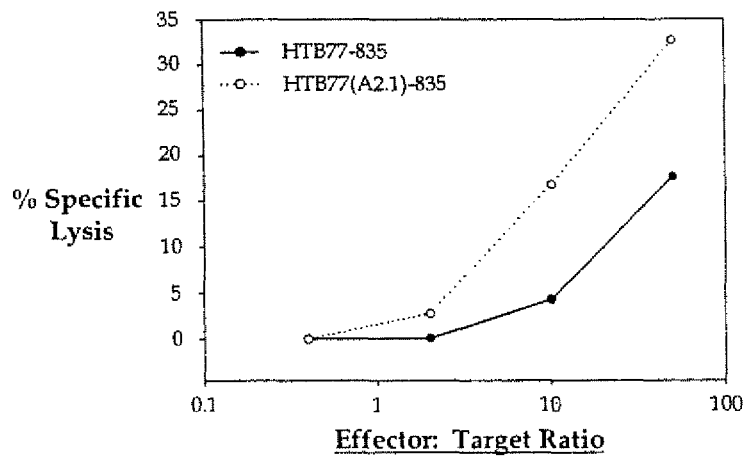

Figure 15
Panel C
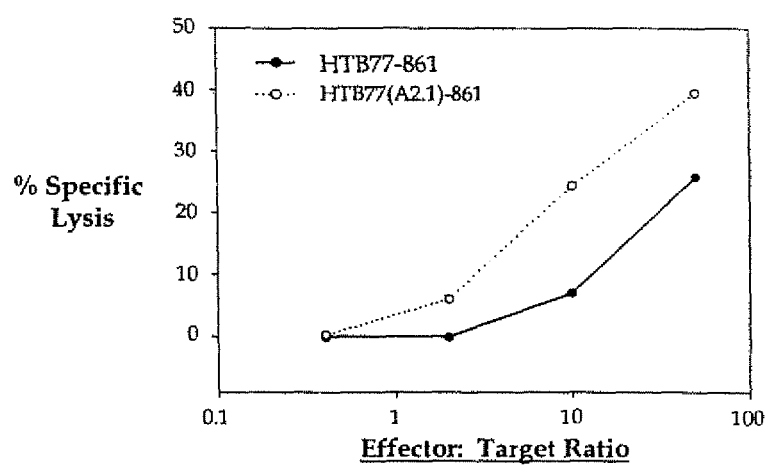
Panel D
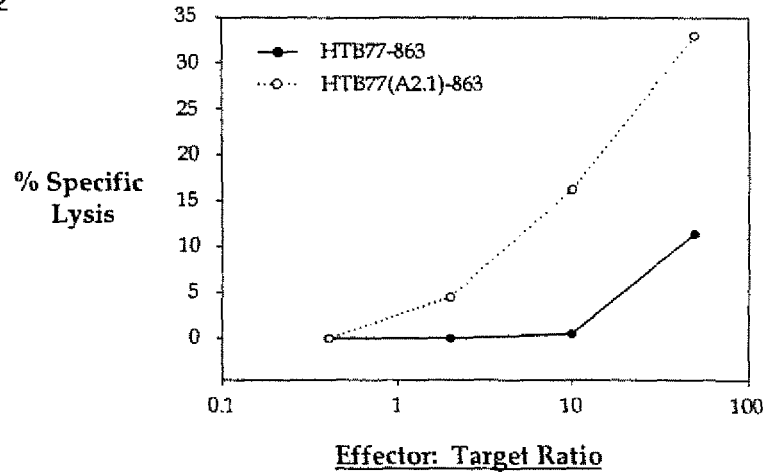

Figure 18
Panel A
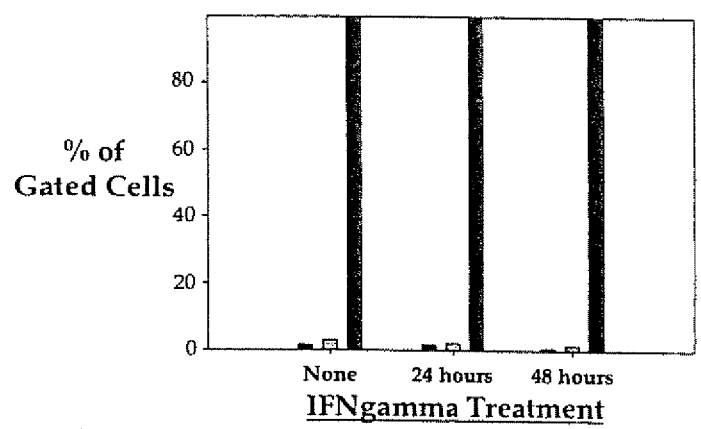
Panel B
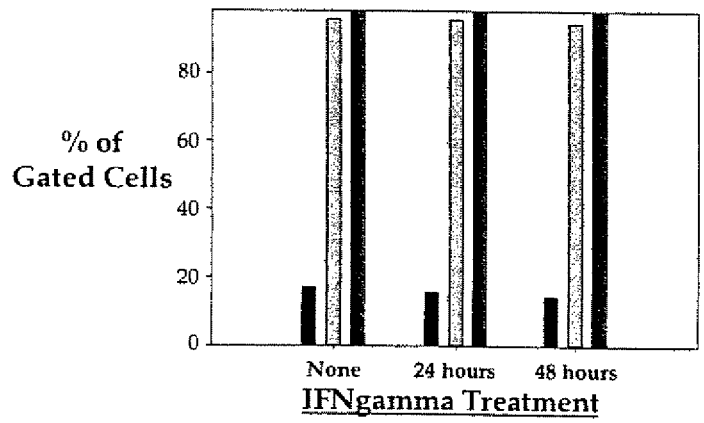
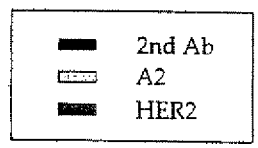

SEQUENCE LISTING

<160> NUMBER OF SEQ ID NOS: 42

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Tyr Met Asn Gly Thr Met Ser Gln Val
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Tyr Met Asp Gly Thr Met Ser Gln Val
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Phe Leu Pro Trp His Arg Leu Phe Leu Leu
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Ile Thr Asp Gln Val Pro Phe Ser Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Lys Thr Trp Gly Gln Tyr Trp Gln Val
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Ala Ala Gly Ile Gly Ile Leu Thr Val
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Cys Leu Thr Ser Thr Val Gln Leu Val
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Lys Ile Phe Gly Ser Leu Ala Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Lys Met Ala Ser Arg Ser Met Arg Leu
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Ala Leu Ala Leu Ala Ala Leu Leu Val Val
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Ala Leu Leu Val Val Asp Arg Glu Val
1               5

<210> SEQ ID NO 12
<211> LENGTH: 12
<212> TYPE: PRT
<213> ORGANISM: Artificial Sequence
<220> FEATURE:
<223> OTHER INFORMATION: Synthetic Construct

<400> SEQUENCE: 12

Ala Ala Glu Gly Leu Asp Thr Gln Arg Phe Ser Gly
1               5                   10

```
<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

His Leu Tyr Gln Gly Cys Gln Val Val
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Ile Ile Ser Ala Val Val Gly Ile Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Pro Leu Thr Ser Ile Ile Ser Ala Val
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Val Met Ala Gly Val Gly Ser Pro Tyr Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Val Leu Val Lys Ser Pro Asn His Val
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Glu Leu Val Ser Glu Phe Ser Arg Met
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Gly Pro Leu Thr Pro Leu Pro Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Ser Thr Ala Pro Val His Asn Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Tyr Leu Ser Gly Ala Asn Leu Asn Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Glu Ile Trp Thr His Ser Tyr Lys Val
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Ser Ile Leu Ser Leu Lys Glu Ala Ser Thr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Ser Leu Leu Met Trp Ile Thr Gln Cys
1               5

<210> SEQ ID NO 25
```

<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Ser Leu Leu Met Trp Ile Thr Gln Val
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Leu Ser Leu Leu Met Trp Ile Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Tyr Leu Glu Thr Phe Arg Glu Gln Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Val Leu Leu Lys Leu Arg Arg Pro Val
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Gly Leu Gln Ser Pro Lys Ser Pro Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Glu Leu Tyr Ile Pro Ser Val Asp Leu
1               5

<210> SEQ ID NO 31
<211> LENGTH: 9

<212> TYPE: PRT
<213> ORGANISM: Artificial Sequence
<220> FEATURE:
<223> OTHER INFORMATION: Synthetic Construct

<400> SEQUENCE: 31

Lys Ala Leu Phe Ala Gly Pro Pro Val
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Phe Met Trp Gly Asn Leu Thr Leu Ala
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Phe Leu Trp Gly Pro Arg Ala Leu Val
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Ile Leu Ala Lys Phe Leu His Trp Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Arg Leu Val Asp Asp Phe Leu Leu Val
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

His Leu Ser Thr Ala Phe Ala Arg Val
1               5

<210> SEQ ID NO 37
<211> LENGTH: 9
<212> TYPE: PRT

```
<213> ORGANISM: Artificial Sequence
<220> FEATURE:
<223> OTHER INFORMATION: Synthetic Construct

<400> SEQUENCE: 37

Ser Ile Ser Gly Asp Leu His Ile Ile
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Val Ala Ala Ser Val Asp Asn Pro His Val
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Glu Leu Ile Ile Glu Phe Ser Lys Met
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct

<400> SEQUENCE: 40

Cys Leu Thr Ser Thr Val Gln Leu Ile
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Construct

<400> SEQUENCE: 41

Arg Leu Leu Gln Glu Thr Glu Leu Val
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Arg Leu Leu Gln Glu Arg Glu Leu Val
1               5
```

CELL THERAPY METHOD FOR THE TREATMENT OF TUMORS

CROSS REFERENCE TO RELATED APPLICATIONS

This application, which is a continuation of application Ser. No. 10/080,013, filed Feb. 19, 2002 now abandoned, which claims priority to application Ser. No. 60/270,252, filed Feb. 20, 2001, claims priority to both of these applications, the entire contents of which are incorporated herein by reference.

BACKGROUND OF THE INVENTION

Cancer continues to be a major health problem, despite significant progress made in the area of treatment. The standard treatment regimes of chemotherapy, radiation therapy, surgical intervention and combinations of the three, often fail to produce a long lasting cure. In many cases, the cancer patient having undergone the treatment often relapses back to the disease condition after some period of time, further exacerbating the problem, is the severity of these treatment regimes to the patient.

Another factor complicating development of a cancer treatment is that cancers have been found to be caused not by a single biological agent or factor, but rather by a combination of agents and factors. Unlike most medical treatments where a single causative agent or event is the focus of the treatment, cancer therapy requires addressing a plurality of biological factors.

In recent years, research has been directed to developing cancer therapies that utilize the patient's own immune system. One such approach is adoptive immunotherapy. Adoptive immunotherapy calls for using the patient's own cells to generate cytotoxic T lymphocytes (CTLs) to treat a tumor or cancerous cells. However, this technique remains largely unproven as a viable clinical treatment regime for human patients. Aside from the problem of identifying the proper epitopes with which to immunize the CTL's, the current technology does not provide for a method of presenting a sufficient number of different epitopes to APCs in order to adequately target multiple antigens to effectively treat the cancer. The present invention fulfills unmet needs, as well as providing other benefits.

SUMMARY OF THE INVENTION

The present invention provides a non-naturally occurring antigen-presenting cell (nnAPC) capable of presenting up to ten or more different peptides simultaneously methods of manufacturing nnACP, methods of using said nnACP for the treatment of cancer.

BRIEF DESCRIPTION OF THE DRAWINGS

FIG. 2, Panels A and B:
This figure is a two panel graphical depiction of mechanisms of lymphocyte-mediated cytosis.

FIG. 7, Panels A and B:
This figure compares the ability of Drosophila cells versus dendritic cells to elicit CTL responses to a single peptide epitope following standard stimulation protocols.

FIG. 9, Panels A, B and C:
This figure shows CTL activity generated by a single donor to three different in vitro simulation protocols presenting four peptides.

FIG. 10: This figure show CTL activity generated to ten (10) peptides loaded, in combination, to Drosophila cells.

FIG. 15, Panels, A, B, C, D:
This figure demonstrates the enhanced killing of an ovarian tumor cell line (HTB-77) when transfected with HLA-A2.1.

FIG. 18, Panels A and B:
This graph demonstrates that the surface expression of HLA-A2 and HER-2 is unaffected by the IFNγ induction in the two cell lines (HTB-77 and HTB-77/A2.1).

DETAILED DESCRIPTION OF THE INVENTION

Figure 1:
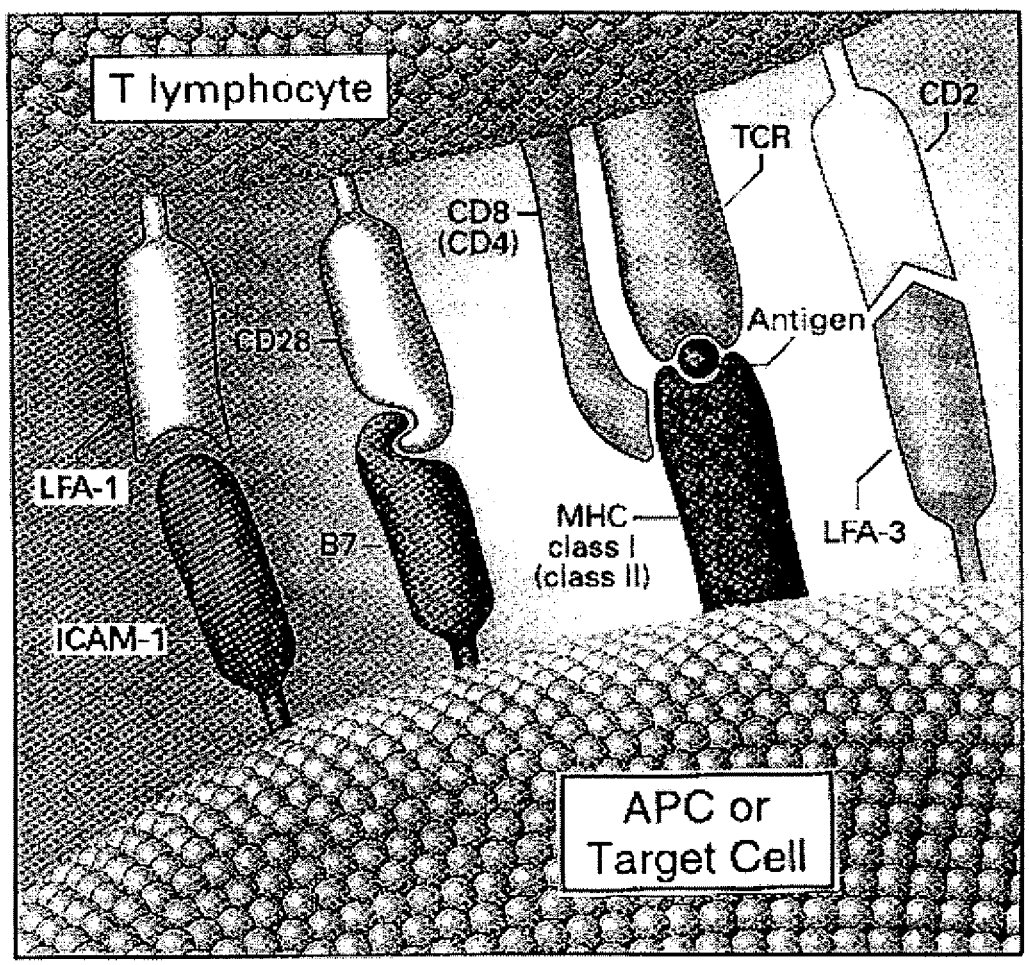
FIG. 1: This figure is a graphic depiction of the interaction between CD8$^+$ cells, also known as cytotoxic T lymphocytes with antigen-presenting cells or target cells, in is case tumor cells.

The present invention provides a method for treating a subject with cancer comprising:
a. preparing a non-naturally occurring antigen-presenting cell line (nnAPC), wherein said n C is capable of presenting up to about fifteen different peptide molecules that is associated with cancer, preferably about ten different peptide molecules, simultaneously where each peptide is about six to twelve amino acids in length, preferably about eight to ten amino acids in length and in a concentration range of about 10 nM to 100 µM;
b. harvesting CD8$^+$ cells from said subject or a suitable donor;
c. stimulating said CD8$^+$ cells with said nnAPC cell line;
d. adding said CD8$^+$ cells to media that contains a cytokine, such as, IL-2, IL-7 or conditioned growth medium (CGM), preferably, IL-2, or IL-2 and IL-7 in combination;
e. mixing unsuspended peripheral blood monocytes, or alternatively, CD-8 depleted peripheral blood monocytes collected from said subject or a suitable donor with about 10 to 50 µg/ml of a peptide;
f. irradiating said peripheral blood monocyte suspension with a sufficient dose of γ-radiation necessary to prevent proliferation of these cells in the suspension, such as a dose in the range of about 3,000 to 7,000 rads, preferably about 5,000 rads, alternatively, the peripheral blood lymphocyte suspension may be treated with cytostatic agents including, but not limited to, mitomycin C;
g. isolating adherent peripheral blood monocytes;
h. loading said adherent peripheral blood monocytes with about 10 ng/ml to 10 µg/ml of said each peptide;
i. combining said CD8$^+$ cells with said adherent peripheral blood monocytes at a ratio of about ten CD8$^+$ cells to one peripheral blood monocyte;
j. optionally stimulating said combined suspension of CD8$^+$ cells and peripheral blood monocytes for about six to seven days;
k. optionally stimulating said suspension of CD8$^+$ cells and peripheral blood monocytes with IL-2 and L-7 in media;
l. optionally assaying CD8$^+$ suspension for suitable CTL activity, and optionally assaying for CTL purity, sterility and endotoxin content; and
m. inoculating said subject with CD8$^+$ suspension.

Another embodiment of the present invention provides a method for treating a subject with cancer comprising:
a. preparing a non-naturally occurring antigen-presenting cell line (nnAPC), wherein said nnAPC is capable of presenting up to about fifteen different peptide molecules that is associated with cancer, preferably about ten peptides, simultaneously where each peptide is eight to ten amino acids in length;
b. harvesting CD8$^+$ cells from said subject;
c. stimulating said CD8$^+$ cells with said nnAPC cell line for about six to seven days;
d. stimulating said CD8$^+$ cells with IL-2 and IL-7 in media;
e. mixing peripheral blood monocytes collected from said subject with about 20 µg/ml of each peptide;
f. irradiating said CD8-depleted peripheral blood monocyte suspension with about 5,000 rads of γ-radiation;
g. isolating adherent peripheral blood monocytes;
h. loading said adherent peripheral blood monocytes with about 10 ug/ml of said epitope;
i. combining said CD8$^+$ cells with said adherent peripheral blood monocytes at a ratio of about ten CD8$^+$ cells to one peripheral blood monocyte; stimulating said combined suspension of CD8$^+$ cells and peripheral blood monocytes for about six to seven days;
k. stimulating said suspension of CD8$^+$ cells and peripheral blood monocytes with IL-2 and IL-7 in media;
l. assaying CD8$^+$ suspension for suitable CTL activity, purity sterility and endotoxin content; and
m. inoculating said subject with CD8$^+$ suspension.

Another embodiment of the present invention provides a method for treating a subject with melanoma comprising:
a. preparing a non-naturally occurring antigen-presenting cell line (nnAPC), wherein said nnAPC is capable of presenting up to about fifteen different peptide molecules that is associated with melanoma, preferably about ten peptides, simultaneously where each peptide is eight to ten amino acids in length;
b. harvesting CD8$^+$ cells from said subject;
c. stimulating said CD8$^+$ cells with said nnAPC cell line for about six to seven days;
d. stimulating said CD8$^+$ cells with IL-2 and IL-7 in media;
e. mixing peripheral blood monocytes collected from said subject with about 20 µg/ml of each peptide said nnAPC can present;
f. irradiating said CD8-depleted peripheral blood monocyte suspension with about 5,000 rads of γ-radiation;
g. isolating adherent peripheral blood monocytes;
h. loading said adherent peripheral blood monocytes with about 10 ug/ml of said epitope;
i. combining said CD8$^+$ cells with said adherent peripheral blood monocytes at a ratio of about ten CD8$^+$ cells to one peripheral blood monocyte;
j. stimulating said combined suspension of CD8$^+$ cells and peripheral blood monocytes for about six to seven days;
k. stimulating said suspension of CD8$^+$ cells and peripheral blood monocytes with IL-2 and IL-7 in media;
l. assaying CD8$^+$ suspension for suitable CTL activity, purity, sterility and endotoxin content; and
m. inoculating said subject with CD8$^+$ suspension.

Another embodiment of the present invention is a method of treating melanoma wherein the nnAPC presents the following peptides, Tyrosinase$_{369-377}$, Tyrosinase$_{207-216}$, gp100$_{209-217}$, gp100$_{154-162}$, MART-1$_{27-35}$, HR-2/neu$_{789-797}$, HER-2/ne$_{369-377}$, C-lec$_{8-16}$, Pec60$_{20-29}$, and Pec60$_{25-33}$.

Another embodiment of the present invention is a method of treating a disease or disease condition that results in an insufficient or inadequate immune response that is normally associated with Class I HLA molecules, wherein the treatment eliminates infected or transformed cells has been demonstrated to be achieved by CTLs.

Another embodiment of the present invention is a method of treating a disease or disease condition that results in an insufficient or inadequate immune response that is normally associated with Class I HLA molecules, wherein infected or transformed cells that have been shown to be susceptible to elimination by CTL are treated by the method comprising:
a. preparing a non-naturally occurring antigen-presenting cell line (nnAPC), wherein said nnAPC is capable of presenting up to about fifteen different peptide molecules that is associated with said disease or disease condition, preferably about ten different peptide molecules, simultaneously where each peptide is about six to twelve amino acids in length, preferably about eight to ten amino acids in length and in a concentration range of about 10 nM to 100 µM;
b. harvesting CD8$^+$ cells from said subject or a suitable donor;
c. stimulating said CD8$^+$ cells with said nnAPC cell line;
d. adding said CD8$^+$ cells to media that contains a cytokine, such as, IL-2, IL-7 or CGM, preferably, IL-2, or IL-2 and IL-7 in combination;
e. mixing unsuspended peripheral blood monocytes, or alternatively, CD-8 depleted peripheral blood monocytes collected from said subject or a suitable donor with about 10 to 50 µg/ml of a peptide;
f. irradiating said peripheral blood monocyte suspension with a sufficient dose of γ-radiation necessary to sterilize all components in the suspension, except the desired peripheral blood monocytes, such as a dose in the range of about 3,000 to 7,000 rads, preferably about 5,000 rads;
g. isolating adherent peripheral blood monocytes;
h. loading said adherent peripheral blood monocytes with about 10 ng/ml to 10 µg/ml of said each peptide;
i. combining said CD8$^+$ cells with said adherent peripheral blood monocytes at a ratio of about ten CD8$^+$ cells to one peripheral blood monocyte;
j. optionally stimulating said combined suspension of CD8$^+$ cells and peripheral blood monocytes for about six to seven days;
k. optionally stimulating said suspension of CD8$^+$ cells and peripheral blood monocytes with IL-2 and IL-7 in media;
l. optionally assaying CD8$^+$ suspension for suitable CTL activity, and optionally assaying for CTL purity, sterility and endotoxin content; and
m. inoculating said subject with CD8$^+$ suspension.

The present invention provides a non-naturally occurring antigen-presenting cell (nnAPC) derived from *Drosophila melanogaster* cells transfected with DNA encoding human class I HLA, binding, and co-stimulatory molecules for expression, wherein the is capable of presenting up to fifteen different peptide molecules, preferably ten peptide molecules.

Another embodiment of the present invention provides a nnAPC that presents peptides that are associated with various desired functions that enhance the treatment of the subject. For example, in addition to peptides associated with the disease or disease condition being treated, the nnAPC can present peptides associated with accessory molecules such as, lymphocyte function antigens (LFA-1, LFA-2 and LFA-3), intercellular adhesion molecule 1 (ICAM-1), T-cell co-stimulatory factors (CD2, CD28, B7) enhance cell-cell adhesion or transduce additional cell activation signals.

Another embodiment of the present invention provides a nnAPC that presents peptides that are associated with several types of cancers. For example, the peptides associated or derived from a breast cancer related polypeptide, such as, HER-2/neu, may be presented with peptides associated or derived from a melanoma related polypeptide, such as, MART-1, or MAGE.

Another embodiment of the present invention provides a method for manufacturing non-naturally occurring antigen-presenting cell (nnAPC) capable of presenting up to ten different peptide molecules simultaneously, said method comprising of the step:

a. preparing an insect cell line from *Drosophila melanogaster* eggs; alternatively preparing an insect cell line for expressing human MHC Class I molecules and costimulatory adhesion molecules;
b. growing said insect cells a media that is suitable for growing insect cells, preferably Schneider™'s *Drosophila* Medium;
c. making a pRmHa-3 plasmid from a pRmHa-1 expression vector, where said pRmHa-3 plasmid includes a metallothionein promoter, metal response consensus sequences and an alcohol dehydrogenase gene bearing a polyadenylation signal isolated from *Drosophila melanogaster*;
d. inserting into said pRmHa-3 plasmid complementary DNA for human class I HLA A2.1, B7.1, B7.2, ICAM-1, β-2 microglobulin and LFA-3, wherein A2.1 can be substituted with any human class I DNA sequence;
e. transfecting said insect cells with a phshneo plasmid and said pRmHa-3 plasmid containing complementary DNA; and,
f. creating nnAPC by contacting said insect cells with CuSO$_4$ to induce expression of the transfected genes in said insect cells.

The insect cells of the present invention are grown in a media suitable for growing insect cells, hereinafter referenced to as "insect growth media". Insect growth media are commercially available from a number of vendors, such as, Schneider™'s *Drosophila* Medium, Grace's Insect Media, and TC-100 Insect Media. Alternatively, insect growth media can be prepared by one of ordinary skill in the art. Typically the media will include components necessary to promote and sustain the growth of insects cells, such as, inorganic salts (for example, calcium chloride, magnesium sulfate, potassium chloride, potassium phosphate, sodium bicarbonate, sodium chloride, and sodium phosphate), amino acids various carbohydrate and chemical species (Imogene Schneider, *Exp. Zool.* (1964) 156(1): pg. 91). Alternatively, the media can also include vitamins, minerals, and other components that aid in the growth of insect cells.

Following is a list of abbreviations and definitions used in the present specification.

Abbreviations

APC Antigen-presenting cells
CD8$^+$ CD8$^+$ T cells
CTL Cytotoxic T lymphocyte
E Effector
Fas Also known as CD95, epitope on T cells
ICAM Intercellular adhesion molecule
IL Interleukin
LAK Lymphokine-activated killer cells
LFA Lymphocyte function antigens
MHC Major histocompatibility complex
nnAPC non-naturally occurring antigen-presenting cell
NP Nuclear protein
PBMC Peripheral blood mononuclear cell
PBS Phosphate-buffered saline
PCR Polymerase chain reaction
RPMI Roswell Park Memorial Institute
RWJPRI The R.W. Johnson Pharmaceutical Research Institute
T Target
TCR T cell antigen receptor
TIL Tumor-infiltrating lymphocytes Following is a list of abbreviations used in the present specification for various peptide epitopes. The individual amino acid residues are identified according to a single letter code that is readily known and used by those of ordinary skill in the art

| | Abbreviations | |
|---|---|---|
| Amino Acid | 3-Letter | 1-Letter |
| alanine | ala | A |
| valine | val | V |
| leucine | leu | L |
| isoleucine | ile | I |
| proline | pro | P |
| phenylalanine | phe | F |
| trytophan | tyr | W |
| methionine | met | M |
| glycine | gly | G |
| serine | ser | S |
| threonine | thr | T |
| cysteine | cys | C |
| tyrosine | tyr | Y |
| asparagine | asn | N |
| glutamine | gln | Q |
| aspartic acid | asp | D |
| glutamic acid | glu | E |
| lysine | lys | K |
| arginine | arg | R |
| histidine | his | H |

Peptide Epitope Abbreviations

As used herein the term "tyrosinase 369-377" or "tyrosinase$_{369-377}$" refers to the amino acid sequence YMNGTMSQV (SEQ ID NO:1). Also included within this definition is the peptide of the sequence YMDGTMSQV (SEQ ID NO: 2), which results from a post-translational event that modifies the amino acid residue "N" of sequence YMNGTMSQV (SEQ ID NO:1) to "D" resting in the amino acid sequence of YMDGTMSQV (SEQ ID NO. 2) (Skipper et al., *J. Exp. Med.* (1996) 183:527-534).

As used herein the term "tyrosinase 207-216" or "tyrosinase$_{207-216}$" refers to the amino acid sequence FLPWHRLFLL (SEQ ID NO: 3).

As used herein the term "gp100 209-217" or "gp100$_{209-217}$" refers to the amino acid sequence ITDQVPFSV (SEQ ID NO: 4).

As used herein the term "gp100 154-162" or "gp100$_{154-162}$" refers to the amino acid sequence KTWGQYWQV (SEQ ID NO: 5).

As used herein the term "MART-1 27-35" or "MART-1$_{27-35}$" refers to the amino acid sequence AAGIGILTV (SEQ ID NO: 6).

As used herein the term "HER-2/neu 789-797" or "HER-2/neu$_{789-797}$" refers to the amino acid sequence CLTSTVQLV (SEQ ID NO: 7).

As used herein the term "HER-2/neu 369-377" or "HER-2/neu$_{369-377}$" refers to the amino acid sequence KIFGSLAFL (SEQ ID NO: 8).

As used herein the term "C-lectin 8-16" or "C-lectin$_{8-16}$" refers to the amino acid sequence KMASRSMRL (SEQ ID NO: 9).

As used herein the term "Pec60 20-29" or "Pec60$_{20-29}$" refers to the amino acid sequence ALALAALLVV (SEQ ID NO: 10).

As used herein the term "Pec60 25-33" or "Pec60$_{25-33}$" refers to the amino add sequence ALLVVDREV (SEQ ID NO:11).

As used herein, the term "CD8 peptide 59-70" or "CD8 peptide$_{59-70}$" refers to the amino acid sequence of AAEGLDTQRFSG (SEQ ID NO: 12).

Terms and Definitions

As used herein, the term "adoptive immunotherapy" refers the administration of donor or autologous T lymphocytes for the treatment of a disease or disease condition, wherein the disease or disease condition results in an insufficient or inadequate immune response that is (normally associated with Class I HLA molecules. Adoptive immunotherapy is an appropriate treatment for any disease or disease condition where the elation of infected or transformed cells has been demonstrated to be achieved by CTLs. For example, disease or disease conditions include but are not limited to cancer and/or tumors, such as, melanoma, prostate, breast, colorectal stomach, throat and neck, pancreatic, cervical ovarian, bone, leukemia and lung cancer; viral infections, such as, hepatitis B, hepatitis C, human immunodeficiency virus; bacterial infections, such as tuberculosis, leprosy and listeriosis, and paracytic infections such as malaria.

As used herein, the term "B7.1" refers to a co-stimulatory molecule associated with antigen-presenting cells.

As used herein, the term "BCNU" refers to carmustine, also known as, 1,3-bis(2chloroethyl)-1-nitrosourea.

As used herein, the term "BSE" refers to bovine spongiform encephaitis.

As used herein, the term "CD" refers to clusters of differentiation, T lymphocytes (originally), B lymphocytes, monocytes, macrophages, and granulocytes grouped by antigen epitopes and function.

As used herein, the term "DTIC" refers to dacarbazine, 5-(3,3-dimethyl-1-triazeno)-imidazole-4-carboxamide.

As used herein, the term "ex vivo" or "ex vivo therapy" refers to a therapy where biological materials, typically cells, are obtained from a patient or a suitable alternate source, such as, a suitable donor, and are modified, such that the modified cells can be used to treat a pathological condition which be improved by the long-term or constant delivery of the therapeutic benefit produced by the modified cells. Treatment includes the re-introduction of the modified biological materials, obtained from either the patient or from the alternate source, into the patient. A benefit of ex vivo therapy is the ability to provide the patient the benefit of the treatment, without exposing the patient to undesired collateral effects from the treatment. For example, cytokines are often administered to patients with cancer or viral infections to stimulate expansion of the patient's CTLs. However, cytokines often cause the onset of flu like symptoms in the patients. In an ex vivo procedure, cytokines are used to stimulate expansion of the CTLs outside of the patient's body, and the patient is spared the exposure and the consequent side effects of the cytokines. Alternatively under suitable situations, or conditions, where appropriate and where the subject can derive benefit, the subject can be treated concurrently with low level dosages of γ interferon, a interferon and/or IL-2. The expected effect of the interferons is to possibly sensitize the tumor cells to lysis by antigen specific CTL, and the effect of the IL-2 is to possibly enhance antigen specific CTL persistence.

As used herein, the term "HEPES" refers to N-2-hydroxyethlpiperazine-N'2-ethanesulfonic acid buffer.

As used herein, the term "HLA-A2.1" refers to a HLA Class I molecule found in approximately 45% of Caucasians.

As used herein, the term "MART-1" or "(melanoma antigen recognized by T-Cell-1" refers to a melanoma-associated antigen. The amino acid and nucleic acid sequences, as well as various characteristics of this antigen are disclosed in U.S. Pat. No. 5,994,523, issued Nov. 30, 1999 entitled "Melanoma Antigens and Their Use in Diagnostic and Therapeutic Methods"; U.S. Pat. No. 5,874,560, issued Feb. 23, 1999 entitled "Melanoma Antigens and Their Use in Diagnostic and Therapeutic Methods"; and U.S. Pat. No. 5,844,075, issued Dec. 1, 1998 entitled "Melanoma Antigens and Their Use in Diagnostic and Therapeutic Methods." In particular, U.S. Pat. No. 5,994,523 discloses full length nucleic acid and amino acid sequences of MART-1 in FIG. 1 as SEQ ID NO: 1, and SEQ ID NO: 2, respectively. The aforementioned FIG. 1 is herein incorporated by reference.

As used herein, the term "MAGE" refers to a melanoma-associated antigen. The amino acid and nucleic acid sequences, as well as various characteristics of this antigen are disclosed in U.S. Pat. No. 6,140,050, issued Oct. 31, 2000 entitled "Methods for Determining Breast Cancer and Melanoma by Assaying for a Plurality of Antigens Associated Therewith"; U.S. Pat. No. 5,759,783, issued Jun. 2, 1998 entitled "Method of Screening for Cancer by Detecting Messenger RNA for a MAGE-XP Gene"; and U.S. Pat. No. 5,662,907, issued Sep. 2, 1997 entitled "Induction of Anti-Tumor Cytotoxic T Lymphocytes in Humans Using Synthetic Peptide Epitopes."

As used herein, the term "MPC-10" refers to a magnetic particle concentrator.

As used herein, the term "NK cells" refers to natural killer cells.

As used herein, the term "OKT3" refers to ORTHO-CLONE OKT3, muromonab-CD3, anti-CD3 monoclonal antibody.

As used herein, the term "TAP-1,2" refers to Transporter Associated with Antigen Processing-1,2.

As used herein, the term "Th cells" refers to Helper T cells, CD4+.

As used herein, the term, "tyrosinase" refers to a protein associated with melanoma (Brichard et al., *J. Exp. Med.* (1993) 178:489-495; Robbins et al., *Cancer Res.* (1994) 54: 3124-3126). U.S. Pat. No. 5,843,648, issued Dec. 1, 1998 entitled "P15 and Tyrosinase Melanoma Antigens and Their Use in Diagnostic and Therapeutic Methods" discloses antigenic peptides and associated polynucleic acids related to tyrosinase in FIG. 7, Panels A to P, the aforementioned figure incorporated herein by reference. U.S. Pat. No. 5,487,974, issued Jan. 30, 1996 entitled "Method for Detecting Complexes Containing Human Leukocyte Antigen A2 (HLA-A2) Molecules and a Tyrosinase Derived Peptide on Abnormal Cells" discloses an additional peptide that is associated with tyrosinase and melanoma in Example 9, at Table 3, the aforementioned incorporated herein by reference.

Figure 4:
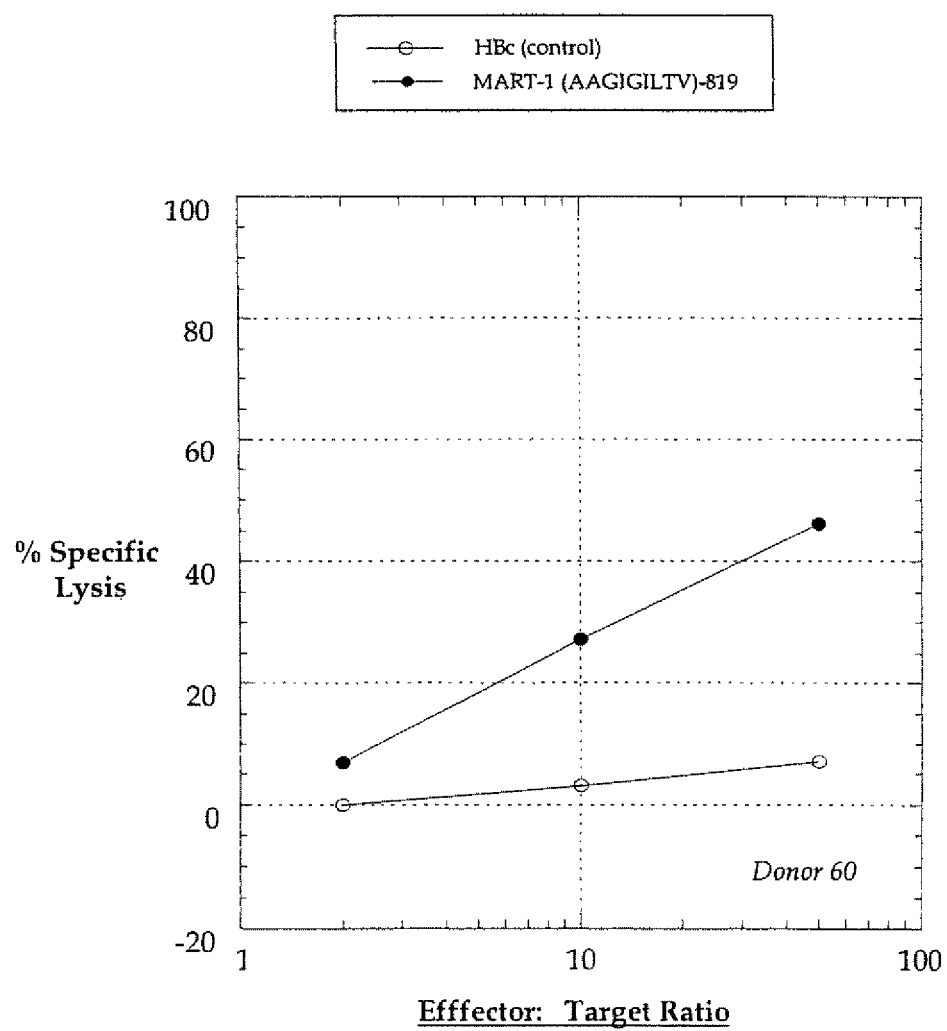
FIG. 4, Panels A, B and C This figure shows the result of an experiment where three melanoma peptides, Tyrosinase (YMNGTMSQV; SEQ ID NO: 1)-689 in Panel A, MART-1 (AAGIGILTV; SEQ ID NO: 6)-819 in Panel B, and gp100 (ITDQVPFSV; SEQ ID NO: 4)-817, were tested for the ability to raise CTLs when added as single epitopes on Drosophila cells. In a single donor, CTL activity was elicited to each of the peptides when added alone to three different Drosophila preparations. The specificity of the response was compared with control HBc peptide, a high affinity binder.
Figure 4:
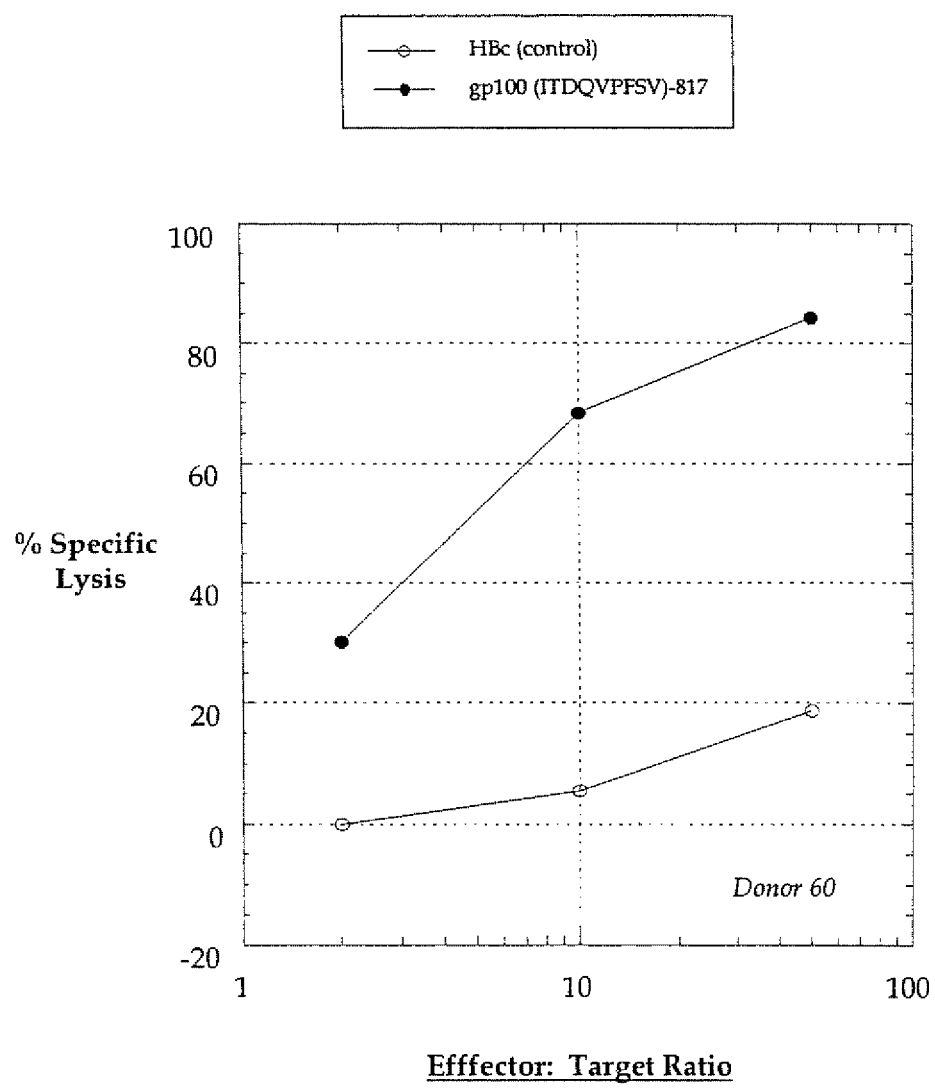
Figure 5:
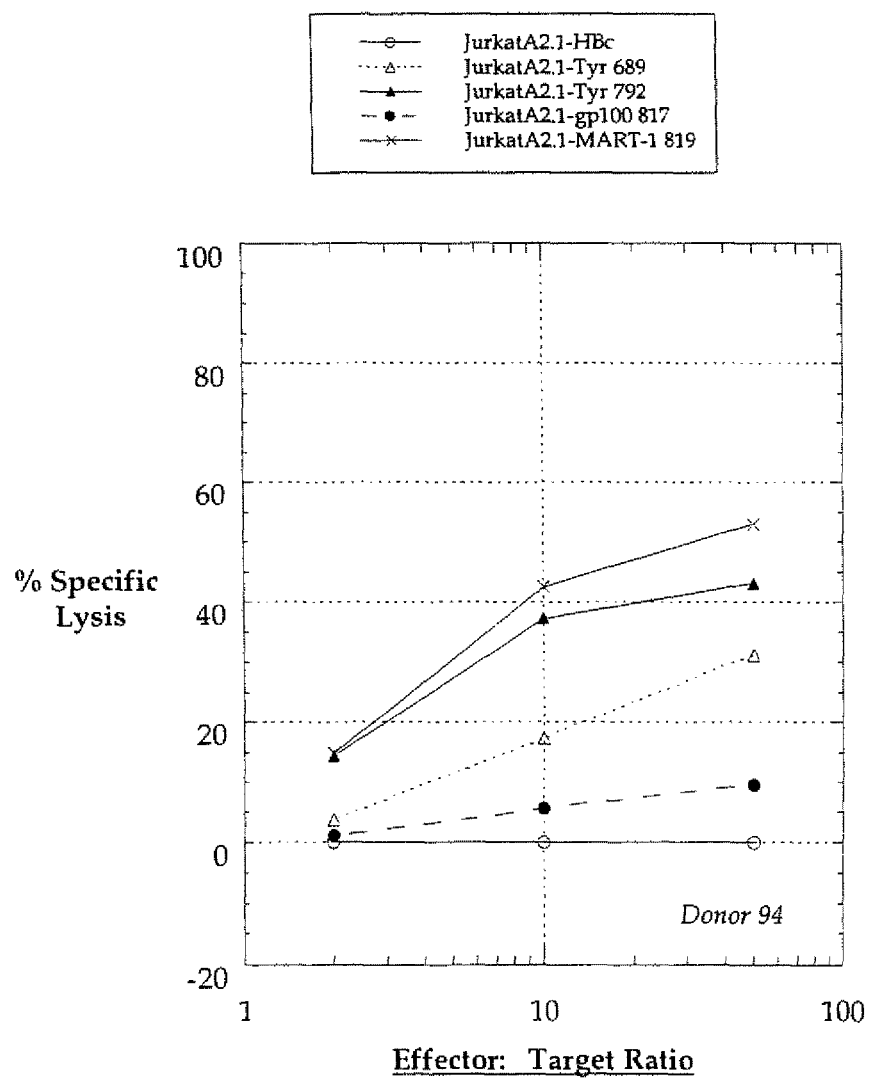
FIG. 5, Panels A, B and C:
This figure shows the results of a series of experiments where up to four different peptides were added to single Drosophila cells. CTL activity in each of the represented peptides was seen after a three-week stimulation protocol and is graphically depicted in this figure.
Figure 6:
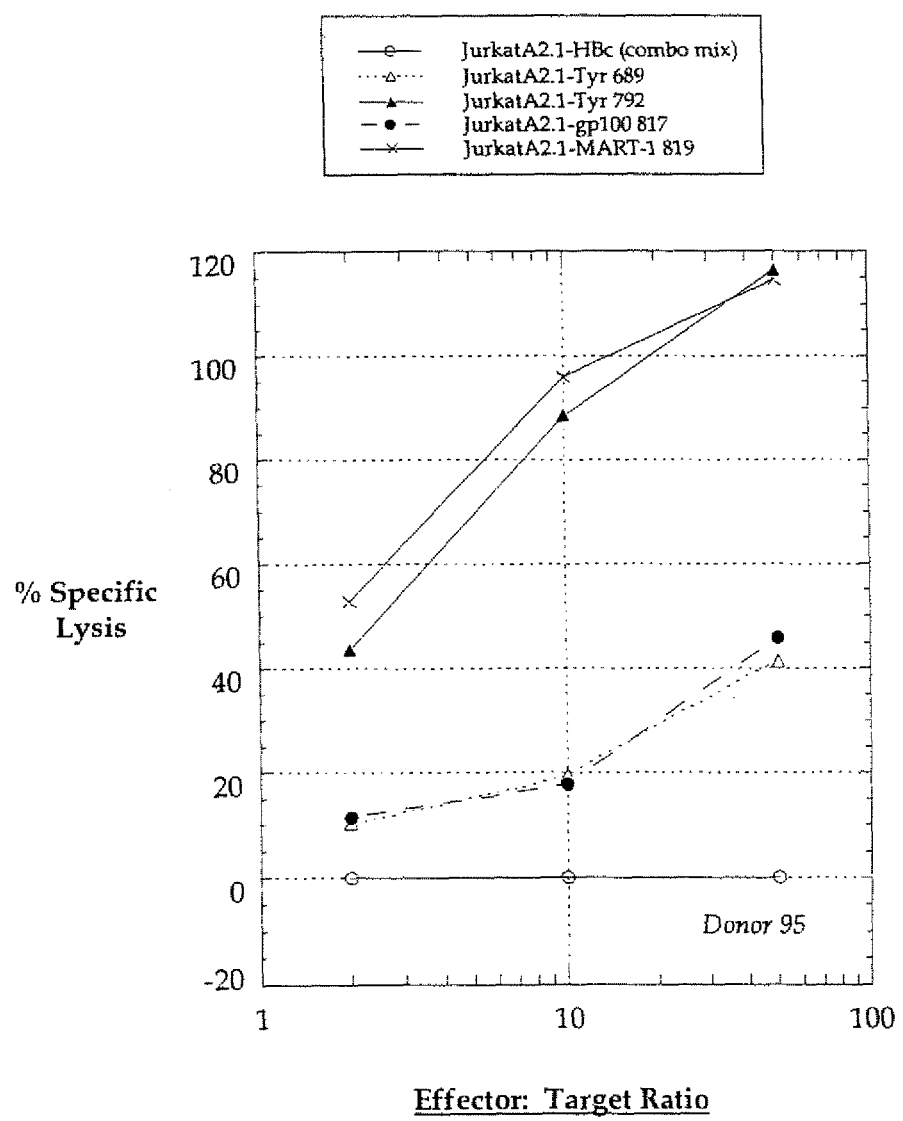
FIG. 6, Panels A, B and C:
This figure shows CTL activity after three different primary in vitro stimulation protocols.

As used herein, the term "gp100" refers to a melanoma antigen recognized by tumor infiltrating lymphocytes (TIL). The TIL which recognize gp100 is associated with in vivo tumor rejection (Bakker et al., *J. Exp. Med.* (1994) 179:1005-1009; Kawakami et al., *J. Immunol.* (1995) 154:3961-3968). Antigenc peptides related to gp100 are disclosed in U.S. Pat. No. 5,994,523, issued Nov. 30, 1999 entitled "Melanoma Antigens and Their Use in Diagnostic and Therapeutic Methods"; U.S. Pat. No. 5,874,560, issued Feb. 23, 1999 entitled "Melanoma Antigens and Their Use in Diagnostic and Therapeutic Methods"; and U.S. Pat. No. 5,844,075, issued Dec. 1, 1998 entitled "Melanoma Antigens and Their Use in Diagnostic and Therapeutic Methods." In particular, U.S. Pat. No. 5,994,523 discloses nucleic acid and amino acid sequences related to GP100 in FIGS. 4 and 5, respectively. Also disclosed are antigenic peptides derived from the ammo acid sequences, including those identified as SEQ ID NOs: 27, 33, 34, 35, 36, 37, 38, 39, 40, and 41. All of the aforementioned FIGS. 4 and 5, and the peptides identified by SEQ ID NOs are herein incorporated by referenced.

As used herein, the term "melanoma" refers to, but is not limited to, melanomas, metastatic melanomas, melanomas derived from either melanocytes or melanocytes related nevus cells, melanosarcomas, melanocarcinomas, melanoepitheliomas, melanoma in situ superficial spreading melanoma, nodular melanoma, lentigo maligna melanoma, acral lentiginous melanoma, invasive melanoma or familial atypical mole and melanoma (AM-M) syndrome. Such melanomas in mammals may be caused by, chromosomal abnormalities, degenerative growth and developmental disorders, mitogenic agents, ultraviolet radiation (UV), and infections, inappropriate tissue expression of a gene, alterations in expression of a gene, and presentation on a cell, or carcinogenic agents. The aforementioned melanomas can be diagnosed, assessed or treated by methods described in the present application.

As used herein, the term "C-lectin" refers to a peptide of the sequence that has been found to be associated with ovarian cancer.

As used herein, the term "major histocompatibility complex" or "MHC" is a generic designation meant to encompass the histocompatibility antigen systems described in different species including the human leucocyte antigens (HLA).

As used herein, the terms "epitope," "peptide epitope," "antigenic peptide" and "immunogenic peptide" refers to a peptide derived from an antigen capable of causing a cellular immune response in a mammal. Such peptides may also be reactive with antibodies from an animal immunized with the peptides. Such peptides may be about five to twenty amino acid in length preferably about eight to fifteen amino adds in length, and most preferably about nine to ten amino acids in length.

As used herein, the term "Pec60" refers to a peptide of the sequence that has been found to be associated with ovarian and breast cancer.

As used herein, the term "analog" includes any polypeptide having an amino acid residue sequence substantially identical to the sequences of the present invention, specifically shown herein in which one or more residues have been conservatively substituted with a functionally similar residue and which displays the functional aspects of the present invention as described herein. Examples of conservative substitutions include the substitution of one non-polar hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

As used herein, the term "conservative substitution" also includes the use of a chemically derivatized residue in place of a non-derivatized residue.

As used herein, the term "chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzyltistidine. Also included as chemical derivatives are those proteins or peptides which contain one or more naturally-curing amino acid derivatives of the twenty standard amino acids. For examples: 4-hydroxyproline may be substituted for proline, 5-hydroxylysine may be substituted for lysine; 3-methylhistidine may be substituted for histidine; homoserine may be substituted for serine; and ornithine may be substituted for lysine. Proteins or polypeptides of the present invention also include any polypeptide having one or more additions and/or deletions or residues relative to the sequence of a polypeptide whose sequence is encoded is the corresponding nucleic sequence of the present invention, so long as the requisite activity is maintained.

As used herein, the term "HER-2/neu" refers to an oncogene, which express or over-express, one or more membrane-associated, receptor-like oncogene proteins. Among the cancers which have been found to be associated with expression or over-expression of HER-2/neu are certain breast, stomach, ovarian colon and salivary gland cancers. The HER-2/neu oncogene is a member of the tyrosine protein kinase family of oncogenes and shares a high degree of homology with the epidermal growth factor receptor (EGFR). HER-2/neu has been shown to play a role in cell growth and/or differentiation. HER-2/neu appears to induce malignancies through quantitative mechanisms that result from increased or deregulated expression of an essentially normal gene product. U.S. Pat. No. 6,075,122, issued Jun. 13, 2000 entitled "Immune Reactivity to HER-2/neu Protein for Diagnosis and Treatment of Malignancies in Which the HER-2/neu Oncogene is Associated" discloses peptides that elicit $CD8^+$ T cell responses at column 12, line 31 to column 13, line 7, identified according to SEQ ID numbers are herein incorporated by reference.

HER-2/neu (p185) is the protein product of the HER-2/neu oncogene. The HER-2/neu gene is amplified and the HER-2/neu protein is over-expressed in a variety of cancers including breast, ovarian, colon, lung and prostate cancer. HER-2/neu is related to malignant transformation. It is found in 50% to 60% of ductal in situ carcinoma and 20% to 40% of all breast cancers, as well as a substantial fraction of adenocarcinomas arising in the ovaries, prostate, colon and lung. HER-2/neu is intimately associated not only with the malignant phenotype, but also with the aggressiveness of the malignancy, being found in one-fourth of all invasive breast cancers. HER-2/neu over-expression is correlated with a poor prognosis in both breast and ovarian cancer. HER-2/neu is a transmembrane protein with a relative molecular mass of 185 kd that is approximately 1255 amino acids (aa) in length. It has an extracelular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 amino acids with 80% homology to EGFR.

Ongoing research involving oncogenes has identified at least forty oncogenes operative in malignant cells and responsible for, or associated with, transformation. Oncogenes have been classified into different groups based on the putative function or location of their gene products (such as the protein expressed by the oncogene). Oncogenes are believed to be essential for certain aspects of normal cellular physiology.

Cancer continues to be a major health problem, despite significant progress made in the area of treatment. The standard treatment regimes of chemotherapy, radiation therapy, surgical intervention and combinations of the three, often fail to produce a long lasting cure. In many cases, the cancer patient having undergone the treatment often relapses back to the disease condition after some period of time, further exacerbating the problem, is the severity of these treatment regimes to the patient. In the instance of melanoma, a cure for metastatic melanoma has not been achieved using conventional chemotherapy. Response rates of 35% to 50% have been reported with the Dartmouth regimen of combination chemotherapy (DTIC, cis-platin, BCNU and tamoxifen), but the duration of survival has remained at six to ten months. High rates of remission have been reported for aggressive "high dose intensity" chemotherapy and repletion of hematopoiesis with autologous bone marrow transplants. Nevertheless, the median duration of survival was short, approximately four months.

Rosenberg and colleagues have attempted to use infusion of activated lymphocytes as a treatment for various cancers. Initially, lymphokine-activated killer cells (LA) and later tumor-infiltrating lymphocytes (TIL) activated ex vivo with IL-2 were used, but evidence for efficacy is equivocal. In fact, controlled clinical trials have failed to show an advantage to the use of ex vivo-activated cells over direct administration of IL-2 to patients. Thus, the benefits of LAK and TL therapy are marginal, and the side effects are typically so severe that many trials have been discontinued prematurely.

Studies in mouse tumor models have demonstrated that adoptive immunotherapy, in vivo immunization of T cells specific for a tumor antigens(s), is very efficacious with toxicity. A major obstacle to applying his strategy to the treatment of human tumors is the identification of immunogenic antigens that render the tumor cells susceptible to cytotoxic T lymphocyte (CTL)-mediated destruction. The isolation of tumor-reactive T cells from melanoma patients has led to the identification of some of the tumor antigens (epitopes) against which CTLs are directed. These include tyrosinase (Brichard et al., *J. Exp. Med*. (1993) 178:489-495; Robbins et al., *Cancer Res*. (1994) 54:3124-3126), MART 1/Melan A (Kawakami et al., *J. Exp. Med*. (1994) 180:347-352), gp 100 (Bakker et al., *J. Exp. Med*. (194) 179:1005-1009; and Kawakarni et al., *J. Immunol*. (1995) 154:3961-3968) and MAGE (Gaugler et al., *J. Exp. Med*. (1994) 179:921-930). Of these, tyrosinase and MART-1 are nearly universally expressed on melanomas and thus are the logical choice for adoptive immunotherapy.

In recent years, significant improvements in survival on the order of several years have been noted in a small percentage of melanoma patients undergoing immunological therapy. This includes active specific immunotherapy with "cancer vaccines" as well as the use of non-Fr specific boosters of the immune system such as cytokines, like IL-2, α-interferon and γ-interferon. However, the benefit of cytokines is lessened by side effects that often accompany their use, such as, nausea, and fever.

Cytolytic T cells ($CD8^+$) are the main line of defense against viral infections. $CD8^+$ lymphocytes specifically recognize and kill host cells that are infected by a virus. Theoretically, it should be possible to harness the immune system to combat other types of diseases including cancer. However, few in vitro/ex vivo procedures have been available for specifically activating CTLs. The identification of key melanoma antigens noted above and a method for specific in vitro activation CTLs described below now allow testing of the concept of adoptive immunotherapy of metastatic melanoma.

All naive T cells require two signals for activation to elicit an immune response. For $CD8^+$ lymphocytes (CTLs), the first signal, which imparts specificity, consists of presentation to the $CD8^+$ cell of an immunogenic peptide fragment (epitope) of the antigen bound to the Class I MHC (HLA) complex present on the surface of antigen-presenting cells (APCs). This complex is recognized specifically by a T cell antigen receptor TCR), which communicates the signal intracellularly.

Binding to the T cell receptor is necessary but not sufficient to induce T cell activation, and usually will not lead to cell proliferation or cytokine secretion. Complete activation requires a second costimulatory signal(s), these signals serve to further enhance the activation cascade. Among the co-stimulatory molecules on antigen-presenting cells, B7 and cell adhesion molecules (integrins) such as ICAM-1 assist in this process by binding to CD28 and LFA-1, respectively, on the T cell. When a $CD8^+$ cell interacts with an antigen-presenting cell bearing an immunogenic peptide (epitope) bound by a Class I MHC molecule in the presence of appropriate co-stimulatory molecule interactions, the $CD8^+$ cell becomes a fully activated cytolytic T cell.

Lymphocyte-mediated cell killing involves a sequence of biological events beginning with the binding of the $CD8^+$ CTL to an antigen-bearing target (tumor) cell by means of the recognition process described above for T cell activation.

The interaction between $CD8^+$ cells and antigen-presenting cells or target (tumor) cells as described above is depicted in FIG. 1. The interaction begins with the binding of antigen in association with an MC Class I molecule on the APC or target cell to the T cell antigen receptor (TCR). Accessory molecules such as lymphocyte function antigens (LFA-1, LFA-2 and LFA-3), intercellular adhesion molecule 1 (ICAM-1), T cell co-stimulatory factors (CD2, CD28, B7) enhance cell-cell adhesion or transduce additional cell activation signals.

After cell-cell interaction, the CTL kills the target cell through the action of soluble cytolytic mediators (perforin and granzymes stored in cytoplasmic granules in the T cell) and a CTL surface molecule (Fas ligand). After the cytolytic attack, target cells die by necrosis (membrane perforation and organelle destruction) or apotosis (chromatin condensation, DNA fragmentation and membrane blebbing).

The mechanisms of lymphocyte-mediated cytolysis is graphically depicted in FIG. 2. In Panel A of FIG. 2, after binding to the target cell, cytoplasmic granules in the CTL are rapidly reoriented toward the target cell for release of granules containing perforin and granzymes into the intercellular space. These proteolytic enzymes form pores in the plasma membrane of the target cell eventually leading to cell necrosis. In Panel B, after binding to the target cell, the level of Fas ligand expression on the CTL increases. The interaction of Fas ligand and the Fas receptor on the target cell leads to apoptosis. Proteases such as CPP32 and others related to IL-1b-converting enzyme (ICE) have been implicated in the induction of apoptosis. It is possible to use naturally-occurring antigen-presenting cells, for example, dendritic cells, macrophages, autologous tumor cells for in vitro $CD8^+$ activation. However, the efficiency of activation following this approach is low. This is because the Class I molecules of native APCs contain many other types of peptide epitopes besides tumor epitopes. Most of the peptides are derived from normal innocuous cell proteins, resting in a dilution of the number of active native APCs that would actually be effective against a tumor (Allison et al., *Curr. Op. Immunol.* (1995) 7:682-686).

A more direct and efficient approach to is problem is to specifically activate $CD8^+$ cells only with those epitopes relevant to combating a specific disease, (such as, cancer) or tumor specific antigens (such as, melanoma-specific antigens). To this end, an artificial antigen presenting cell is created by expressing MHC Class I molecules in *Drosophila melanogaster* (fruit fly) cells. Since *Drosophila* does not have an immune system, the TAP-1,2 peptide transporters involved in loading peptide epitopes onto class I molecules are absent. As a result, the class I molecules appear on the *Drosophila* cell surface as empty vessels. By incubating these transfected *Drosophila* cells with exogenous peptides that bind to the class I molecules, such as, cancer or tumor specific epitopes, including but limited to, melanoma specific epitopes, it is possible to occupy every class I molecule with the same peptide. High density expression of class I molecules containing a single peptide in these *Drosophila* APCs permit generation of cytotoxic $CD8^+$ T cells in vitro which are completely specific for the antigen peptide. Methods and procedures for preparing *Drosophila* cells are taught in U.S. Pat. No. 5,529,921, issued Jun. 25, 1996 entitled "In Vitro Activation of Cytotoxic T-Cells Using Insect Cells Expressing Human Class I MHC and β2-Microglobulin", and U.S. Pat. No. 5,314,813, issued May 24, 1994 entitled "*Drosophila* Cell Lines Expressing Genes Encoding MHC Class I Antigens And β2-Microglobulin and Capable of Assembling Empty Complexes and Methods of Making Said Cell Lines". In particular, U.S. Pat. No. 5,529,921 discloses at column 26, line 56 to column 28, line 22 various methods of separating out and/or enriching cultures of precursor cells.

Additionally, this feature eliminates the need for in vivo stimulation of the immune system with high doses of various cytokines. Thereby resulting in a treatment that fore goes the side effects caused by cytokines. Alternatively under suitable situations, or conditions, where appropriate and where the subject can derive benefit, the subject can be treated concurrently with low level dosages of a interferon, γ-interferon, and/or IL-2.

Eliminating the need for in vivo stimulation with cytokines provides an improvement to the quality of patient care. Treatment regimes that include the administration of cytokines to patients often result in the patient developing flu-like symptoms, such as nausea, vomiting, and fever. These side reactions are generally not life threatening, although a particularly severe reaction occurring in a patient who is already in a weaken condition could result in a life endangering situation. Another consideration is the adverse impact such side reactions have on patient acceptance and compliance of an otherwise beneficial treatment regime. Removing the need for in vivo stimulation with cytokines results in a treatment regime that improves the comfort of the patient, and provides the clinician with an effective method of treatment that his or her patient is more likely to comply with.

The utility of this method for adoptive immunotherapy of tumors has been demonstrated in mice using transfected *Drosophila* cells as APCs and $CD8^+$ cells from the 2C line of T cell receptor (TCR) transgenic mice. In this system, purified $CD8^+$ 2C cells are highly responsive to in vitro peptides presented by MHC Class I ($L^d$)-transfected *Drosophila* cells also bearing the co-stimulatory molecules B7-1 and ICAM-1. Transfected *Drosophila* cells as a probe for defining the minimal requirements for stimulating unprimed $CD8^+$ T cells (Cai et al., *P.N.A.S. USA* (1996) 93:14736-14741). Alternatively, when un-separated mouse spleen cells are used as responders in place of purified 2C cells, the need for co-stimulatory molecules does not apply. In this instance, the $CD8^+$ cells in the spleen population receive "bystander" co-stimulation from activated B cells. Utilizing this finding, it has been possible to show that MHC Class I ($L^d$)-transfected *Drosophila* cells are able to induce normal DBA/2 mouse spleen cells to respond to syngeneic P815 mastocytoma tumor-specific peptides in vitro in the absence of added lymphokines.

Injection of these CTLs into DBA/2 mice bearing P815 mastocytoma led to rapid tumor regression (Sun et al., *Immunity* (1996) 4:555-564).

Figure 3:
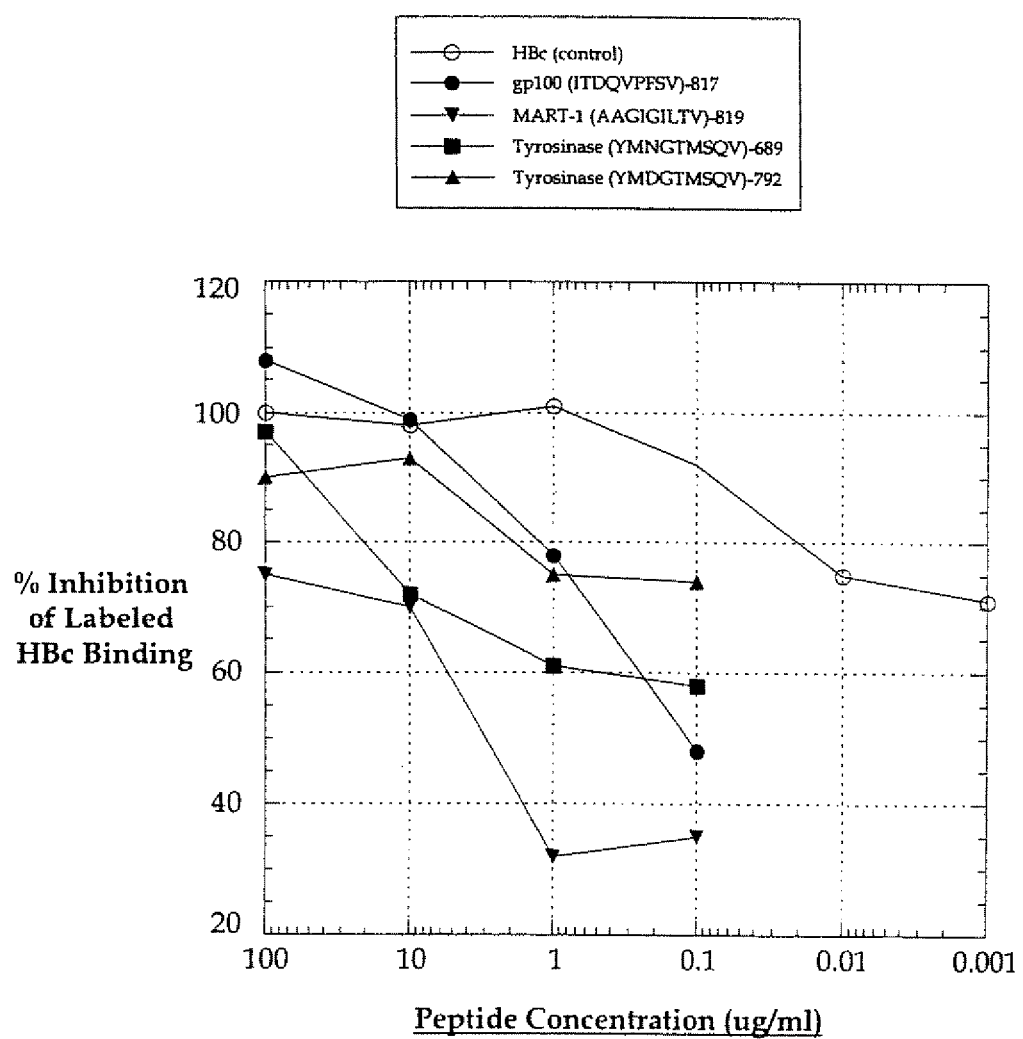
FIG. 3: This figure shows the result of an experiment where several different peptides, gp100 (ITDQVPFSV; SEQ ID NO: 4)-817, MART-1 (AAGIGILTV; SEQ ID NO: 6)-819, Tyrosinase (YMNGTMSQV; SEQ ID NO: 1)-689 and Tyrosinase (YMDGTMSQV; SEQ ID NO: 2)-792, were tested in a competition assay to identify peptide binders that could be used to load multiple peptides onto Drosophila cells expressing human empty class I molecules.

Procedurally, normal DBA/2 mouse spleen cells were cultured in vitro with MHC Class I ($L^d$)-transfected *Drosophila* cells loaded with P1A.35-43 peptide, a tumor-specific epitope from the DBA/2-derived P815 mastocytoma cell line. Lymphocytes harvested from the cultures after five days displayed strong cytotoxic T lymphocyte (CTL) activity toward P815 tumor cells in vitro, but failed to lyse P1024, a mutant cell line of P815 that does not express P1A.35-43, as shown in FIG. 3, Panel A. When these CTLs were injected into DBA/2 mice previously inoculated with P815 cells three days earlier, the tumors grew unimpeded during the first week, but were subsequently eliminated within the next week, as shown in FIG. 3, Panel B. Specificity was demonstrated by the absence of any effect on P815 growth when CTLs were immunized in vitro against an irrelevant antigen, such as, viral nucleoprotein peptide, as shown in FIG. 3, Panel B. In summary, major histocompatibility complex Class I (Ld)-transfected *Drosophila* cells induced normal DBA/2 mouse spleen cells to respond to syngeneic P815 mastocytoma tumor-specific peptides in vitro in the absence of added lymphokines. Injection of these CTLs into DBA/2 mice bearing P815 mastocytoma led to rapid tumor regression (Wolfel et al., *J. Exp. Med.* (1993) 178:489-495).

Human Studies In Vitro

Human CTLs from healthy subjects were immunized in vitro against tyrosinase. Following primary stimulation only with *Drosophila* cells, specific lysis of tyrosinase-bearing JY cells was evident at all CLT effector to JY target ratios tested. Tyrosinase-specific CTLs from healthy subjects were induced using the full stimulation/re-stimulation protocol and tested for their ability to kill the Malme 3M melanoma cell line. With one or two possible exceptions, specific CTL activity against Malme 3M was induced in all donors to a varying extent. For the most part, reactivity toward control Malme 3 tumor cells was minimal. Cells from melanoma patients were also immunized in vitro against the tyrosinase epitope to generate CTLs of similar activity and specificity to those derived from healthy volunteers.

The use of any natural, or artificial, antigen presenting cell (APC) system to generate cytotoxic T lymphocytes in vitro is limited by the antigen specificities these systems are capable of generating.

The following APC systems have been utilized to generate antigen-specific CTL's to single epitopes: 1) human dendritic cells (DC) pulsed with defined peptides; 2) peripheral blood mononuclear cells (PBMCs) which have been driven to lymphoblasts and pulsed with peptides; 3) lymphoblastoid cell lines (LCL) where the natural peptides are add-stripped and loaded with the peptides of interest; 4) *Drosophila* cells engineered to express empty class I molecules; and Mouse 3T3 cells transfected with h class I and co-stimulatory molecules (J. B. Latouche and M. Sadelain, *Nature Biotech* (2000) 18:405-409).

Dendritic cells (DCs) are considered the primary antigen presenting cell system in humans because of their wide application in presenting primary antigen cells. Self or foreign proteins are processed within a DC. The resultant peptide epitopes are presented by HLA molecules, and are transported to the surface of the DC. However, it was found that DCs would not consistently generate in vitro, CTLs directed against four different peptides. This would have provided CTLs having activity corresponding to each of the four peptides. In addition, it was also found that the phenotype of the DC at the time of peptide pulsing, mature or immature, did not effect the outcome.

Alternatively, *Drosophila* cell stimulation usually resulted in CTLs directed against up to ten different types of peptides. This provides CTLs that are active to each of the ten peptides.

Figure 8:
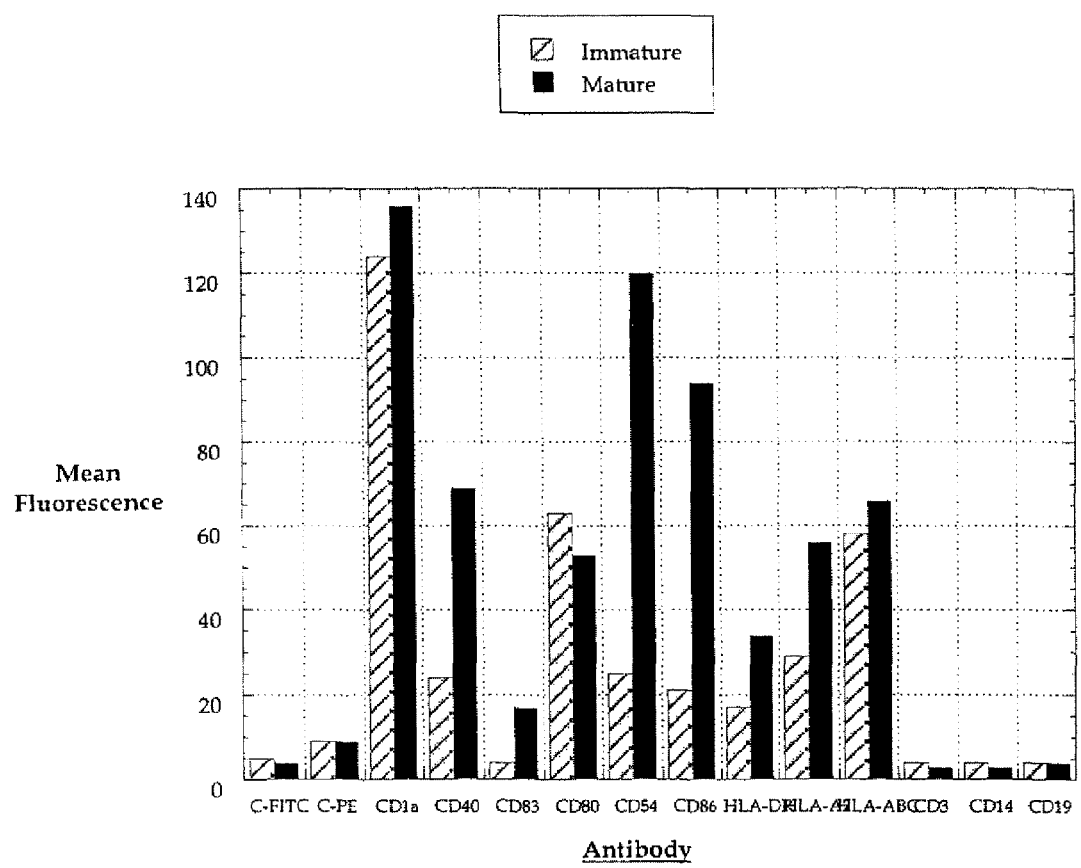
FIG. 8: This figure shows that the dendritic cells displaying either mature or immature phenotype was not as efficient as Drosophila cells in eliciting specific CTL responses when defined peptides were used to pulse the cells.
Figure 11:
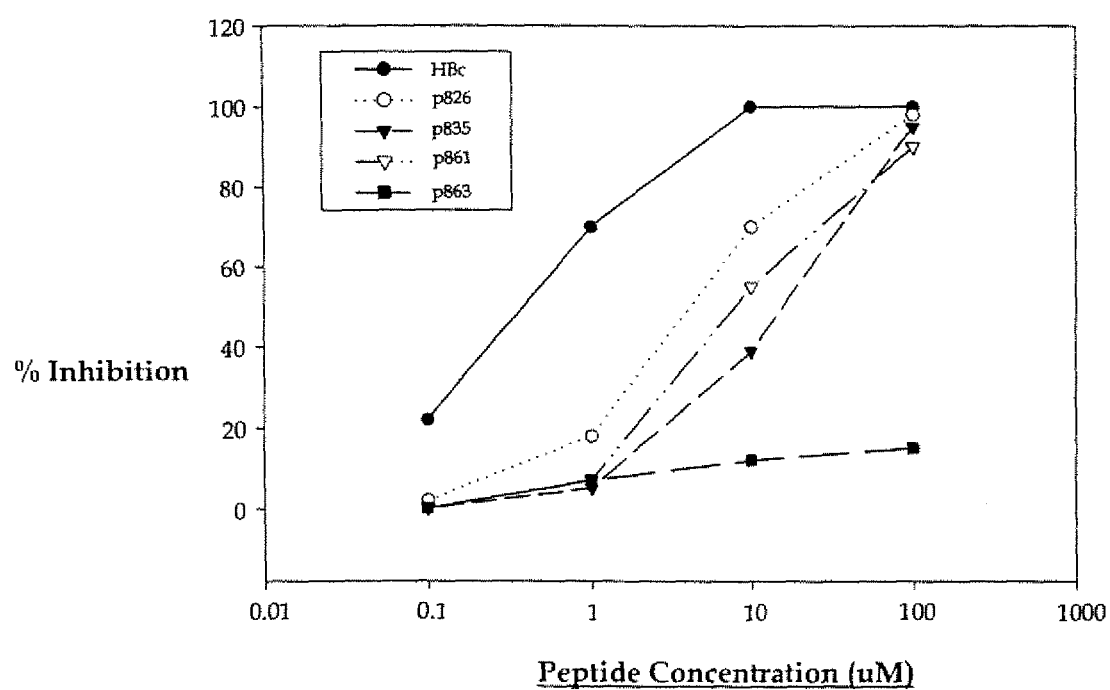
FIG. 11: This figure shows the peptide binding capacity of the HER-2 peptides (826, 835, 861 and 863) on the Drosophila cells transfected with the human HLA-A2.1 class I molecule.

The ability of *Drosophila* cells and DC to elicit CTL responses were evaluated, initially to a single peptide epitope, following the standard stimulation protocols for each. In order to compare DCs and transfected *Drosophila* cells. Immature DCs were generated by culturing for one week autologous monocytes in the presence of IL-4 and GM-CSF. Mature DCs were obtained from immature DCs by addition of TNF a to the culture medium twenty-four hours prior to harvesting. DCs (immature and mature) were harvested, pulsed with peptides and mixed with purified CD8 cells following the procedure used for the stimulation of CD8 cells and peptide-pulsed *Drosophila* cells. *Drosophila* cells were found to be generally better stimulators than DC when evaluated for tyrosinase peptide epitope 689, as shown in FIG. 7. Further, DCs displaying either the immature or mature phenotype (FIG. 8) were not as efficient as *Drosophila* cells in eliciting specific CTL responses when defined peptides were used to pulse the APCs. This is particularly surprising, because of the dominant role played by DCs in the immune system. A comparison study with one donor was performed, as shown in FIG. 9. Specific killing was generated against four different peptides when using fly cells as stimulators whereas mature DCs resulted in marginal specific killing and mature DCs resulted in specific killing against only one of the four peptides used for stimulation.

Preparation of Cytotoxic Lymphocytes $CD8^+$ cells isolated from leukopheresis samples by positive selection with anti-CD8 antibody are stimulated against four different melanoma associated peptides presented by *Drosophila* cells expressing Human Class I molecules (HLA-A2.1), B7.1, ICAM-1, LFA-3 and B7.2. $CD8^+$ cells are re-stimulated for two rounds with autologous monocytes loaded with the ±5 peptide epitope in the presence of IL-2 and IL-7. CTLs are non-specifically expanded with OKT3 and IL-2. CTL activity is measured against Malme 3M cells and purity of $CD8^+$ T cells is assessed by flow cytometry.

The manufacturing processes and protocols are done according to Good Laboratory Practices and Good Manufacturing Practices. "Good Laboratory Practices" and "Good Manufacturing Practices" are standards of laboratory and manufacturing practices which are set by United States Food and Drug Administration, and are readily known to those of skill in the art. The CTLs are monitored for identity, viability, CTL activity, sterility, and endotoxin content.

A listing of peptide epitopes suitable for use in the methods of the present invention to treat breast and ovarian cancers are shown in the following Table 1. It is readily apparent to those of ordinary skill in the art that a wide variety of peptide epitopes in addition to those listed in the following Table 1 will also be suitable for use in the methods of the present invention to treat breast and ovarian cancers, provided that such peptides are T cell epitopes,

TABLE 1

Identified HLA-A2.1 Restricted Epitopes for Tumor Associated Antigens as Targets for Breast and Ovarian Cancers

| Target (residues) | Name | PRI # | AKA | Sequence (SEQ ID NO:) | HLA Peptide-Binding Prediction |
|---|---|---|---|---|---|
| Her-2/neu | | | | | |
| 789-797 | | 826 | E90 | CLTSTVQLV (SEQ ID NO: 7) | 160 |
| 48-56 | | 827 | D113 | HLYQGCQVV (SEQ ID NO: 13) | |
| 369-377 | | 835 | E75 | KIFGSLAFL (SEQ ID NO: 8) | 481 |
| 654-662 | | 837 | GP2 | IISAVVGIL (SEQ ID NO: 14) | |
| 650-658 | | 838 | GP1 | PLTSIISAV (SEQ ID NO: 15) | |
| 773-782 | | 861 | | VMAGVGSPYV (SEQ ID NO: 16) | |
| 851-859 | | 862 | E89 | VLVKSPNHV (SEQ ID NO: 17) | 118 |
| 971-979 | | 863 | C85 | ELVSEFSRM (SEQ ID NO: 18) | |
| AES | Amino enhancer of the split Notch | | | | |
| G128-135 | | 893 | G76 | GPLTPLPV (SEQ ID NO: 19) | |
| MUC-1 | Mucin | | | | |
| 950-958 | | 908 | 1.1 | STAPVHNV (SEQ ID NO: 20) | |
| CEA | Carcinoembryonic Ag | | | | |
| 571-579 | | 879 | CAP-1 | YLSGANLNL (SEQ ID NO: 21) | |
| FBP | Folate binding protein | | | | |
| 191-199 | | 914 | E39 | EIWTHSYKV (SEQ ID NO: 22) | |
| C-Lectin | MESM, RELP | | | | |
| 8-16 | | | C8 | KMASRSMRL (SEQ ID NO: 9) | CTL Activity |
| 77-86 | | | C77 | SILSLKEAST (SEQ ID NO: 23) | CTL Activity |
| NY-ESO-1 | | | | | |
| 157-165C | | 894 | | SLLMWITQC (SEQ ID NO: 24) | native |
| 157-165V | | 906 | | SLLMWITQV (SEQ ID NO: 25) | modified |
| 155-163 | | 913 | | QLSLLMWIT (SEQ ID NO: 26) | |
| Pec60 | | | | | |
| 20 | | | P20 | ALALAALLVV (SEQ ID NO: 10) | CTL Activity |
| 25 | | | P25 | ALLVVDREV (SEQ ID NO: 11) | CTL Activity |

TABLE 1-continued

Identified HLA-A2.1 Restricted Epitopes for Tumor
Associated Antigens as Targets for Breast and
Ovarian Cancers

| Target (residues) | Name | PRI # | AKA | Sequence (SEQ ID NO:) | HLA Peptide-Binding Prediction |
|---|---|---|---|---|---|
| CA-125 | | | | | |
| 157-165 | | 900 | | YLETFREQV (SEQ ID NO: 27) | 38 |
| 255-263 | | 902 | | VLLKLRRPV (SEQ ID NO: 28) | 88 |
| 337-345 | | 901 | | GLQSPKSPL (SEQ ID NO: 29) | 21 |
| 546-554 | | 903 | | ELYIPSVDL (SEQ ID NO: 30) | 5 |
| 898-906 | | 899 | | KALFAGPPV (SEQ ID NO: 31) | 13 |
| 414-422 | | 910 | | FMWGNLTLA (SEQ ID NO: 32) | 315 |
| MAGE-3 | | | | | |
| 271-279 | | 909 | | FLWGPRALV (SEQ ID NO: 33) | |
| Telomerase 540-548 | hTRT | 907 | | ILAKFLHWL (SEQ ID NO: 34) | |
| 865-873 | | 911 | | RLVDDFLLV (SEQ ID NO: 35) | |
| G250 | | | | | |
| 245-262 | | 912 | | HLSTAFARV (SEQ ID NO: 36) | |

The following examples are provided for the purpose of illustrating the present invention, but do not limit the present invention to the content of the examples.

EXAMPLE 1

Manufacture of *Drosophila* Antigen-Presenting Cells

The Schneider S2 cell line was prepared from *Drosophila melanogaster* (Oregon-R) eggs according to published procedures and has been deposited with the American Type Culture Collection (CRL 10974). S2 cells are grown in commercial Schneiders *Drosophila* medium supplemented with 10% fetal bovine serum.

The pRmHa-3 plasmid vector for expressing MHC Class I and co-stimulatory proteins in 92 cells was derived from the pRmHa-1 expression vector constructed as described in the literature. It contains a metallothionein promoter, metal response consensus sequences and an alcohol dehydrogenase gene bearing a polyadenylation signal isolated from *Drosophila melanogaster*.

Complementary DNAs for Transfection were Prepared as Follows:

| | |
|---|---|
| HLA-A2.1 and β-2 microglobulin: | Reverse transcription-PCR from K562 cells using primers derived from the published sequence |
| B7.1: | Reverse transcription-PCR from K562 cells using primers derived from the published sequence |
| ICAM-1: | Reverse transcription-PCR from K562 cells using primers derived from the published sequence |
| B7.2: | Reverse transcription-PCR from HL-60 cells (ATCC CCL-240) using primers derived from the published sequence |
| LFA-3: | Reverse transcription-PCR from HL-60 cells (ATCC CCL-240) using primers derived from the published sequence |

Complementary DNAs were individually inserted into the pRmHa-3 vector. S2 cells were transfected with a mixture of HLA-A2.1, B7.1 and ICAM-1 plasmid DNAs and the phsh-neo plasmid using the calcium phosphate precipitation method. Stably transfected cells were selected by culturing in Schneider's medium containing geneticin. Twenty-four hours before use, expression of the transfected genes was induced by addition of $CuSO_4$. The level of expression was assessed by flow cytometry using anti-HLA-A2.1, anti-B7.1 and anti-ICAM-1 antibodies. HLA expression by greater than 30% of the cells is necessary for efficient in vitro activation of $CD8^+$ lymphocytes.

Isolation of Human $CD8^+$ Cells $CD8^+$ cells are isolated from leukopheresis samples by positive selection using the Dynabeads™ isolation procedure (Dynal). An anti-human CD8 mouse monoclonal antibody (50 µg/ml in human gamma globulin [Gammagard®]) is added to washed cells in Dulbecco's PBS supplemented with 1% human serum albumin (Baxter-Hyland) and 0.2% Na citrate. After incubation at 4° C. for forty-five minutes with gentle mixing, the cells are washed and re-suspended in the same buffer containing Dynal magnetic beads (Dynabeads™) coated with sheep anti-mouse IgG at a bead to cell ratio of 1:1. The cells and beads are placed into a sterile tube and gently mixed at 4° C. for forty-five minutes. At the end of this time, the antibody-bound cells are removed magnetically using the MPC-1® separator according to the manufacturer's instructions (Dynal). Dissociation of the CD8 cell-bead complex is achieved by incubation at 37° C. for forty-five minutes in the presence of CD8 peptide$_{59-70}$ (AAEGLDTQRFSG; SEQ ID NO: 12). Free beads are removed magnetically and the CD8 cells are counted and analyzed by flow cytometry to evaluate purity. Recovery of CD8$^+$ cells is typically greater than 80%. Table 1 summarizes the cell composition of fourteen separate CD8$^+$ preparations from normal human PBMC preparations by positive selection with anti-CD8 antibody,

TABLE 2

Purification of CD8$^+$ Cells by Positive Selection Analyzed by Flow Cytometry

| CELL TYPE | PBMC | | POST SELECTION | |
|---|---|---|---|---|
| | Mean % | (Range) | Mean % | (Range) |
| CD8 T cells | 15% | (7-24) | 82% | (56-95) |
| CD4 T cells | 36% | (14-52) | 2% | (0.1-10) |
| CD 14 Monocytes | 15% | (7-26) | 0.8% | (0.2-2) |
| CD15 Neutrophils | 12% | (8-21) | 0.6% | (0.1-3) |
| CD19 B cells | 2% | (0.4-7) | 3% | (0.5-9) |
| CD56 NK cells | 6% | (2-17) | 6% | (0.1-20) |

In Vitro Immunization of Purified Human CD8$^+$ Cells

Primary Stimulation

Transfected *Drosophila* S2 cells are incubated in Schneider's medium (10$^6$ cells/ml) supplemented with 10% fetal calf serum and CuSO$_4$ at 27° C. for twenty-four hours. Cells are harvested, washed and re-suspended in Insect X-press medium (BioWhittaker) containing 100 µg/ml human tyrosinase$_{369-377}$. Following incubation at 27° C. for three hours, the S2 cells are mixed with CD8$^+$ cells at a ratio of 1:10 in RPMI medium (Gibco) supplemented with 10%, autologous serum. The cell mixture is incubated for four days at 37° C. during which the *Drosophila* cells die off. On Day five, IL-2 (20 U/n) and IL-7 (30 U/ml) are added to selectively expand the tyrosinase-specific CTL population.

Re-Stimulation

Frozen, autologous, CD8-depleted PBMCs, obtained at the time of leukopheresis, are thawed, washed and re-suspended at 10$^6$ cells/ml in RPMI medium containing 10% autologous serum (as a source of β2 microglobulin) and 20 µg/ml tyrosinase$_{369-377}$. Following γ-irradiation (5,000 rads), the cells are incubated at 37° C. for two hours. Non-adherent cells are removed by washing with Dulbecco's PBS. Adherent monocytes are loaded with the tyrosinase epitope by incubation for 90 minutes in Hepes-buffered RPMI medium containing 10% autologous serum and 10 µg/ml tyrosinase$_{369-377}$. The supernatant is removed and the *Drosophila*-activated CD8$^+$ cell suspension (3×10$^6$ cells/ml in RPMI medium with 10% autologous serum) is added at a ratio of 10 CD8$^+$ cells to 1 adherent monocyte. After three to four days of culture at 37° C., IL-2 (20 U/ml) and IL-7 (30 U/ml) are added with a medium change to selectively expand the tyrosinase-specific CTL population.

Non-specific Expansion

Effector cells are non-specifically expanded by culturing them in RPMI medium supplemented with autologous serum, anti-CD3 monoclonal antibody (OKT®3), IL-2 and γ irradiated autologous PBMCs.

Assays for Activity and Purity

CTL Assay

Malme 3M cells are used as target cells in a $^{51}$Cr release assay, 5×10$^6$ Malme 3M cells in RPMI medium containing 4% fetal calf serum, 1% HEPES buffer and 0.25% gentamycin are labeled at 37° C. for one hour with 0.1 mCi $^{51}$Cr. Cells are washed four times and diluted to 10$^5$ cells/ml in RPMI with 10% fetal bovine serum (HyClone). In a 96-well microliter plate, 100 µl effector CTLs and 100 µl peptide-loaded, $^{51}$Cr-labeled Malme 3M target cells are combined at ratios of 100:1, 20:1 and 4:1 (effector:target), K562 cells are added at a ratio of 20:1 (K562:Malme 3M) to reduce natural killer cell background lysis. Non-specific lysis is assessed using the non-tumor HLA-A2.1 fibroblast cell line, Malme 3. Controls to measure spontaneous release and maximum release of $^{51}$Cr are included in duplicate. After incubation at 37° C. for six hours, the plates are centrifuged and the supernatants counted to measure $^{51}$Cr release.

Percent specific lysis is calculated using the following equation:

$$\frac{cpm \text{ sample} - cpm \text{ spontaneous release}}{cpm \text{ maximum release} - cpm \text{ spontaneous release}} \times 100$$

Flow Cytometry.

CD8$^+$ cells, before and after in vitro activation, were analyzed for a number of cell surface markers using fluorescent monoclonal antibodies and FACS analysis. Results from a typical activation protocol using cells from a healthy donor is shown in Table 2.

TABLE 3

Flow Cytometry Analysis of In Vitro Activated CD8$^+$ Cells

| MARKER/CELL TYPE | PRE-ACTIVATION Mean % | POST-ACTIVATION Mean % |
|---|---|---|
| CD8 T cell | 98 | 99 |
| TCRαβ T cell receptor | 98 | 92 |
| CD 44 lymph node homing receptor | 91 | 99 |
| CD45RO memory T cell | 58 | 88 |
| CD45RA | 41 | 31 |
| CD62L HEV homing receptor | 24 | 38 |
| CD56 NK cell | 1 | 11 |
| CD25 activated T cell | 0.1 | 29 |

In addition to activity and purity, CTL preparations will be assayed for sterility and endotoxin content.

REAGENTS

| REAGENT | SUPPLIER | GRADE | NOTES |
|---|---|---|---|
| rh IL-2 | Chiron | USP | sterile solution |
| rh IL-7 | Genzyme | Research | lyophilized, sterile solution |
| human tyrosinase$_{369-377}$ | | Research | |
| Dynabeads ® M-450 | Dynal | GMP | sheep anti-mouse IgG magnetic beads |
| human serum | Baxter | USP | sterile, non-pyrogenic |

-continued

| REAGENTS | | | |
|---|---|---|---|
| REAGENT | SUPPLIER | GRADE | NOTES |
| albumin | | | hepatitis virus-free, 25% solution |
| fetal bovine serum | Gemini | Research | sterile, BSE-, endotoxin-, mycoplasma-free |
| Gammagard ® | Baxter | USP | sterile, human immune globulin solution for injection |
| anti-CD8 antibody | | Research | mouse anti-human CD8 monoclonal antibody |
| CD8 peptide$_{59-70}$ | | Research | release of CD8$^+$ cells from magnetic beads |
| W6/32 | ATCC | Research | mouse anti-human HLA-A, B, C monoclonal antibody |

| CELL LINES | | |
|---|---|---|
| CELL LINE | SUPPLIER | NOTES |
| *Drosophila* S2 | ATCC | CRL 10974 |
| M3 | UCSD | Non-HLA-A2.1 human melanoma |
| Malme 3 | ATCC | Normal skin fibroblast from a melanoma patient |
| Malme 3M | ATCC | Metastatic melanoma from lung (same patient as Malme 3) |
| M14 | UCSD | HLA-A2.1 human melanoma |
| K562 | ATCC | human erythroleukemic cell line; target for NK cells |
| JY cells | ATCC | EBV-transformed, human B cell line expressing HLA-A2.1 and B7 |
| P815 and P1024 | ATCC | DBA/2 mouse mastocytoma cell lines |
| Jurkat A2.1 | ATCC | acute T cell leukemia transfected with human HLA-A2.1 |

ATCC: American Type Culture Collection

EXAMPLE 2

Trial of Cytotoxic T Cell Infusions Against Melanoma

Purpose of Trial

This example teaches the effectiveness of cytotoxic T Cell infusions in the treatment of melanoma as assessed according to the following factors:
 1. safety and toleration of re-infused autologous CTLs after in vitro immunization;
 2. kinetics of infused CTLs in the systemic circulation factoring in limiting dilution analysis;
 3. whole body disposition of CTLs by radioscintography;
 4. cell composition of biopsied nodules by immunohistology (CTLs, TH, NK, B cells); and
 5. regression of measurable lesions and duration of response over two months.

Patient Populations

Eligibility for treatment required patients to have histologically-documented, unresectable malignant melanoma that was measurable or evaluable, and the HLA-A2 haplotype. Pretreatment evaluation included radiologic evaluation of the brain by MRI or CT scan, CT scanning of the chest and abdomen, and physical examination, especially of the skin and lymph nodes. The total number of patients treated was fifteen (nine male and six female). The ages ranged from 33 to 75 years with an average of 58 years. The average duration of metastatic disease was 1.5 years. A pretreatment skin test to determine whether a state of anergy existed was performed on 14/15 patients with 5/14 testing negative for all seven of the common antigens evaluated. Patients were screened for the HLA-A2 haplotype by FACS analysis with an HLA-A2 specific monoclonal antibody (BB7.2). Subtyping was performed by PCR analysis. All, but one of the patients, were HLA-A*0201, the exception (patient 08) was HLA-A*0205.

Treatment with Ex Vivo Generated Autologous CTLs

Fifteen patients were treated under is clinical protocol. All patients received, at least a single infusion of autologous CTLs. The number of cycles and the dose of cells administered to each patient are summarized in Table 1. The number of cells generated in vitro was dependent on patient-related factors such as the numbers of PBMCs isolated from the aphaeresis procedure and the number of CD8$^+$ T cells present in each PBMC preparation. Since all of the cells generated in vitro were re-infused into the donor, doses administered to each patient were necessarily varied. In an attempt to normalize the doses between patients, a calculated "potency" score was recorded for each dose. The value was obtained by multiplying the total number of cells by the lytic activity obtained with peptide-loaded target cells. Doses of T cells infused ranged from a minimum of $4\times10^7$ (patient 08) to a maximum of $3.2\times10^9$ (patient 13). Patients were entered into a second, third or fourth cycle of treatment based on their clinical status at the end of each cycle. The number of PBMCs obtained from the aphaeresis samples tended to be lower in patients undergoing additional cycles, is especially if the start of the subsequent cycle was close to the end of the previous one. This is attributed to persistent lymphopenia due to the IFNα-2b administered during the previous cycle. The total number of naïve CD8$^+$ T cells isolated was dependent on its percentage in each of the PBMC preparations. The percent of CD8$^+$ T cells varied between 8% to 31% among the patients. The obtained expansion factor also contributed to the final cell numbers and ranged from 0.1-6.0 fold. The procedure for generating CTLs ex vivo is taught in the Specification and Example 1, above.

Up-Regulation of Class I and Melanoma-Associated Antigens in Response to IFNα-2b In an attempt to enhance the ability of the antigen-specific CTLs to lyse melanoma cells in vivo, low dose IFNα-2b was administered for five consecutive days prior to the CTL infusion, and thrice weekly for an additional four weeks. One way to measure an in vivo response to the cytokine is to evaluate biopsies obtained at serial time points by immunohistochemical analysis for positive staining with specific antibodies. Serial biopsies were obtained in one patient with multiple skin lesions patient 04) for evaluation of both class I and antigen expression. The biopsies indicated Class I and MART-1 expression were weakly positive prior to any treatment (biopsy A). Following five days of subcutaneous injections of 10 MU/m$^2$, a dramatic increase in these two markers was noted (biopsy B). For tyrosinase and gp100, immunohistochemical staining was negative to weakly positive, respectively in the pretreatment samples (biopsy A). After the initial five-day IFNα dose, and thirteen additional treatments, expression of these later antigens was increased in the stained tissue samples (biopsy C).

Antigenic Specificity of Ex Vivo-Generated CTLs

CTLs generated from all patients were evaluated on the day of release against peptide-loaded T2 targets, an HLA-A2 melanoma cell line (Malme3M) and an autologous melanoma line, if biopsy material was available to establish a line. Each prepared dose of cells was evaluated for its cytolytic activity. Peptide-loaded T2 cells, presenting either each peptide alone, or all four peptides simultaneously, were used to determine the specificity of the CTL response generated for each patient.

The ability to lyse endogenously-expressed, melanoma-associated, antigen-bearing cells was assessed with an HLA-A2 matched line or an autologous tumor line. In addition to cytolytic activity, antigen-specificity was evaluated with an established method for detecting intracellular gamma interferon production, made in response to a specific peptide stimulus. The CTLs generated at the end of the ex vivo protocol were evaluated by this method. The percent of cells specific for each of the peptides was recorded individually. The total number of specific cells in each bulk CD8 culture from patient 13 was calculated by adding each of the peptide specificities detected in that population of T cells. An increase in the total number of specific cells could be detected with each successive treatment cycle.

Detection of CD8 and CD4 Cells Infiltrating Tumor Biopsies Post-CTL Therapy

Biopsy samples from all patients prior to, during and after treatment would have been ideal. However, the experimental conditions allowed for biopsy samples from only a limited number of patients. Tumor tissue was obtained from five of the fifteen patients enrolled in the study. In two patients (patients 08 and 13) biopsy samples were available at five and six weeks post T cell therapy, respectively. Examination of the tissue samples revealed the presence of both infiltrating CD8 and CM cells. One of the tumor samples was taken from a skin lesion in the occipital region of the scalp, which increased in size by the time of the follow up examination, four weeks after a second Vision of T cells. The biopsy revealed necrosis of the tissue that was heavily infiltrated with lymphocytes. The other biopsy was from the head of a femur bone, removed during hip replacement surgery. The skin lesion from patient 08 was strongly positive (4+) for both a general class I, and a specific HLA-A2 marker. Tyrosinase and gp100 were weakly positive (1+ and 2+, respectively), while MART-1 was negative in this same sample. Regions of the biopsy from patient 13 were also necrotic, with more heterogeneous staining; distinct populations of tumor cells lacking expression of the HLA-A2.1 molecule, and one or more of the MAAs. However, intact tissue regions revealed strong class I (4+), and all of the melanoma-associated antigens. The lymphocytic infiltrations in this later sample appeared to surround the tumor nodules rather than to deeply infiltrate them. However, the highest percentage of cells directly associated with the tumor were CD8 cells. The lark of pretreatment biopsy samples from both of these patients prevented a confirmation of similar types of infiltrating cells in tissue samples prior to treatment.

CT Scans Post-T Cell Therapy Confirm an Objective Response

CT scans were part of the pretreatment screening criteria and the post treatment follow-up examination. Patient 10 received a single infusion of $8 \times 10^8$ CTLs (Jul. 27, 1999) five weeks after the pretreatment scan (Jun. 23, 1999). When a CT scan of the chest was repeated one month after the infusion (Aug. 27, 1999), a dramatic decrease in the size of a lung lesion was noted. Similarly, patient 14 underwent a chest CT scan as part of the enrollment process (Sep. 10, 1999), three and one-half weeks before a first infusion with $6.6 \times 10^8$ cells (Oct. 5, 1999). A follow-up CT scan (Jan. 7, 1999), one month after a second infusion with $11.5 \times 10^8$ cells revealed dramatic shrinkage in three separate lesions. Patient 13 also had an objective response as measured in pre and post CT scans. Paratracheal adenopathy went from 7.8 cm$^2$ (pre-study) to 4.4 cm$^2$ after cycle I, and disappeared following cycle II.

Presence of an Anergic State Did not Preclude Ability to Generate CTLs or Prevent a Clinical Response Most of the patients treated under this protocol had received previous medical intervention A pretreatment skin test was performed to determine if an anergic response to a panel of seven common antigens correlated with either an inability to generate CTLs ex vivo, or prevent a documented clinical response. The ability to generate CTLs ex vivo did not correlate with the patient's pretreatment skin test results. It should be noted that patients 03 and 04 (both mixed responders) had repeat skin tests prior to the start of the second cycle and remained anergic.

EXAMPLE 3

Generation of HER-2/neu Specific CTLs Capable of Lysing Breast & Ovarian Tumor Cells We were interested in applying our CTL-generation technology to other tumor types to determine if all forms of cancer can be targeted with this approach. HER-2/neu is a proto-oncogne with homology to EGFR that is amplified and over-expressed in many human cancers, largely adenocarcinomas of the breast, ovary and colon. It is often associated with aggressive disease and can be an indicator of a poor prognosis. It has been studied in several clinical trials as a possible target for these types of cancers.

In the early 1990's HER-2/neu HLA-A2.1 restricted peptide epitopes were identified either by computer-assisted peptide binding algorithms or by mapping CTLs isolated from ascites of ovarian cancer patients (Table 3).

TABLE 3

| HLA-A2.1-Restricted HER-2/neu Peptides | | | | | |
|---|---|---|---|---|---|
| HER-2/neu Peptides | PRI # | Other ID # | Location | Sequence (SEQ ID NO) | Reference |
| 48-56 | 827 | D113 | EC | HLYQGCQVV (SEQ ID NO: 13) | Disis et al., 1994 |
| 369-377 | 835 | E75 | EC | KIFGSLAFL (SEQ ID NO: 8) | Fisk et al., 1995 |
| 650-658 | 838 | GP1 | TM | PLTSIISAV (SEQ ID NO: 15) | Fisk et al., 1995 |
| 654-662 | 837 | GP2 | TM | IISAVVGIL (SEQ ID NO: 14) | Peoples et al., 1995 |

TABLE 3-continued

HLA-A2.1-Restricted HER-2/neu Peptides

| HER-2/neu Peptides | PRI # | Other ID # | Location | Sequence (SEQ ID NO) | Reference |
|---|---|---|---|---|---|
| 773-782 | 861 | N/A | IC | VMAGVGSPYV (SEQ ID NO: 16) | Lustgarten et al., 1997 |
| 789-797 | 826 | E90 | IC | CLTSTVQLV (SEQ ID NO: 7) | Disis et al., 1994 |
| 851-859 | 862 | E89 | IC | VLVKSPNHV (SEQ ID NO: 17) | Disis et al., 1994 |
| 971-979 | 863 | C85 | IC | ELVSEFSRM (SEQ ID NO: 18) | Fisk et al., 1995 |

All of the peptides were synthesized, given an identification number (PRI#) and evaluated for the ability to generate CTLs ex vivo utilizing the same method we employed for melanoma-associated, T cell peptide epitopes. CD8 cells were isolated from normal donors to determine the ability to routinely generate CTLs ex vivo with *Drosophila* cells loaded with known CTL peptide epitopes. Peptides 826, 835, 861 and 863 had the highest frequency of CTL generation (Table 4).

TABLE 4

Frequency of HER-2/neu CTL Generation in Normal Donors

| Donor | 826 | 827 | 835 | 837 | 838 | 861 | 862 | 863 |
|---|---|---|---|---|---|---|---|---|
| 193 | + |   | + |   |   |   |   |   |
| 194 | + | − | + | − | − | + |   | + |
| 195 | + |   | + |   |   | + |   | + |
| 196 | + | − | + | − | − | + |   |   |
| 197 | + | − | + | − | + | + | − | + |
| 198 | − | − | + | − | + | + | − | + |
| 207 | + |   | + |   |   | + |   | + |
| 212 | + |   | + |   |   | + |   | + |
| 218 | + |   | + |   |   | + |   | + |
| 232 | − |   | + |   |   | + |   | − |
| 233 | + |   | + |   |   | + |   | + |
| 241 |   | + |   |   |   | + |   |   |
| 243 |   | + |   |   |   | + |   |   |

Figure 12:
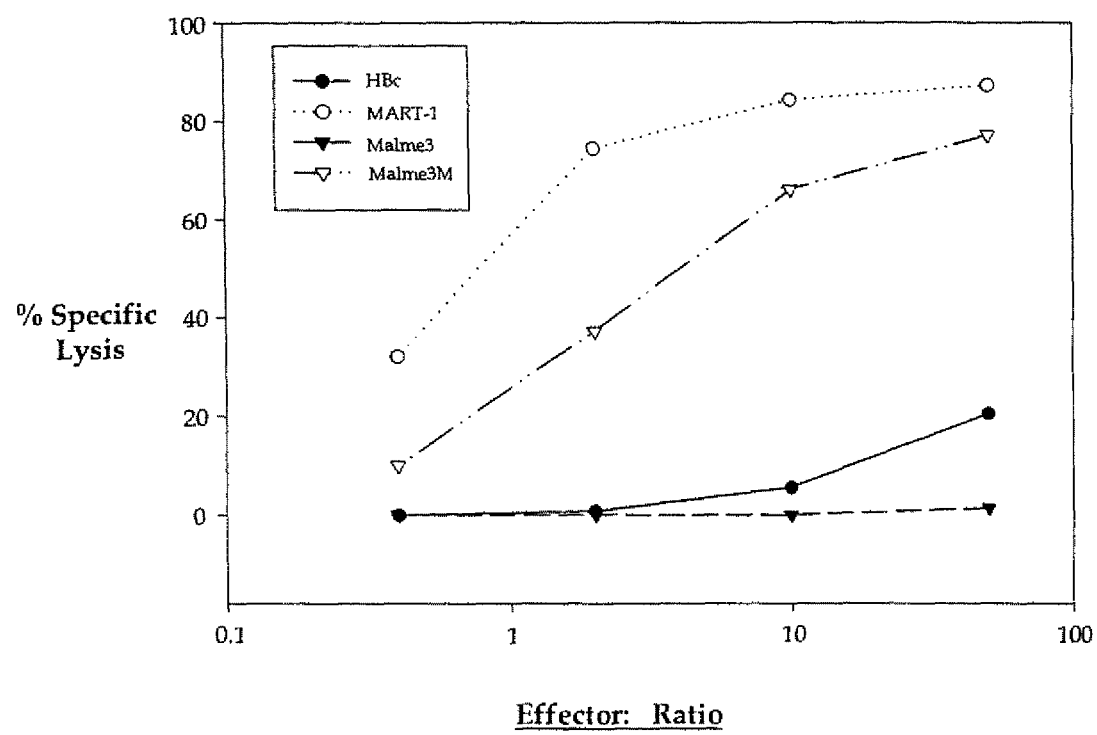
FIG. 12: This figure demonstrates the anti-peptide and anti-tumor response for MART-1 specific effector cells. T2 cells were loaded with ART-1 peptide or a negative control (HBc). Malme3M is a melanoma line, Malme3 is a non-tumor cell line.

While transfected *Drosophila* cells have the unique ability to present up to ten different peptide epitopes (FIG. 10), we selected the four HER-2 peptides 826, 835, 861 and 863 due to the frequency of generating CTLs to these peptides ex vivo. These four different HER-2 peptides represent weak to moderate binders to the HA-A2.1 molecule presented on the surface of the transfected *Drosophila* cells. We tend to include M binders that are weak, as our experience in with melanoma-associated peptides suggests that weak class I binders generally generate potent CTLs which recognize tumor cells, if indeed they represent native T cell epitopes. The majority of the tumor-associated proteins that we target are self-antigens and as such would be expected to have the high affinity for the class I molecule that is seen with viral peptides. The low to moderate binders generally generate CTLs that lyse the tumor cells very efficiently. This was demonstrated with the MART-1 peptide which is a low affinity binder on the *Drosophila* cells (FIG. 3), yet represents an epitope that routinely generate potent CTLs capable of lysing both peptide-loaded target cells (T2), or more importantly, melanoma cells (Malme3M) (FIG. 12).

HER-2/neu is a member of the EGF-R family and functions as a growth factor receptor. HER-2 protein is expressed during fetal development in humans. In adults, the protein is weakly detectable in epithelial cells of many normal tissues. In normal cells the HER-2 gene is present as a single copy. Amplification of the gene and/or over-expression of the associated protein has been identified in many human cancers including breast, ovarian, uterine, stomach and adenocarcinoma of the lung. Sequence differences between HER-2 and EGF-R receptor are noted in Table 5. Three of the four HER-2 peptides we have evaluated have three or more amino acids changes between the two proteins. A single amino acid change is sufficient to discriminate between the two proteins.

TABLE 5

HER-2/neu Versus EGF-R

| PROTEIN | PEPTIDE # | SEQUENCE (SEQ ID NO) | # CHANGES |
|---|---|---|---|
| HER-2/neu EGFR | 835 | KI*FG*S*LAFL* (SEQ ID NO: 8) *SI*S*G*DL*HII* (SEQ ID NO: 37) | 5 |
| HER-2/neu EGFR | 861 | V*MA*GV*GSP*YV (SEQ ID NO: 16) V*AA*SV*DNP*HV (SEQ ID NO: 38) | 5 |
| HER-2/neu EGFR | 863 | EL*VS*EFS*R*M (SEQ ID NO: 18) EL*II*EFS*K*M (SEQ ID NO: 39) | 3 |
| HER-2/neu EGFR | 826 | CLTSTVQL*V* (SEQ ID NO: 7) CLTSTVQL*I* (SEQ ID NO: 40) | 1 |
| HER-2/neu EGFR | 689-697 | RLLQE*T*ELV (SEQ ID NO: 41) RLLQE*RE*LV (SEQ ID NO: 42) | 1 |

Figure 13:
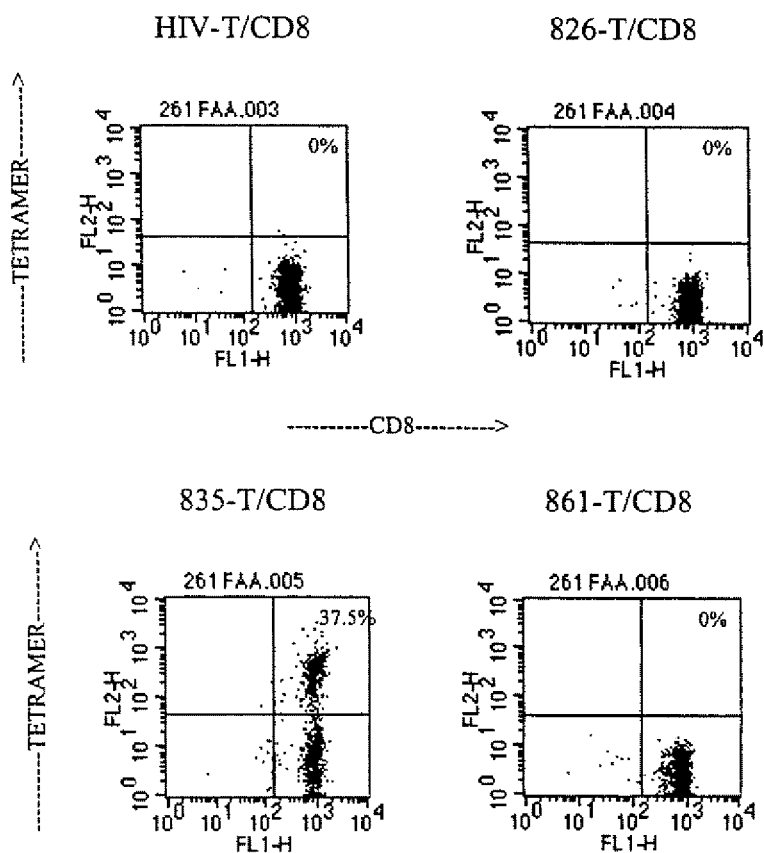
FIG. 13, Panels A and B:
This figure shows the tetrameric stag of the HER-2 specific CD8 effector cells from two different donors.
Figure 13:
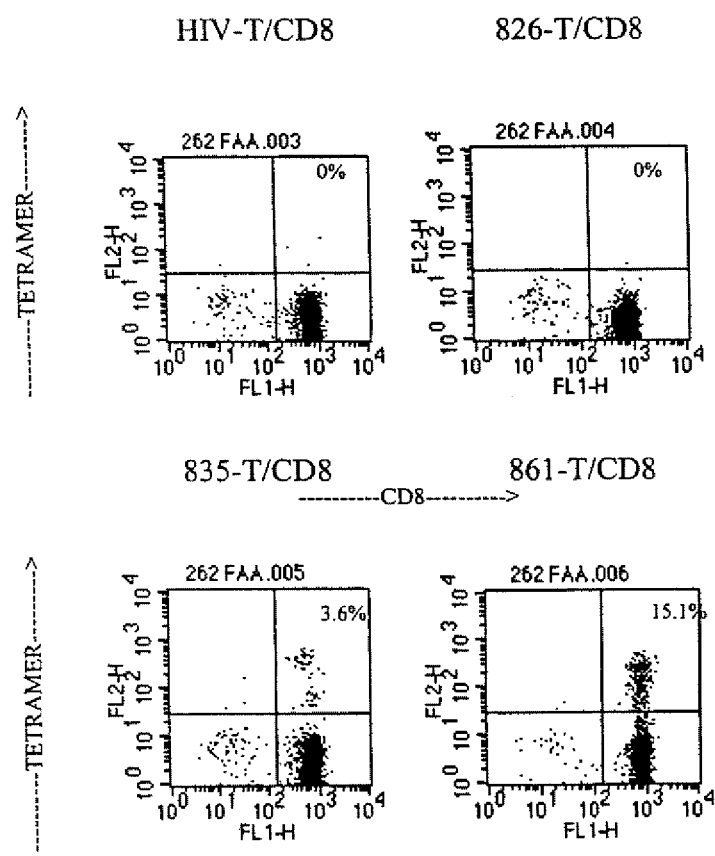

Once the CTLs have been generated after the four-week ex vivo stimulation protocol, we evaluated whether peptide specific cells were present using HLA-A2.1 tetrameric molecules prepared with the immunizing peptides. As demonstrated in FIG. 13, the ability to generate peptide-specific CTLs was donor-dependent. In Panel A (donor 261), the donor made a strong CT response to peptide 835 (37.55%). In Panel B (donor 262), peptide-specific CTLs can be detected with both the 835 and 861 tetrameric molecules (3.6% and 15.1%, respectively). This supports the use of multiple peptides to guarantee peptide specific CTLs at the end of the stimulation protocol. This ex vivo protocol allows one to generate multiple-specific CTLs relatively easily.

Anti-Peptide and Anti-Tumor Responses

Figure 14:
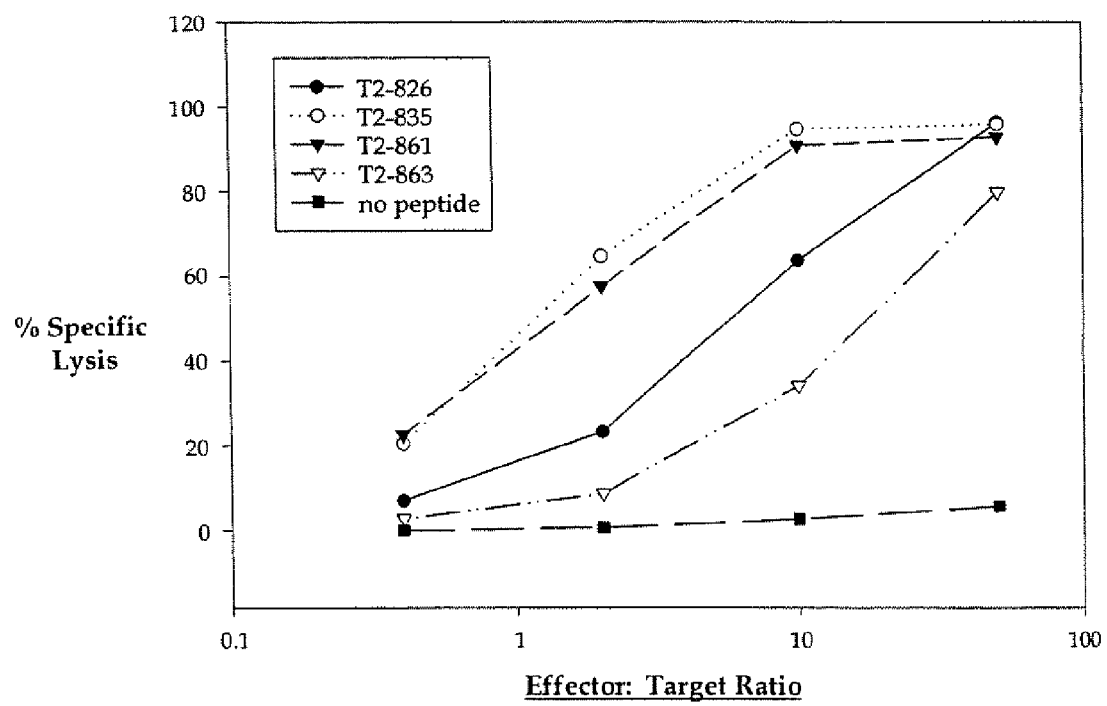
FIG. 14: This figure reveals the anti-peptide response for the HER-2 effector cells evaluated on peptide-loaded T2 cells.

After the completion of the full ex vivo protocol, the CTLs generated were evaluated for antigen-specificity. To generate the CTLs on Day 0 Drosophila cells were loaded with a combination of the four HER-2 peptides. At the end of the four-week ex vivo stimulation protocol, the bulk CD8 culture was evaluated for antigen-specificity. T2 cells loaded with each of the immunizing peptides were used as target cells. In FIG. 14, a typical response is depicted. The bulk culture contains specificity for each of the four HER-2 peptides. The anti-tumor response was assessed on an ovarian tumor cell line (ATCC; HTB-77). When a target cell line is not HLA-A2.1-restricted, we transfected the cell line to have a +/− assay system. When HLA-A2.1 was transfected into the HTB-77 line, an enhanced killing by CD8 effector cells was noted (FIG. 15, Panels A to D). HER-2 specific effectors, representing the individual peptides were evaluated to confirm the presentation of each of the peptide epitopes on is tumor cell line.

Figure 16:
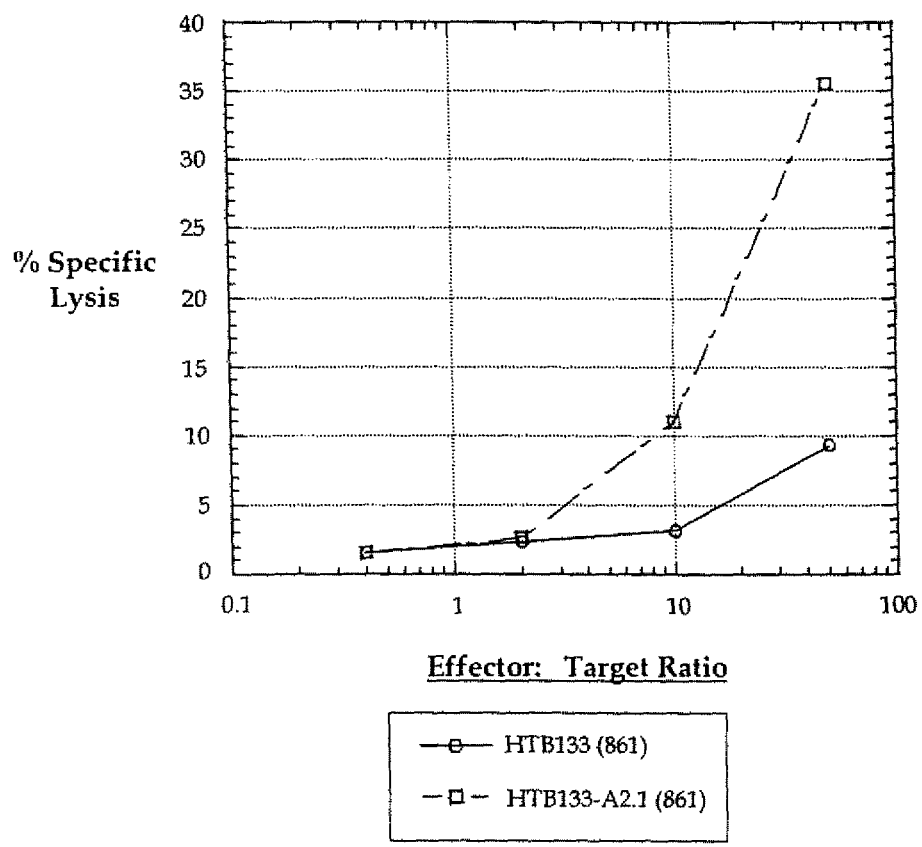
FIG. 16: This figure shows the enhanced killing of a breast cancer cell line (HTB-133) when transfected with HLA-A2.1

A breast adenocarcinoma cell line (ATCC; HTB-131), transfected with HLA-A2.1 was also evaluated for the ability to demonstrate tumor lysis with the HER-2 specific peptide effectors. CTLs specific for peptide 861 could lysis is tumor cell line when transfected with HLA-A2.1 (FIG. 16).

IFNγ Treatment Required for Tumor Cell Lysis

Figure 17:
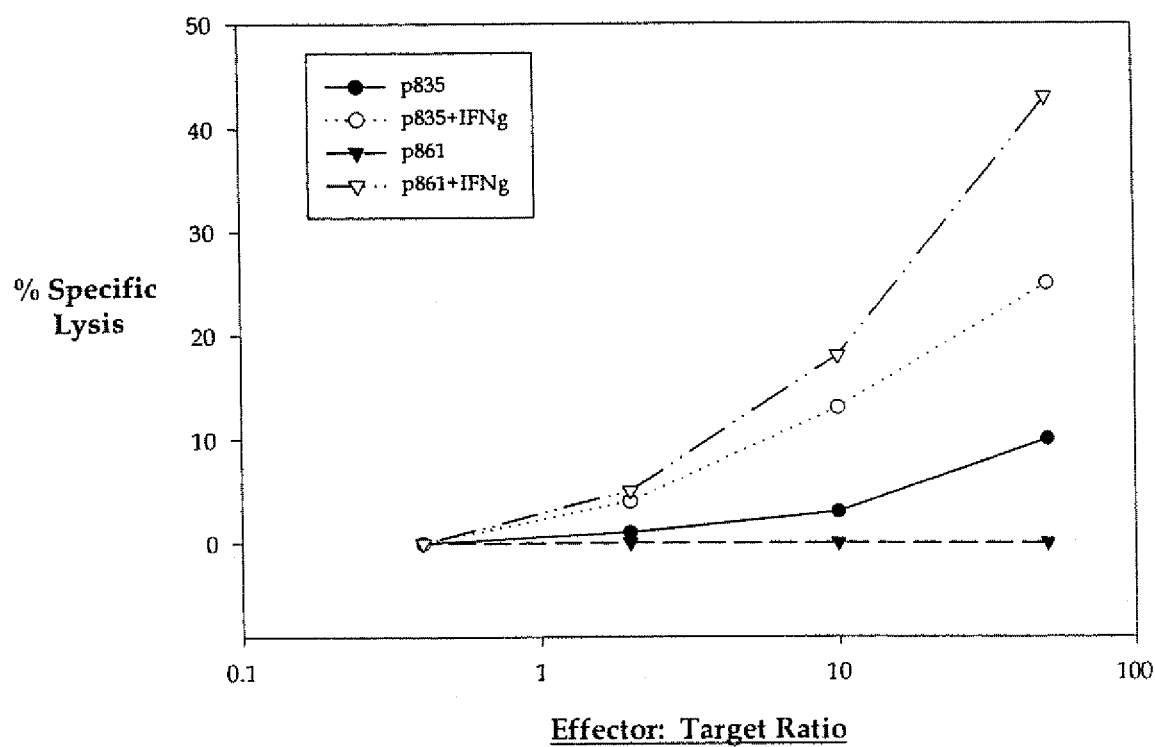
FIG. 17: This figure shows that IFNγ pretreatment is required to demonstrate lysis of the tumor cell line HTB-77/A2.1.
Figure 19:
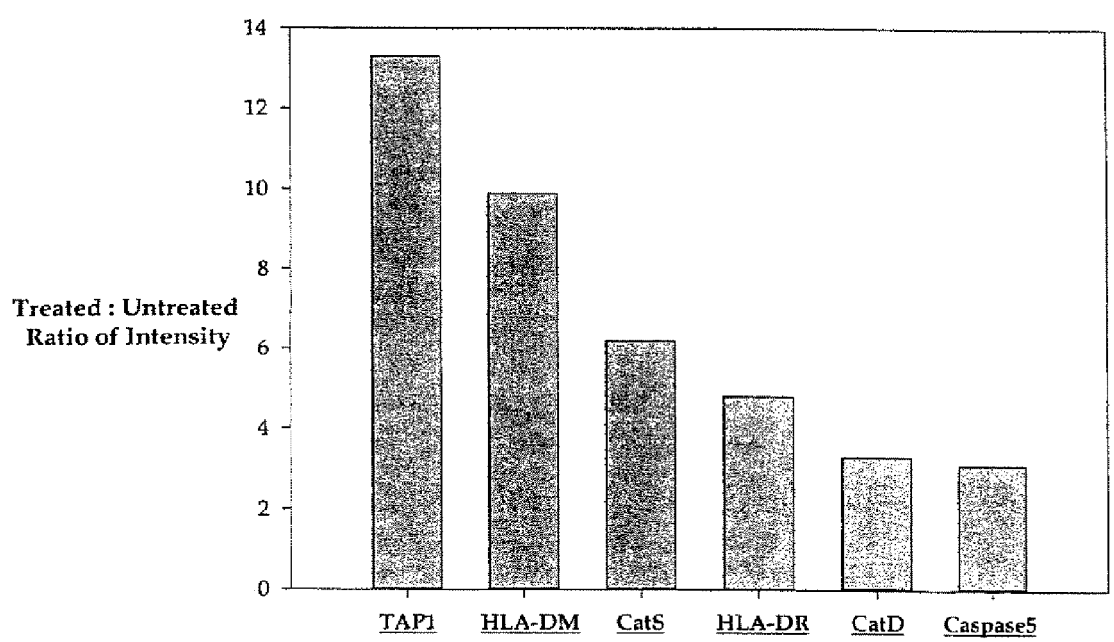
FIG. 19. This graph shows which protein mRNA levels are elevated in the HTB-77/A2.1 cells after an induction with if IFNγ.

The HTB-77/A2.1 cell line requires a pretreatment with IFNγ to demonstrate peptide-specific lysis. The cells were treated with 500 U/ml of IFNγ (specific activity of 25 ng/ml) for twenty-four hours prior to the initiation of the $^{51}$Cr-release assay. In FIG. 17, the addition of the IFNγ resulted in enhanced lysis of the HLA-A2.1 transfected cell line. To determine the effect of this dose of IFNg on the surface expression of both HLA-A2.1 and HER-2, a FACS analysis was performed to determine the levels of these molecules after both twenty-four and forty-eight hours of induction. FIG. 18, Panels A and B depict the FACS analysis results. In Panel A, there was no enhancement of the HER-2 molecule on the surface of the HTB-77 cells at twenty-four and forty-eight hours after induction with IFNg. In the HLA-A2.1 transfected cells, neither HER-2 nor HLA-A2.1 demonstrated an increase in surface level of expression after a similar treatment protocol. What was noted was an increase in the level of TAP-1 expression, as well as HLA-DM and -DR, Cathepsin S and D and Caspase 5, when the mRNA levels were evaluated by microarray DNA chip analysis (FIG. 19). This would explain why there is an enhance killing of the HTB-77/A2.1 cells in the presence of IFNγ. An upregulation of this particular molecule would result in more efficient processing of the HER-2 molecule, allowing better presentation of the peptides of interest.

Peptides

Synthetic peptides were made by standard Fmoc chemistry using a peptide synthesizer (Gilson Company, Inc.) All peptides were purified to >95% purity by reverse-phase HPLC on a C-8 column. Purity and identity were established using a mass spectrometer with electrospray ionization. Melanoma-associated peptides included: peptide 819 was MART-1 specific (AAGIGILTV SEQ ID NO:6), 817 and 853 were both gp100 peptides (ITDQVPFSV SEQ ID NO:4 and KTWGQYWQV SEQ ID NO:5, respectively), tyrosinase-specific peptides were 689 and 792, with 792 representing the post translational modified version (YMDGTMSQV SEQ ID NO:2) of the native sequence (YMNGTMSQV SEQ ID NO:1) represented by peptide 689. Peptides 826 (CLTSTVQLV SEQ ID NO:7) and 835 (KIFGSLAFL SEQ ID NO:8) represented HER-2/neu sequences from the intracellular and extracellular domains, respectively of the p185 protein. Pec60$_{20}$ (ALALAALLVV SEQ ID NO:10) Pec60$_{25}$ (ALLVVDREV SEQ ID NO:11) were overlapping sequences representing a mucinous protein detected in ovarian tumor lines. C-lectin also was a protein detected in ovarian tumor cell lines and a peptide from its sequence (C-lectins) is represented by KMASRSMRL SEQ ID NO:9.

In Vitro Cytotoxicity Assay

Standard $^{51}$Cr-release assays were performed to determine CTL effector cell recognition of melanoma-associated peptide epitopes loaded onto T2 cells. Harvest 3×106 T2 cells were grown in RPMI+10% FBS (media). 0.1 mCi of $^{31}$Cr was added and incubated at 37° C. in a water bath. Labeled cells were added to 10 ml of 4% wash (RPMI+4% FBS) and pellet, washed two additional times, and re-suspended in media to a final concentration of 0.2×106/mL to record radioactivity of spontaneous versus detergent lysed cells. The cells were pulsed with the appropriate peptide(s) at 20 μg/mL for thirty minutes. 50 μl was added to each 96-well plate each containing CD8 effector cells at 10, 2, 0.4, and 0.08×10$^6$/mL, which was incubated at 37° C. for six hours, spun and harvested for supernatant.

Flow Cytometry and Tetramer Staining

The cells were labeled with FITC- or PE conjugated monoclonal antibodies by incubation at 4° C. for 30 minutes in FACS buffer (1% BSA, 0.02% NaN$_3$ in PBS), followed by a wash in the same buffer. Cells were fixed in 0.5% formaldehyde prior to data acquisition and analysis on a FACScan flow cytometer (Becton Dickinson) with its CellQuest software. Nonspecific staining was measured with the same secondary antibody used to label purified primary antibodies, or an isotype-matched control when the primary antibodies were directly labeled. Tetrameric staining was performed with HLA-A2.1 specific HIVgag tetrameric molecules (Beckman Coulter) harboring the sequence SLYVTVATL SEQ ID NO:43 as a negative control HER-2 specific tetramers were made with the sequences CLTSTVQLV (826 SEQ ID NO:7), KIFGSLAFL (835 SEQ ID NO:8), or VMAGVGFSPYV (861 SEQ ID NO:16) peptides. PE-labeled tetrameric HLA-A2.1-peptide complexes were used in conjunction with fluorescein isothicyante (FITC)-labeled anti-human CD8a (BD PharMagin) monoclonal antibodies to stain epitope-specific CD8+ T cells as described in package insert. Samples were analyzed by two-color flow cytometry on a Becton Disckenson FACScan, and gated CD8+ T cells were examined for staining with tetrameric HLA-A2.1-peptide complexes.

EXAMPLE 4

Generation of Additional Breast and Ovarian Specific CTLs with this Ex Vivo Stimulation Protocol We have demonstrated the ability to generate CTL responses to all known HLA-A2.1-restricted peptide epitopes for several tumor antigens of different tumor origins. Our initial studies focused on melanoma where we were able to demonstrate objective clinical responses in patients treated with CTLs specific for four different peptide epitopes specific for the MART-1, gp100 and tyrosinase melanoma-associated proteins [Richards et al., *Amer. Soc. Clin. Oncol.*, San Francisco, Calif. (2001, May)].

To extend the ability to raise CTLs to other tumor antigens present in a wide variety of other cancers we have selected published and novel sequences to tumor antigens common to several different tumor types. These include AES, MUG-1, CEA, FBP, C-Lectin, NY-ESO-1, Pec60, CA-125, MAGE-3, telomerase and G250. Table 7 describes these antigens, the frequency of expression and the cancers, which express them. The frequency of response to these peptides with our ex vivo stimulation protocol is listed in Table 6.

TABLE 6

Frequency of Response to Breast and Ovarian Peptide Epitopes in Normal Donors

| Donor | 879 | 893 | 894 | 899 | 900 | 901 | 902 | 903 | 906 | 907 | 908 | 909 | 910 | 911 | 912 | 913 | 914 |
|---|---|---|---|---|---|---|---|---|---|---|---|---|---|---|---|---|---|
| 248 | + | + | + | | | | | | | | | | | | | | |
| 249 | + | + | + | | | | | | | | | | | | | | |
| 250 | + | − | + | | | | | | | | | | | | | | |
| 251 | − | − | + | | | | | | | | | | | | | | |
| 252 | + | − | + | | | | | | | | | | | | | | |
| 253 | − | − | + | + | | | | | | | | | | | | | |
| 254 | + | − | + | + | | | | | | | | | | | | | |
| 255 | | | | | − | + | + | − | + | + | + | + | | | | | |
| 256 | | | | | + | − | + | + | + | + | − | + | | | | | |
| 257 | | | | | | | | | | | | | + | + | + | | |
| 259 | | | | | | | | | | | | | + | − | − | | |
| 260 | | | | | − | − | − | − | | | | | | | | + | |
| 261 | | | | | | | | | + | + | + | + | | | | | |
| 262 | | | | | | | | | + | + | − | + | | | | | − |
| 265 | + | + | + | + | − | − | − | − | + | | | | + | + | | | − |

TABLE 6

Tumor Antigen Descriptions

| Antigen | Description |
|---|---|
| CA-125 | Cancer Antigen 125 is an epithelial cell marker expressed by ovarian tumors and some ovarian cell lines. About 85% of ovarian cancer patients have an increased serum CA125 and is therefore commonly used as a serum tumor marker. (Cancer Letters (1999, October) 145(1-2) pg. 133-141) |
| MUC-1 | Mucin is a transmembrane glycoprotein expressed on both normal and malignant epithelium. The underglycosylated form of MUC-1 over-expressed on the cell surface of many human adenocarcinomas such as breast and ovarian cancer, as well as hematological malignancies including multiple myeloma and B-cell lymphoma. (Blood (1999, June) 93(12) pg. 4309-4317) |
| G250 | A renal cell carcinoma associated antigen expressed in 85% of RCC's but not normal kidney tissue. It is identical to the tumor-associated antigen MN/CAIX which is expressed in about 50% of invasive breast cancers. (Cancer Research (1999, November); 59(21) pg. 5554-5559) |
| FBP | Folate binding protein is a receptor involved in folate transport. It is over-expressed in over 90% of ovarian tumors and 20-50% of breast cancers. (Anticancer Research (1999 Jul-Aug) 19(4B) pg. 2907-2916) |
| HER-2/neu | A proto-oncogene (HER-2) encoding a transmembrane protein similar in sequence and structure to EGF-R, HER-2/neu is over-expressed as much as 200 fold over normal tissues in breast and ovarian tumors. It has also been identified in renal cell and lung carcinomas. (J. Exp. Med.(1995, June)Vol. 181, pg. 2109-2117) |
| NY-ESO-1 | A cancer-testes antigen found in 30% of breast, prostate and ovarian cancers, lung cancer, bladder cancer, head and neck cancer and melanoma. Patients who have cancers with tumors expressing this antigen usually have circulating antibodies against it as well. (J. Immunology (2000) vol. 165 pg. 948-955) |
| CEA | Carcinoembryonic antigen is a tumor-associated antigen frequently expressed in epithelial tumors (colon, breast, lung). CEA levels in the serum can correlate with disease stage and is used to monitor treatment and reoccurrence of disease. (Human Immunology (1998) vol. 59 pg. 1-14) |
| MAGE-3 | A cancer-testis antigen expressed on 70-80% of metastatic melanoma lesions and cell lines. It is a member of the family of melanoma associated or MAGE proteins. In addition, MAGE-3 has been found in 20-60% of epithelial tumors (colon, breast, lung, gastric carcinomas). (Human Immunology (1998) vol. 59 pg. 1-14) |
| AES | The amino enhancer of split protein is part of a set of transcriptional repressers encoded by the Enhancer of split genes. This tumor antigen was identified in tumor-associated lymphocytes of ovarian and breast tumors. (Molecular Immunology (1998) 35(17)pg. 1121-1133) |
| HTR | Telomerase(hTR) is a specialized type of reverse transcriptase (hTRT or hTERT) that catalyzes the synthesis and extension of telomeric DNA. The activity of this enzyme is elevated in about 90% of all human tumors including cancers of the breast, thyroid, bladder, cervix, prostate, colon, pancreas and stomach. (Cancer Research (2001, December) 61(23)pg. 8366-8370) |

What is claimed is:

1. A method for making non-naturally occurring antigen presenting cells (nnAPC) for ovarian cancer therapy, said method comprising the steps of:
   (a) preparing an insect cell line from Drosophila melanogaster eggs;
   (b) growing said insect cells;
   (c) introducing a pRmHa-3 plasmid, said plasmid encoding at least the following proteins: a human class I HLA protein, β2 microglobulin, at least one T-cell co stimulatory factor, an intercellular adhesion molecule 1 and at least one lymphocyte function antigen;
   (d) transfecting said insect cells with a phshneo plasmid and said pRmHa-3 plasmid;
   (e) creating nnAPCs by contacting said insect cells with $CuSO_4$ to induce expression of the proteins in said insect cells; and
   (f) contacting said nnAPC with with a combination of peptides comprising MAGE-3 $_{271-279}$ (SEQ ID NO: 33) in combination with at least one other peptide selected from the group consisting of Pec $60_{20}$ (SEQ ID NO:10), Pec$60_{25}$ (SEQ ID NO:11) and C-lectin (SEQ ID NO:9).

2. The method of claim 1 wherein the human class I HLA protein is human I HLA A2.1.

3. The method of claim 1 wherein the T-cell co-stimulatory factor proteins comprise a B7 protein.

4. The method of claim 3 wherein the B7 protein is B7.1, or B7.2.

5. The method of claim 1 wherein the lymphocyte function antigen is LFA-I, LFA-2 or LFA-3.

6. The method of claim 1 wherein the cancer is ovarian cancer.

7. A non-naturally occurring antigen-presenting cell comprising a pRmHa-3 plasmid, said plasmid encoding at least the following proteins: a human class I HLA protein, β-2 microglobulin, at least one T-cell stimulatory factor, an intercellular adhesion molecule 1, at least one lymphocyte function antigen and wherein the non-naturally occurring antigen-presenting cell further comprises the MAGE-3 peptide designated as MAGE-3 $_{271}$-$_{279}$ (SEQ ID NO: 33) in combination with at least one other peptide selected from the group consisting of Pec $60_{20}$ (SEQ ID NO:10), Pec$60_{25}$ (SEQ ID NO:11) and C-lectin (SEQ ID NO:9).

8. The cell of claim 7 wherein the human class I HLA protein is human class I HLA A2.1.

9. The cell of claim 7 wherein the T-cell co-stimulatory factor proteins comprise a B7 protein.

10. The cell of claim 9 wherein the B7 protein comprises B7.1, or B7.2.

11. The cell of claim 7 wherein the lymphocyte function antigen comprises LFA-1, LFA-2or LFA-3.

* * * * *